(12) United States Patent
Yamashita et al.

(10) Patent No.: US 6,858,591 B2
(45) Date of Patent: Feb. 22, 2005

(54) ANTIBIOTIC AA 896 ANALOGS

(75) Inventors: Ayako Yamashita, Englewood, NJ (US); Emily Boucher Norton, Nyack, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/131,938

(22) Filed: Apr. 25, 2002

(65) Prior Publication Data

US 2003/0087874 A1 May 8, 2003

Related U.S. Application Data

(60) Provisional application No. 60/286,401, filed on Apr. 25, 2001, provisional application No. 60/290,139, filed on May 10, 2001, provisional application No. 60/286,297, filed on Apr. 25, 2001, provisional application No. 60/290,140, filed on May 10, 2001, provisional application No. 60/286,402, filed on Apr. 25, 2001, and provisional application No. 60/290,156, filed on May 10, 2001.

(51) Int. Cl.$^7$ .......................... A01N 43/04; A61K 31/70
(52) U.S. Cl. .......................... 514/50; 514/48; 514/49; 514/51; 536/28.1; 536/28.3; 536/28.4; 536/28.53
(58) Field of Search ............................. 536/28.1, 28.2, 536/28.4, 28.53; 514/48, 49, 50, 51

(56) References Cited

FOREIGN PATENT DOCUMENTS

| JP | 05078385 | 3/1993 |
|---|---|---|
| WO | WO 97/41248 | 6/1997 |

OTHER PUBLICATIONS

Ubukata et al. J. Org. Chem. (1992), vol. 57, pp. 6392–6403*
Harry J. Minnemeyer, et al.; Journal of Organic Chemistry; vol. 26; pp. 4425–4429; (1961).
Herman Gershon, et al.; Journal of Medicinal Chemistry; vol. 6; pp. 87–89; (1963).
B.R. Baker and Mitsutaka Kawazu, et al.; Journal of Medicinal Chemistry; vol. 10 (3): pp. 311–313; (1967).
Eugene Coats, et al.; Journal of Medicinal Chemistry; vol. 14; No. 5; pp. 913–919; 1970.
B.R. Baker and James L. Kelley; Journal of Medicinal Chemistry; vol. 14; No. 9; pp. 812–816; 1971.
Arieh Kampf, et al.; Journal of Medicinal Chemistry; vol. 19; No. 7; pp. 909–915; 1976.
A. Kampf and Mathias P. Mertes; Nucleic Acid Chemistry; vol. 1; pp. 355–357; 1978.
K. Ogilvie et al. Can. J. Chem., 58, 2686 (1980).
A. Szemzo, et al.; J. Carbohydrates Nucleosides Nucleotides; vol. 7 (6); pp. 365–379; 1980.
Philip J. Barr et al., J. Chem. Soc., Perkin Trans 1 Organic and Bio–Organic Chemistry (1972–1999) pp. 1665–1670 (1981).
J. Dellaria et al., syn. Comm., 16(9), 10433–1048 (1986).

T. L. Su et al., J. Med. Chem. 29, 151–154, (1986).
L. Banfi et al., Tetrahedron, 43(10), 2317–2322(1987).
Jai–Tung Huang, et al.; Nucleic Acids Symposium Series; vol. 18; pp. 261–264; 1987.
P. Stoss et al.., Nucleosides and Nucleotides, 7(2), 213–225, (1988).
S. Yamakage et al., Tetrahedron Letters, 30(46), 6361–6364, (1989).
Masaki Matsui, et al.; J. Org. Chem.; vol. 55; pp. 1396–1399; 1990.
A. Barrett et al., J. Org. Chem., 55, 3853–3857 (1990).
S. Iwai et al., Tetrahedron, 46(19), 6673–6688 (1990).
Yoshifumi Watanabe, et al.; Chem. Pharm. Bull.; vol. 38 (10); pp. 2726–2732; 1990.
Theodora W. Greene, et al., Protective Groups in Org. Syn. , Second Edition, John Wiley and Sons, New York, pp. 68–87 (1991).
Biswajit Das and Nitya G. Kundu; J. Chem. Res. Synopses; vol. 11; pp. 364–365; 1992.
A. G. Meyers et al., J. Am. Chem. Soc., 116,4697–4718(1994).
B. Bejer et al., Nucleosides and Nucleotides, 13(9), 1905–1927 (1994).
Sreenivasulu Megati, et al.; Bioorganic & Medicinal Chemistry Letters; vol. 4; No. 3; pp. 469–472; 1994.
H. S. Park et al., Tetrahedron Letters, 36(10), 1673–74(1995).
K. Felczak et al., J. Med. Chem., 39(8), 1720–8(1996).
Ken–Ichiro Imamura and Yoshinori Yamamoto; Bull. Chem. Soc. Jpn.; vol. 70; pp. 3103–3110; 1997.
A, Krotz et al., Nucleosides and Nucleotides, 16(7–9), 1637–1640 (1997).
K. Moriyama, et al.; Nucleic Acids Research; vol. 26; No. 9; pp. 2105–2111; (1998).
Z. Shi, Tetrahedron, 58(2002), 3287–3296.
Isono, K; Uramoto, M; Kusakabe, H.; Kimura, K.; Izaki, K.; Nelson, C.C.; McCloskey, J.A.; J. Antibiotics, 1985, 38, 1617–1621.

(List continued on next page.)

Primary Examiner—Samuel Barts
Assistant Examiner—Patrick Lewis
(74) Attorney, Agent, or Firm—Daniel B. Moran

(57) ABSTRACT

The invention provides compounds of the Formula 1

Formula 1

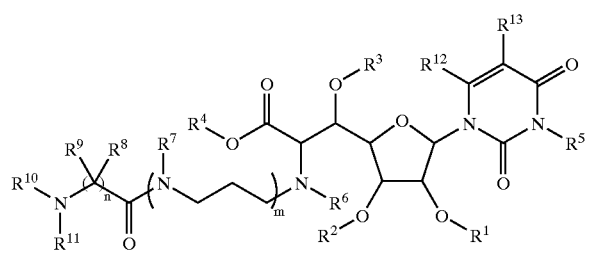

wherein the definitions of m, n, $R^1$, $R^2$, $R^3$, $R^4$, $R^5$, $R^6$, $R^7$, $R^8$, $R^9$, $R^{10}$, $R^{11}$, $R^{12}$ and $R^{13}$ are in the specification. These compounds are useful as antibacterial agents.

71 Claims, No Drawings

OTHER PUBLICATIONS

Ubukata, M.; Isono, K.; Kimura, K.; Nelson, C.C.; McCloskey, J.A.; J. Am.Chem.Soc., 1988, 110, 4416–4417.

Kimura, K.; Miyata, N.; Kawanishi, G.; Kamino, Y.; Izaki, K.; Osono, K.; Agric.Biol.Chem., 1989, 53, 1811–1815.

Kimura, K.; Ikeda, Y.; Kagami, S.; Yoshihara, M.; J. Antibiotics, 1998, 51, 1099–1044.

Ubukata, M.; Kimura, K.; Isono, K.; Nelson, C.C.; Gregson, J.M.; McClosky, J.A.; J. Org.Chem, 1992, 57, 6392–6403.

Larock, Richard C.; Comprehensive Organic Transformations, VCH Publishers, 1989, 411–415.

Myers, A.G.; Gin, D.Y.; Rogers, D.H.; J.Amer.Chem.Soc., 1994, 116, 4697–4718.

Barrett, A.G.M.; Lebold, S.A.; J.Org.Chem., 1990, 55, 3853.

Paulsen, H.; Brieden, M.; Benz, G.; Liebigs Ann. Chem., 1987, 565.

Panek, J.; J.Org.Chem., 1998, 63, 2382.

Mengin–Lecreaulx, et al; J.Bacteriol 173(15) 1991, 4625–4636.

Scolastico, C.; Tetrahedron Letts., 1987, 43, 2317.

Kimura, et al.; Sulfation of Antibiotic and its Biological Activity; Baiosaiensu to Indasutori; 1998; vol. 56; No. 5; pp. 331–332.

Kimura, et al.; Sulfation of Antibiotic and its Biological Activity, Baiosaiensu to Indasutori; 1998; vol. 56; No. 5; pp. 331–332, English Abstract.

PCT Search Report, Aug. 27, 2002; PCT/US02/13211.

* cited by examiner

ANTIBIOTIC AA 896 ANALOGS

CROSS REFERENCE TO RELATED APPLICATIONS

"This application claims priority from copending provisional applications Ser. No. 60/286,401 filed on Apr. 25, 2001, Ser. No. 60/290,139 filed on May 10, 2001, Ser. No. 60/286,297 filed Apr. 25, 2001, Ser. No. 60/290,140 filed May 10, 2001, Ser. No. 60/286,402 filed Apr. 25, 2001 and Ser. No. 60/290,156 filed May 10, 2001 the entire disclosures of which are hereby incorporated by reference."

FIELD OF THE INVENTION

The present invention relates to antibiotic AA896 analogs which have antibiotic activity.

BACKGROUND OF THE INVENTION

This invention relates to novel compounds containing 2-amino-3-[3,4-dihydoxy-5-(2,4-dioxo-3,4-dihydro-1(2H)-pyrimidinyl)tetrahydro-2-furanyl]-3-hydroxypropanoic acid ester herein called 2-amino-3-hydroxy-3-uridyl-propanoic acid ester derivative (or can be referred to as the uridyl peptide derivative) as well as their pharmaceutically acceptable salts. The compounds of this invention exhibit antibiotic activity against a wide spectrum of organisms.

This invention encompasses novel intermediates useful for preparing the novel compounds of the present invention and to novel methods for preparation of the novel compounds and the intermediate compounds. This invention also relates to non-toxic pharmaceutically acceptable salts of the novel 2-amino-3-hydroxy-3-uridyl-propanoic acid ester derivatives, pharmaceutical compositions containing the compounds, and to the method of use of the present compounds alone or in combination with other agents for the treatment of bacterial infections in humans and other animals.

DESCRIPTION OF THE PRIOR ART

The structurally related natural products, Liposidomycins A, B and C, have been isolated and their biological properties of antibacterial activity have been reported (Isono, K.; Uramoto, M.; Kusakabe, H.; Kimura, K.; Izaki, K.; Nelson, C. C.; McCloskey, J. A., *J. Antibiotics*, 1985, 38,1617–1621. Ubukata, M.; Isono, K.; Kimura, K.; Nelson, C. C.; McCloskey, J. A. *J. Am. Chem. Soc.*, 1988, 110, 4416–4417. Kimura, K.; Miyata, N.; Kawanishi, G.; Kamino, Y.; Izaki, K.; Isono, K. *Agric. Biol. Chem.*, 1989, 53,1811–1815.). Later Liposidomycins A-(I), A-(II), A-(III) and A-(IV) have been isolated to show that new Liposidomycins also have antibacterial activity (Kimura, K.; Ikeda, Y.; Kagami, S.; Yoshihara, M., *J. Antibiotics*, 1998, 51, 1099–1104. and other references herein). Detailed structural analysis of Liposidomycins A, B and C by using their chemical degradation products has been reported (Ubukata, M.; Kimura, K.; Isono, K.; Nelson, C. C.; Gregson, J. M.; McClosky, J. A., *J. Org. Chem.*, 1992, 57, 6392–6403). The structural difference of AA896 and the Liposidomycin class compounds is that the latter contains the methylated amino group at the 2-position of the 2-amino-3-hydroxylpropanoic acid core skeleton. The compounds of the Liposidomycins class have developed by Fugisawa Pharmaceutical LTD., and they have filed several patents related to the development of Liposidomycin class compounds (Patent JP05078385).

The compounds in the patent, JP05078385 are the derivatives of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1(2H)-pyrimidinyl)tetrahydro-2-furanyl] propanoic acid or the degraded products of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1(2H)-pyrimidinyl)tetrahydro-2-furanyl]-propanoic acid, and the patent, JP05078385 claim only the compounds 1n which the amino group at the 2-position of the 2-amino-3-hydroxylpropanoic acid core skeleton is consistently methylated.

The mixture of antibiotic complex AA896 (novel uridyl peptide derivatives) was produced by and isolated from cultures AA896 and it is known that these natural compounds displayed both in vitro and in vivo activity against a variety of gram-positive infection (Copending U.S. Patent Application).

The compounds of this invention are 2-amino-3-[3,4-dihydoxy-5-(2,4-dioxo-3,4-dihydro-1(2H)-pyrimidinyl) tetrahydro-2-furanyl]-3-hydroxypropanoic acid which consists a core skeleton of AA896. The compounds of this invention are suitably substituted at the amino group of the 2 position of propanoic acid with a peptide containing alkyl group and the nitrogen on the pyrimidinyl group. No compounds containing the core structure of this kind with substitution patterns exemplified in this invention have been reported.

This invention is concerned with a new series of antibiotics of AA-896.

SUMMARY OF THE INVENTION

This invention is concerned with novel 2-amino-3-[3,4-dihyoxy-5-(2,4-dioxo-3,4-dihydro-1(2H)-pyrimidinyl) tetrahydro-2-furanyl]-3-hydroxypropanoic acid derivatives (or uridyl dipeptide or dipeptido nucleoside), represented by formula I which have antibacterial activity; with methods of treating infectious diseases in humans and other animals when administering these new compounds; with pharmaceutical preparations containing these compounds; with novel intermediate compounds and regio- and stereoselective processes for the production of compounds of formula I.

Formula 1

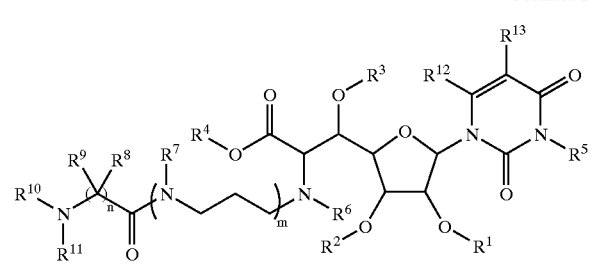

wherein:
m is an integer of 0 to 2;
n is an integer of 0 to 13;
p is an integer of 0 to 2;
q is an integer of 0 to 5;
J is F, Cl or Br;
$R^1$, $R^2$, $R^3$, and $R^4$ are independently
H;
alkyl of 1 to 10 carbon atoms optionally substituted with 1 to 3 substituents selected from the group consisting of -J, —$R^{16}$, -aryl, —$OR^{14}$, —$OR^{16}$, —$OR^{15}R^{16}$, —Oaryl, —$OR^{15}OR^{14}$, —$OCH_2OR^{16}$, —$OR^{15}OR^{15}$aryl, —OR$^{15}$Oaryl, —C(O)OR$^{14}$, —C(O)OR$^{16}$, —C(O)OR$^{15}$R$^{16}$, —C(O)R$^{14}$, —C(O)R$^{16}$, —C(O)R$^{15}$R$^{16}$, —C(O)aryl, —C(O)R$^{15}$aryl, silyl substituted with three groups independently selected from R$^{14}$, R$^{15}$, and R$^{16}$, —O-silyl substituted with three groups independently selected from R$^{14}$, R$^{15}$, and R$^{16}$;

cycloalkyl of 3 to 10 carbon atoms optionally substituted with one to three alkyl groups of 1 to 6 carbon atoms;

silyl substituted with three groups independently selected from R$^{14}$, R$^{15}$, and R$^{16}$;

—C(O)R$^{14}$, —C(O)R$^{15}$R$^{16}$, —C(O)R$^{16}$, —C(O)aryl, —C(O)R$^{15}$aryl;

allyl optionally substituted with one to three moieties independently selected from R$^{14}$, R$^{15}$ and R$^{16}$;

R$^{15}$aryl;

aryl;

R$^{14}$ is a monovalent group independently selected from alkyl of 1 to 6 carbon atoms, alkenyl of 2 to 6 carbon atoms, and alkynyl of 2 to 6 carbon atoms;

R$^{15}$ is a divalent alkyl group of 1 to 6 carbon atoms; optionally when two of R$^{15}$ are substituted on a nitrogen atom together with the nitrogen to which they are attached, form a ring selected from morpholine, piperazine or piperidine;

R$^{16}$ is aryl optionally substituted with 1 to 4 substituents selected from the group consisting of: -J, —NO$_2$, —NH$_2$, —OH, —SH, —CN, —COOH, —CONH$_2$, —NHC(O)NH$_2$, —CF$_3$, —OCF$_3$, —R$^{14}$—OR$^{14}$, —NHR$^{14}$, —NR$^{14}$R$^{14}$, —S(O)$_m$R$^{14}$, —NHSO$_2$R$^{14}$, —R$^{15}$OH, —R$^{15}$OR$^{14}$, —R$^{15}$NH$_2$, —R$^{15}$NHR$^{14}$, —R$^{15}$NR$^{14}$R$^{14}$, —R$^{15}$SH, —R$^{15}$S(O)$_m$R$^{14}$, —NHR$^{15}$OH, —NHR$^{15}$OR$^{14}$, —N(R$^{14}$)R$^{15}$OH, —N(R$^{14}$)R$^{15}$OR$^{14}$, —NHR$^{15}$NH$_2$, —NHR$^{15}$NHR$^{14}$, —NHR$^{15}$NR$^{14}$R$^{14}$, —N(R$^{14}$)R$^{15}$NH$_2$, —N(R$^{14}$)R$^{15}$NHR$^{14}$, —N(R$^{14}$)R$^{15}$NHR$^{14}$R$^{14}$, —OR$^{15}$OH, —OR$^{15}$OR$^{14}$, —NHC(O)R$^{14}$, —NHC(O)NHR$^{14}$, —OR$^{15}$C(O)R$^{14}$, —NHR$^{15}$C(O)R$^{14}$, —C(O)R$^{14}$, —C(O)R$^{14}$, —C(O)NHR$^{14}$, —C(O)NR$^{14}$R$^{14}$, —R$^{14}$C(O)R$^{14}$, —R$^{15}$C(O)OH, —R$^{15}$C(O)OR$^{14}$, —R$^{15}$C(O)NH$_2$, —R$^{15}$C(O)NHR$^{14}$, —R$^{15}$C(O)NR$^{14}$R$^{14}$, —R$^{15}$OC(O)R$^{14}$, —R$^{15}$OC(O)NH$_2$, —R$^{15}$OC(O)NHR$^{14}$ and —R$^{15}$OC(O)NR$^{14}$R$^{14}$;

aryl may optionally be substituted by —V-aryl, —V—R$^{16}$ or —V—R$^{17}$;

V is selected from C(O), C(O)O, OC(O), C(O)NH, NHC(O), NHSO$_2$, SO$_2$NH, C(OH)H, O(CR$^{18}$R$^{18}$)$_q$, S(O)$_{m''}$(CR$^{18}$R$^{18}$)$_q$, NH(CR$^{18}$R$^{18}$)$_q$, NR$^{19}$(CR$^{18}$R$^{18}$)$_q$, (CR$^{18}$R$^{18}$)$_q$, (CR$^{18}$R$^{18}$)$_q$O, (CR$^{18}$R$^{18}$)$_q$S(O)$_{m''}$, (CR$^{18}$R$^{18}$)$_q$NH, (CR$^{18}$R$^{18}$)$_q$NR$^{15}$, alkenyl of 2 to 6 carbon atoms, alkynyl of 2 to 6 carbon atoms and cycloalkyl of 3 to 10 carbon atoms;

R$^{17}$ is cycloalkyl of 3 to 7 carbon atoms optionally substituted with one or more alkyl groups of 1 to 6 carbon atoms or R$^{14}$;

R$^{18}$ is independently H or R$^{14}$;

R$^5$, R$^6$, R$^7$ and R$^{10}$ are independently

H;

alkyl of 1 to 10 carbon atoms optionally substituted with 1 to 3 substituents selected from the group consisting of -J, —R$^6$, -aryl, —OR$^4$, —OR$^6$, —OR$^{15}$R$^{16}$, —Oaryl, —OR$^{15}$OR$^{14}$, —OCH$_2$OR$^{16}$, —OR$^{15}$OR$^{15}$aryl, —OR$^{15O}$aryl, —C(O)OR$^{14}$, —C(O)OR$^{16}$, —C(O)OR$^{15}$R$^{16}$, —C(O)Oaryl, —C(O)OR$^{15}$aryl, —C(O)R$^{14}$, —C(O)R$^{16}$, —C(O)R$^{15}$R$^{16}$, —C(O)aryl, —C(O)R$^{15}$aryl, silyl substituted with three groups independently selected from R$^{14}$, R$^{15}$, and R$^{16}$, —O-silyl substituted with three groups independently selected from R$^{14}$, R$^{15}$, and R$^{16}$;

cycloalkyl of 3 to 10 carbon atoms optionally substituted with one to three alkyl groups of 1 to 6 carbon atoms;

—C(O)R$^{14}$, —C(O)R$^{15}$R$^{16}$, —C(O)R$^{16}$, —C(O)aryl, or —C(O)R$^{15}$aryl;

—C(O)OR$^{14}$, —C(O)OR$^{15}$R$^{16}$, or —C(O)OR$^{16}$;

allyl optionally substituted with one to three groups independently selected from R$^{14}$, R$^{15}$, and R$^{16}$;

R$^{15}$aryl;

aryl;

R$^8$, R$^9$ are independently

H;

alkyl of 1 to 10 carbon atoms optionally substituted with 1 to 3 substituents selected from the group consisting of —R$^{16}$, —OH, —C(O)OH, CONH$_2$, —NHC(O)NH$_2$, —OR$^{14}$, —OR$^{16}$, —OR$^{15}$R$^{16}$, —Oaryl, —OR$^{15}$aryl, —OR$^{15}$OR$^{14}$, —OR$^{15}$OR$^{16}$, —OR$^{15}$OR$^{15}$R$^{16}$, —OR$^{15}$OR$^{15}$aryl, —OR$^{15}$Oaryl, —C(O)OR$^{14}$, —C(O)OR$^{16}$, —C(O)OR$^{15}$R$^{16}$—C(O)Oaryl, —C(O)OR$^{15}$aryl, —C(O)R$^{14}$, —C(O)R$^{16}$, —C(O)R$^{15}$R$^{16}$, —C(O)aryl, —C(O)R$^{15}$aryl, —S(O)pR$^{14}$, —S(O)pR$^{16}$, —S(O)pR$^{15}$R$^{16}$, —S(O)paryl, —S(O)pR$^{15}$aryl, C(O)aryl, —C(O)R$^{15}$aryl, —S(O)pR$^{14}$, —S(O)pR$^{16}$, —S(O)pR$^{15}$R$^{16}$, —S(O)paryl, —S(O)pR$^{15}$aryl, NHC(=NH)NH$_2$, —NHC(=NH)NH(NO$_2$), —N-optionally substituted with three groups independently selected from R$^{14}$, R$^{15}$, and R$^{16}$, silyl substituted with three groups independently selected from R$^{14}$, R$^{15}$, and R$^{16}$, —O-silyl substituted with three groups independently selected from R$^{14}$, R$^{15}$, and R$^{16}$;

allyl optionally substituted with one to three groups independently selected from R$^{14}$, R$^{15}$, and R$^{16}$;

aryl;

cycloalkyl group of 3 to 10 carbon atoms, which may be optionally substituted with one or more alkyl groups of 1 to 6 carbon atoms;

R$^{11}$ is independently

H;

alkyl of 1 to 10 carbon atoms optionally substituted with 1 to 3 substituents selected from the group consisting of -J, —R$^{16}$, -aryl, —OR$^{14}$, —OR$^{16}$, —OR$^{15}$R$^{16}$, —Oaryl —OR$^{15}$OR$^{14}$, —OCH$_2$OR$^{16}$, —OR$^{15}$OR$^{15}$aryl, —OR$^{15}$Oaryl, —C(O)OR$^{14}$, —C(O)OR$^{16}$, —C(O)OR$^{15}$R$^{16}$, —C(O)Oaryl, —C(O)OR$^{15}$aryl, —C(O)R$^{14}$, —C(O)R$^{16}$, —C(O)R$^{15}$R$^{16}$, —C(O)aryl, —C(O)R$^{15}$aryl, —N-optionally substituted with three groups independently selected from R$^{14}$, R$^{15}$, and R$^{16}$, -silyl substituted with three groups independently selected from R$^{14}$, R$^{15}$, and R$^{16}$, —O-silyl substituted with three groups independently selected from R$^{14}$, R$^{15}$, and R$^{16}$;

—C(O)(CR$^{19}$R$^{20}$)NHC(O)NH(CR$^{21}$R$^{22}$)COOR$^{23}$;

cycloalkyl of 3 to 10 carbon atoms optionally substituted with one to three alkyl groups of 1 to 6 carbon atoms;

—C(O)R$^{14}$, —C(O)R$^{15}$R$^{16}$, —C(O)R$^{16}$, —C(O)aryl, —C(O)R$^{15}$aryl;

allyl optionally substituted with one to three groups independently selected from R$^{14}$, R$^{15}$, and R$^{16}$;

R$^{15}$aryl;

aryl;

R$^{19}$, R$^{20}$, R$^{21}$ and R$^{22}$ are independently

H;

alkyl of 1 to 10 carbon atoms optionally substituted with 1 to 3 substituents selected from the group consisting of —R$^{16}$, —OH, —C(O)OH, CONH$_2$, —NHC(O)NH$_2$, —OR$^{14}$, —OR$^{16}$, —OR$^{15}$R$^{16}$, —Oaryl, —OR$^{15}$aryl, —OR$^{15}$OR$^{14}$, —OR$^{15}$OR$^{16}$, —OR$^{15}$OR$^{15}$R$^{16}$, —OR$^{15}$OR$^{15}$aryl, —OR$^{15}$Oaryl, —C(O)OR$^{14}$, —C(O)OR$^{16}$, —C(O)OR$^{15}$R$^{16}$, —C(O)Oaryl, —C(O)OR$^{15}$aryl, —C(O)R$^{14}$, —C(O)R$^{16}$, —C(O)R$^{15}$R$^{16}$, —C(O)aryl, —C(O)R$^{15}$aryl, —S(O)pR$^{14}$, —S(O)pR$^{16}$, —S(O)

pR$^{15}$R$^{16}$, —S(O)paryl, —S(O)pR$^{15}$aryl, NHC(=NH)
NH$_2$, —NHC(=NH)NH(NO$_2$), —N-optionally substituted with three groups independently selected from R$^{14}$, R$^{15}$, and R$^{16}$, silyl substituted with three groups independently selected from R$^{14}$, R$^{15}$, and R$^{16}$, —O-silyl substituted with three groups independently selected from R$^{14}$, R$^{15}$, and R$^{16}$;

allyl optionally substituted with one to three groups independently selected from R$^{14}$, R$^{15}$, and R$^{16}$;

aryl;

cycloalkyl group of 3 to 10 carbon atoms, which may be optionally substituted with one or more alkyl groups of 1 to 6 carbon atoms;

R$^{23}$ is

H;

alkyl of 1 to 10 carbon atoms optionally substituted with 1 to 3 substituents selected from the group consisting of -J, —R$^{16}$, -aryl, —OR$^{14}$, —OR$^{16}$, —OR$^{15}$R$^{16}$, —Oaryl, —OR$^{15}$OR$^{14}$, —OCH$_2$OR$^{16}$, —OR$^{15}$R$^{15}$aryl, —OR$^{15}$Oaryl, —C(O)OR$^{14}$, —C(O)OR$^{16}$, —C(O)OR$^{15}$R$^{16}$, —C(O)Oaryl, —C(O)OR$^{15}$aryl, —C(O)R$^{14}$, —C(O)R$^{16}$, —C(O)R$^{15}$R$^{16}$, —C(O)aryl, —C(O)R$^{15}$aryl;

silyl substituted with three groups independently selected from R$^{14}$, R$^{15}$, and R$^{16}$;

cycloalkyl of 3 to 10 carbon atoms optionally substituted with one to three alkyl groups of 1 to 6 carbon atoms; —C(O)R$^{14}$, —C(O)R$^{15}$R$^{16}$, —C(O)R$^{16}$, —C(O)aryl, —C(O)R$^{15}$aryl;

allyl optionally substituted with one to three groups independently selected from R$^{14}$, R$^{15}$, and R$^{16}$;

R$^{15}$aryl;

aryl;

R$^{12}$ and R$^{13}$ are independently

H;

F;

an alkyl group of 1 to 10 carbon atoms including their branches;

allyl optionally substituted with one to three groups independently selected from R$^{14}$, R$^{15}$, and R$^{16}$;

aryl;

or a pharmaceutically acceptable salt thereof.

Among the preferred embodiments of this invention including pharmaceutically acceptable salts thereof are those in the subgroups below, wherein other variables are as defined above:

a. R$^3$, R$^{12}$ and R$^{13}$ are H;
   m is 1 or 2;
   R$^1$ and R$^2$ are silyl substituted with three groups independently selected from R$^{14}$, R$^{15}$, and R$^{16}$;

b. R$^3$, R$^6$, R$^7$, R$^{12}$ and R$^{13}$ are H;
   m is 1 or 2;
   R$^1$ and R$^2$ are silyl substituted with three groups independently selected from R$^{14}$, R$^{15}$, and R$^{16}$;

c. R$^1$, R$^2$, R$^3$, R$^{12}$ and R$^{13}$ are H;
   m is 1 or 2;

d. R$^1$, R$^2$, R$^3$, R$^6$, R$^7$, R$^{12}$ and R$^{13}$ are H;
   m is 1 or 2;

e. R$^3$, R$^{12}$ and R$^{13}$ are H;
   m is 1 or 2;
   R$^1$ and R$^2$ are —C(O)R$^{14}$, —C(O)R$^{15}$R$^{16}$, —C(O)R$^{16}$, —C(O)aryl, —C(O)R$^{15}$aryl; and f. R$^3$, R$^6$, R$^7$, R$^{12}$ and R$^{13}$ are H;
   m is 1 or 2;
   R$^1$ and R$^2$ are —C(O)R$^{14}$, —C(O)R$^{15}$R$^{16}$, —C(O)R$^{16}$, —C(O)aryl, or —C(O)R$^{15}$aryl.

Specifically preferred compounds of the invention are the following compounds or pharmaceutically acceptable salts thereof.

tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate, tert-Butyl (2S,3R)-2-[(3-{[(2S,3S)-2-amino-3-hydroxy-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (5R, 12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate, tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate, tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (5S,12S)-12-[(R)-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate, tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl]-3-hydroxypropanoate, tert-Butyl (5S,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate, tert-Butyl (2S,3S)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate, tert-Butyl (2S,3R)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (5S,12S)-5-benzyl-12-[(R)-[(3R,4R,5R)-3,4-bis{[tertbutyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate, tert-Butyl (2S,3R)-2-[(3-{[(2S)-2-amino-3-phenylpropanoyl]amino}propyl)amino]-3-[(3R,4R,5R)-3,4-bis{[tert-butyl(dimethyl)silyl]oxy}-5-(3-(4- methoxybenzyl)-2,4-dioxo-3,4-dihydro-1(2H)-pyrimidinyl)tetrahydro-2-furanyl]-3-hydroxypropanoate, tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-methyl-3,6-dioxo-1-phenyl-2-oxa-4,7,11-triazatridecan-13-oate, tert-Butyl (2S,3R)-2-[(3-{[(2S)-2-aminopropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (5S,12S)-5-[2-(benzyloxy)-2-oxoethyl]-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate, (3S)-3-Amino-4-[(3-{[(1S,2S)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-4-oxobutanoic acid, tert-Butyl (9S,16S)-9-{[(benzyloxy)carbonyl]amino}-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,10-dioxo-1-phenyl-2-oxa-4,11,15-triazaheptadecan-17-oate, tert-Butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(3-{[(2S)-2,6-diaminohexanoyl]amino}propyl)amino]-3-hydroxypropanoate, tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[3-(tert-butoxy)-3-oxopropyl]-3,6-dioxo-1-phenyl-2-oxa-4,7,11-triazatridecan-13-oate, tert-Butyl (4S)-4-amino-5-[(3-{[(1S,2R)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-5-oxopentanoate, tert-Butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(11-{[(9H-fluoren-9-ylmethoxy)carbonyl]amino}undecanoyl)-amino]-3-hydroxypropanoate, tert-Butyl (2S,3R)-2-[(11-aminoundecanoyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, tert-Butyl (21S)-21-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-1-(9H-fluoren-9-yl)-3,15-dioxo-2-oxa-4,16,20-triazadocosan-22-oate, tert-Butyl (2S,3R)-2-({3-[(11-aminoundecanoyl)amino]propyl}amino)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxy-2-methylpropyl]-2-isopropyl-4,7,10-trioxo-3,5,8,11,15-pentaazaheptadecane-1,17-dioate, (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-19,19-dimethyl-4,7,10,17-tetraoxo-18-oxa-3,5,8,11,15-pentaazaicosan-1-oic acid, 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate, (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-19,19-dimethyl-4,7,10,17-tetraoxo-18-oxa-3,5,8,11,15-pentaazaicosan-1-oic acid, 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxyethyl]-2-isopropyl-4,7,10-trioxo-3,5,8,11,15-pentaazaheptadecane-1,17-dioate, Ethyl (5S)-12-[(R)-[(2R,3R,4R,5S)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate, Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate, Ethyl (3R)-2-[(3-{[(2S,3S)-2-amino-3-hydroxybutanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]-3-hydroxypropanoate, Ethyl (3R)-2-[(3-{[(2S,3S)-2-amino-3-hydroxybutanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate, 16-Benzyl 2-ethyl (1R,9S,12S,16S)-1-[(2R,3R,4R,5S)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate, 16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate, Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate, 16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-hydroxy-2-methylpropyl]-17-methyl-8,11,14-trioxo-3,7,10,13,15-pentaazaoctadecane-2,16-dicarboxylate, Ethyl (5S)-12-{(R)-(acetyloxy)[(2R,3R,4R,5S)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate, Ethyl (5S)-12-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate, Ethyl (3R)-3-(acetyloxy)-2-[(3-{[(2S)-2-amino-4-methylpentanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]propanoate, Ethyl (3R)-3-(acetyloxy)-2-[(3-{[(2S)-2-amino-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]propanoate, 19-Benzyl 5-ethyl (4R,12S,15S,19S)-4-[(2R,3R,4R,5S)-3,4-bis(acetyloxy)-5-(2,4-dioxo-3,4-dihydro-1(2H)-pyrimidinyl)tetrahydro-2-furanyl]-15-(3-{[(2,2-dioxido-2lambda~1~-diazanyl)(imino)methyl]amino}propyl)-12-isobutyl-20-methyl-2,11,14,17-tetraoxo-3-oxa-6,10,13,16,18-pentaazahenicosane-5,19-dicarboxylate, 1-Benzyl 17-ethyl (2S,6S,9S)-16-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate, (2S,6S,9S)-6-(3-{[Amino(imino)methyl]amino}propyl)-16-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-4,7,10,17-tetraoxo-18-oxa-3,5,8,11,15-pentaazaicosan-1-oic acid, tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate, tert-Butyl (2S,3R)-2-[(3-{[(2S,3S)-2-amino-3-hydroxybutanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)-tetrahydro-2-furanyl]-3-hydroxypropanoate, (5S,12S)-12-[(R)-[(3R,4R,5R)-4-{[tert-butyl(dimethyl)silyl]oxy}-3-hydroxy-5-(3-(4-methoxy-benzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,10-triazatridecan-13-oic acid, (4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)(imino)methyl]amino}propyl)-11-[(1S)-1-hydroxyethyl]-4-isopropyl-3,6,9,12-tetraoxo-1-phenyl-2-oxa-5,7,10,13,17-pentaazanonadecan-19-oic acid, (2S,3R)-2-[(3-{[(2S,3S)-2-Amino-3-hydroxybutanoyl]amino}propyl)amino]-3-{(3R,4R,5R)-4-{[tert-butyl(dimethyl)silyl]oxy}-5-[3-(4-methoxybenzyl)-2,4-dioxo-3,4-dihydropyrimidin-1(2H)-yl]tetrahydrofuran-2-yl}-3-hydroxypropanoic acid, (4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)(imino)methyl]amino}propyl)-11-isopropyl-4-isopropyl-3,6,9,12-tetraoxo-1-phenyl-2-oxa-5,7,10,13,17-pentaazanonadecan-19-oic acid, (2S,6S,9S,16S)-6-(3-{[Amino(imino)methyl]amino}propyl)-16-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)-methyl]-9-isobutyl-2-isopropyl-4,7,10-trioxo-3,5,8,11,15-pentaazaheptadecane-1,17-dioic acid, tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate, (5S,12S)-12-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oic acid, (2S,3R)-2-[(3-{[(2S)-2-Amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoic acid, tert-Butyl (2S,3R)-2-[(3-{[(2S)-2-amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoate, (5S,12S)-12-[(R)-[(3S,4R,5R)-5-(2,4-Dioxo-3,4-dihydro-1(2H)-pyrimidinyl)-3,4-dihydroxy-tetrahydro-2-furanyl](hydroxy)methyl]-5-isobutyl-3,6-dioxo-1-phenyl-2-oxa-4,7,11-triazatridecan-13-oic acid, tert-Butyl (5R,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate, tert-Butyl (2S,3R)-2-[(3-{[(2R)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate, and Ethyl (5S)-12-[(R)-[(2R,3R,4R,5R)-3,4-bis(acetyloxy)-5-(2,4-dioxo-3,4-dihydropyrimidin-1(2H)-yl)tetrahydrofuran-2-yl](hydroxy)methyl]-3,6-dioxo-1-phenyl-5-[(1S)-1-(tetradecanoyloxy)ethyl]-2-oxa-4,7,11-triazatridecan-13-oate.

It is understood herein that when the definition of Formula I, m, n, $R^1$, $R^2$, $R^3$, $R^4$, $R^5$, $R^6$, $R^7$, $R^8$, $R^9$, $R^{10}$, $R^{11}$, $R^{12}$ and $R^{13}$ defined above and below contain asymmetric carbons, that they encompass all possible stereoisomers and mixtures thereof discussed below. In particular, the definitions encompass any optical isomers and diastereomers; as well as the racemic and resolved, enantiomerically pure R and S stereoisomers; as well as other mixtures of the R and S stereoisomers and pharmaceutically acceptable salts thereof. Optical isomers may be obtained in pure form by standard separation techniques.

It is also understood herein that the definitions of m, n, $R^1$, $R^2$, $R^3$, $R^4$, $R^5$, $R^6$, $R^7$, $R^8$, $R^9$, $R^{10}$, $R^{11}$, $R^{12}$ and $R^{13}$ of the compounds of Formula I, above and below, encompass all possible regioisomers and mixtures thereof discussed below. Such regioisomers may be obtained pure by standard separation methods known to those skilled in the art.

For the compounds of the invention defined above and referred to herein, unless otherwise noted, the following terms are defined:

Alkyl as used herein means a branched or straight chain radical having from 1 to 10 (preferably 1 to 6) carbon atoms optionally substituted with one or more groups. Exemplary alkyl groups include but are not limited to methyl, ethyl, propyl, isopropyl, butyl, isobutyl, t-butyl, pentyl and hexyl, also optionally substituted, as well as perfluoroalkyl.

Cycloalkyl as used herein means a saturated monocyclic or polycyclic fused, bridged, or spirocyclic ring system having from 3 to 20 carbon atoms. Exemplary cycloalkyl rings include but are not limited to cyclopropyl, cyclobutyl, cyclopentyl, cyclohexyl, [2.2.1]-bicycloheptanyl, [2.2.2]-bicyclooctanyl, adamantyl, [3.3.1]-bicyclononanyl, spiro-[4.4]-nonanyl, spiro-[4.5]-decanyl, spiro-[5.5]-undecanyl, and the like.

Aryl as used herein means a homocyclic or polycyclic aromatic radical, fused or catenated, having 6 to 20 carbon atoms independently substituted with one to three substituents selected from the group of alkyl, halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, or heteroaryl. Examples include, but are not limited to, phenyl, biphenyl, naphthyl, fluorenyl, and anthracenyl, optionally substituted with one to three substituents.

Alkenyl as used herein means a branched or straight chain having from 2 to 6 carbon atoms, the chain containing at least one carbon-carbon double bond and all possible configurational isomers. Alkenyl, may be used synonymously with the term olefin and includes alkylidenes. Exemplary alkenyl groups include ethenyl, propenyl, 1,4-butadienyl, 3-hexen-1-yl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

An alkynyl group is defined as straight or branched carbon chain of 2 to 6 carbon atoms that contains at least one carbon-carbon triple bond and includes propynyl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

Some of the compounds of the invention have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography. Optically active isomers may be prepared, for example, by resolving racemic derivatives or by asymmetric synthesis. The resolution can be carried out by the methods known to those skilled in the art such as in the presence of a resolving agent, by chromatography, or combinations thereof.

The compounds of Formula (I) may be obtained as inorganic or organic salts using methods known to those skilled in the art (Richard C. Larock, Comprehensive Organic Transformations, VCH publishers, 411–415, 1989). It is well known to one skilled in the art that an appropriate salt form is chosen based on physical and chemical stability, flowability, hydroscopicity and solubility.

Pharmaceutically acceptable salts of the compounds of Formula (I) with an acidic moiety may be formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be formed from organic and inorganic acids. For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

DESCRIPTION OF THE PREFERRED EMBODIMENTS

The compounds of this invention were prepared according to the following schemes: (1) from commercially available starting materials or: (2) from known starting materials which can be prepared as described in literature procedures or: (3) from new intermediates described in the schemes and experimental procedures. Optically active isomers may be prepared, for example, by resolving racemic derivatives or by asymmetric synthesis. The resolution can be carried out by methods known to those skilled in the art such as in the presence of resolving agents, by chromatography, or combinations thereof. Reactions were carried out under inert atmosphere.

Formula 1

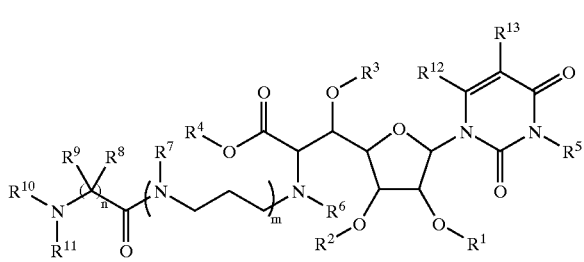

The preparation of the compounds and intermediates of this invention encompassed by formula I is described as follows, where $R^1$, $R^2$, $R^3$, $R^4$, $R^5$, $R^6$, $R^7$, $R^8$, $R^9$, $R^{10}$, $R^{11}$, $R^{12}$, $R^{13}$, m and n are herein before defined.

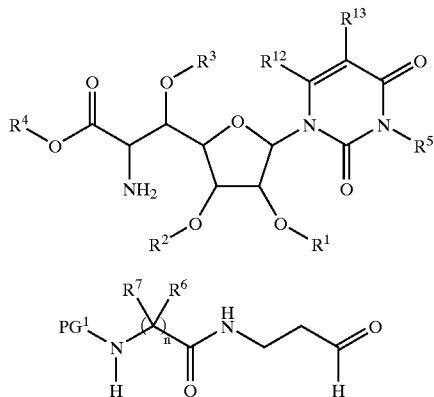

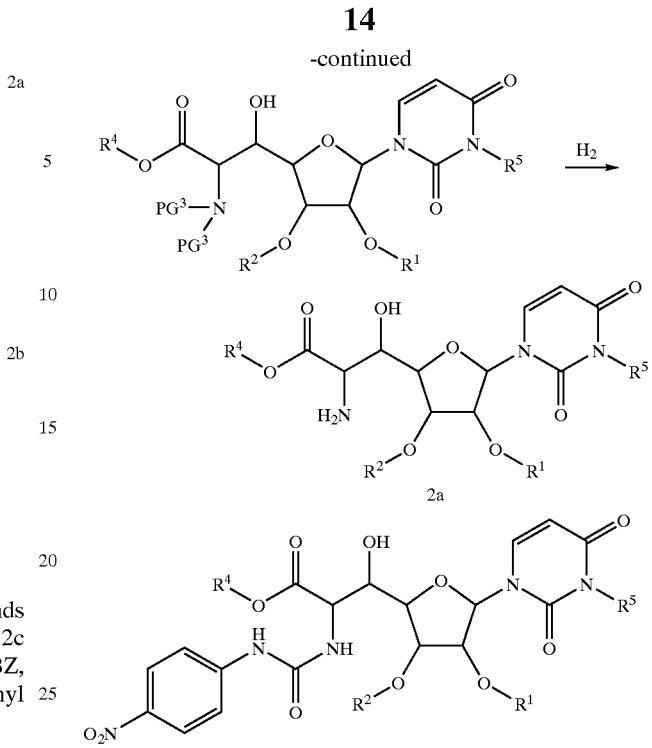

The key intermediates for the preparation of compounds of formula I are compounds of formula 2a, 2b and 2c wherein PG designates a protecting group preferably CBZ, Bn, or NO$_2$, where CBZ designates a benzyloxycarbonyl group, and Bn designates a benzyl group.

Scheme 1

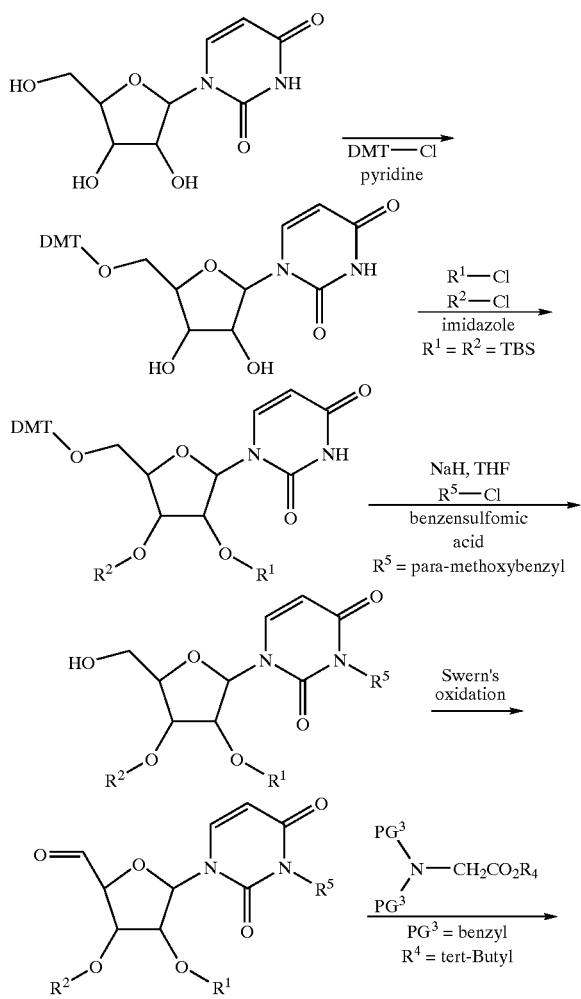

Scheme 1 shows a route for the preparation of compound of formula 2a. By using the literature known procedures (Myers, A. G.; Gin, D. Y.; Rogers, D. H., *J. Amer. Chem. Soc.*, 1994, 116, 4697–4718), a primary alcohol of commercially available uridine is protected by treatment with an agent such as 4,4'-dimethoxytrityl chloride at room temperature in an anhydrous solvent such as anhydrous tetrahydrofuran, followed by treatment with a silylating agent such as trialkylsilyl chloride, alkylarylsilyl chloride or triarylsilyl chloride to protect two secondary alcohols at the 2- and 3-positions to form the disilyl ether. tert-Butyldimethylsilyl chloride is chosen to provide stable silyl ethers, 1-[5-[Bis-(4-methoxy-phenyl)-phenyl-methoxymethyl]-3,4-bis-(tert-butyl-dimethyl-silanyloxy)-tetrahydro-furan-2-yl]-1H-pyrimidine-2,4-dione. The nitrogen of the uracil is protected with an agent such as para-methoxybenzyl chloride or benzyloxymethyl chloride at low temperature such as 0° C., and the protecting group of the primary alcohol is removed by treatment with an acid such as benzenesulfonic acid at low temperature such as 0° C., to provide an alcohol, 1-[(2R,3R,4R,5R)-3,4-bis{[tert-Butyl(dimethyl)silyl]oxy}-5-(hydroxymethyl)tetrahydro-2-furanyl]-3-(4-methoxybenzyl)-2,4(1H,3H)-pyrimidinedione. Treatment of the primary alcohol with an oxidation condition such as swern's condition [dimethylsulfoxide, oxalyl chloride, triethylamine, methylene chloride] provides the corresponding aldehyde. Reaction of the aldehyde with an anion of N,N-diprotected glycine ester such as tert-butyl 2-(dibenzylamino)-propanoate which is derived by treatment with lithium diisopropylamide in an anhydrous solvent such as tetrahydrofuran at low temperature such as −78° C. to −30° C. provides a mixture of two diastereomers of tert-butyl 3-[3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-2-(dibenzylamino)-3-hydroxy-propanoate. Two diasteroisomers can be separated by routine chromatography using silica gel flash column. The protecting groups PG$_1$ and PG$_2$ of each diastereomer such as benzyl groups can be removed by catalytic hydrogenation using a catalyst such as 5–10% palladium on carbon or 10% palladium hydroxide in a solvent such as methanol or ethanol under hydrogen atmosphere, to provide the corresponding free amine of compound of formula 2a. The absolute configration of each diastereomer is determined by X-ray analysis of the para-nitrophenylurea derivative of each diasteromer as (1R,2R,3R,4R,5R,6S) and (1R,2R,3R,4R,5S,6S).

1990, 55, 3853), commercially available D-ribose is first protected at the 1, 2 and 3 hydroxyl groups with a various alkyl group such as methyl, isopropylidine groups. The C-5 hydroxyl of ribose is then oxidized to the corresponding aldehyde by means of oxidation condition such as Swern's conditions as described in the literature (Barrett, A. G. M, Lebold, S. A., J. Org. Chem., 1990, 55, 3853). The resulting aldehyde is reacted with an anion of a protected glycine ester Scheme 2

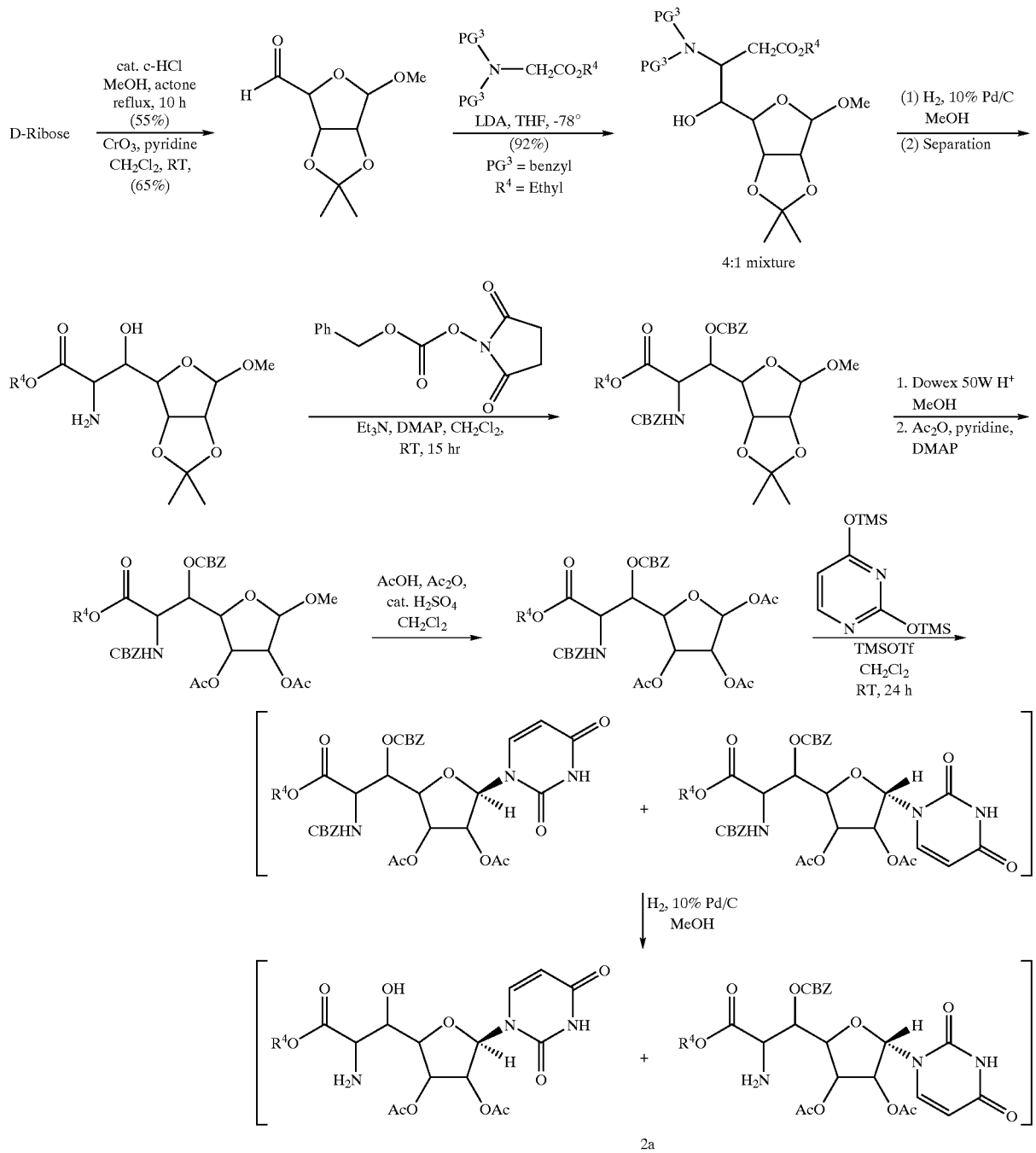

Alternative routes to synthesize the compound of formula 2a is outlined in Scheme 2 and 3. Using the literature known procedure (Barrett, A. G. M, Lebold, S. A., *J. Org. Chem.*, such as dibenzyl glycine ethyl ester by treatment of dibenzyl glycine ester with a base such as lithium diisopropylamide in a solvent such as tetrahydrofuran at low temperasture such as −78° C. under inert atmosphere, to form a inseparable mixture of two diastereomers. Removal of the amine protection such as dibenzyl group, with a condition such as catalytic hydrogenation gives a mixture of the free amines, which can be separated by the routine chromatography to give optically pure diasteromers. The absolute stereochemistry of both diastereomers can be determined by various methods, such as $^1$H-NMR studies, their Cotton effects etc. One of the diastereomer is obtained as crystalline form, and its absolute configuration is determined by X-ray analysis. Using the diastereomer which structure is confirmed, both the amine and the alcohol groups of the pure diastereomer are protected with an agent such as CBZ group. Cleavage of the protecting group at the C2 and C3 alcohols using an acid such as Dowex 50WH$^+$ in a solvent such as methanol followed by acylation using acylation agent system such as acetic anhydride-pyridine-dimethylaminopyridine give an diacyl intermediate. The C-1 methoxy group is converted to an acetoxy group by treatment with acid such as sulfuric acid in a solvent system such as acetic acid/acetic anhydride. Introduction of the uracil group in the C-1 position is performed with a reagent such as bis-O-(trimethylsilyl)uracil in the presence of a catalyst such as trimethylsilyl trifluoromethylsulfonate by using the standard Vorbrunggen type method (Paulsen, H.; Brieden, M.; Benz, G., *Liebigs Ann. Chem.*, 1987, 565, and other references herein). The corresponding β-uracil derivative (a major component) and the α-uracil derivative (a minor component) are formed in an ratio of 3:1, which is not separable, therefore a mixture is used for the next coupling step without further separation. Cleavage of the protection groups to free the hydroxyl and the amino group with a condition such as catalytic hydrogenation forms the compound of formula 2a.

Scheme 3

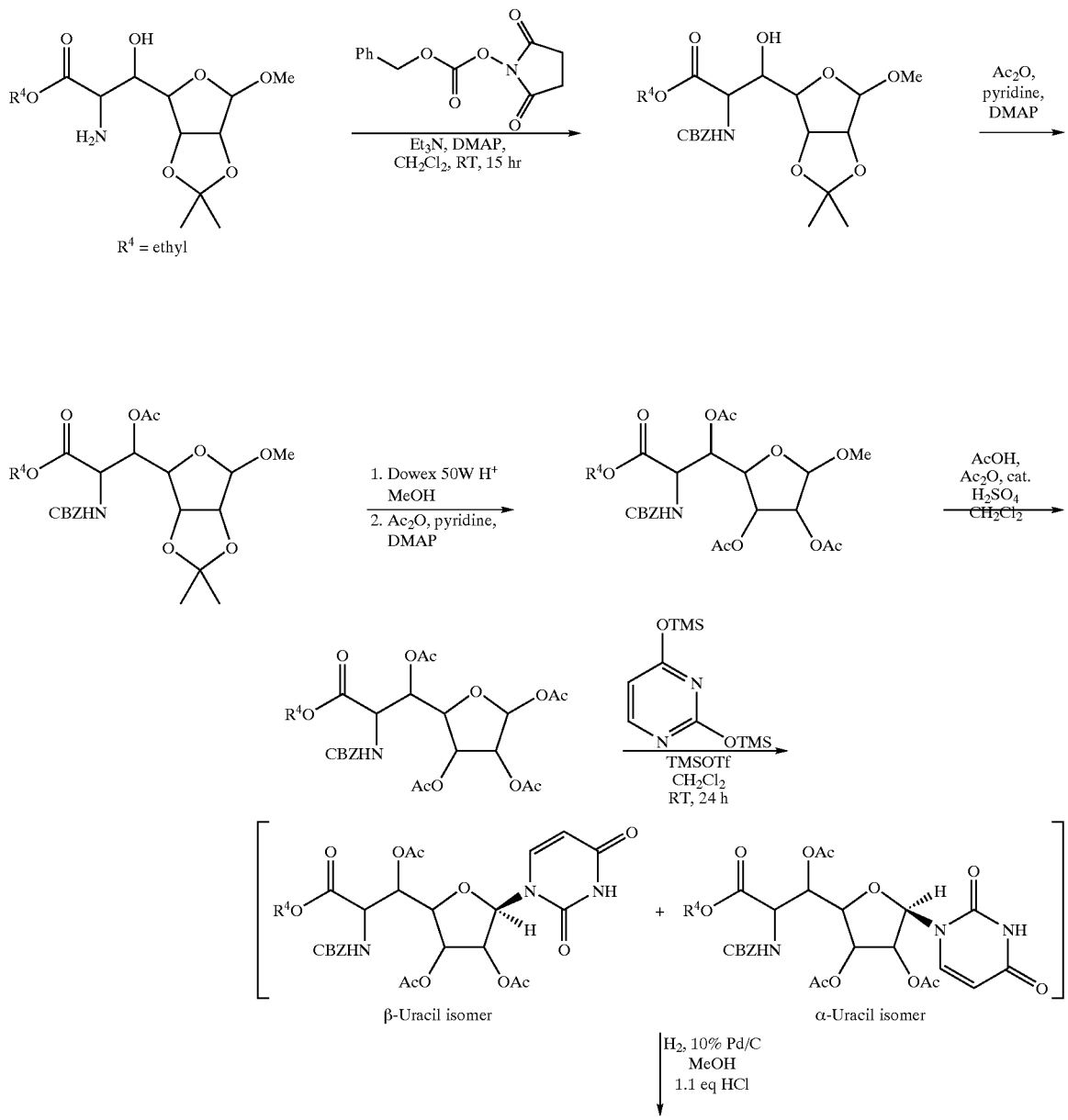

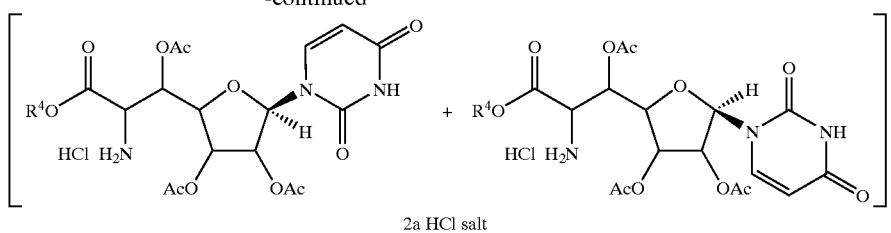

2a HCl salt

The third route for preparing the compound of formula 2a is outlined in Scheme 3 using the intermediate described in Scheme 2. The amine in the optically pure diastereomer is selectively protected with an agent such as CBZ in the presence of a catalyst such as dimethylaminopyridine in a solvent such as methylene chloride. The alcohol can be acylated under a condition such as acetc anhydride in a solvent such as dry pyridine in the presence of a catalyst such as dimethylaminopyridine, to form a fully protected intermediate. Conversion of the protecting groups at the C-2 and C-3 positions to an acyl group followed by conversion of the C-1 alkoxyl group to an acyloxy group and introduction of the uracil group can follow the conditions described in Scheme 2. Removal of the protecting group to free the amine can be performed by a condition such as catalytic hydrogenation using a catalyst such as 10% palladium on carbon in a solvent such as methanol in the presence of 1.1 equivalent of hydrogen chloride, to form the hydrogen chloride salt of the compound of formula 2a.

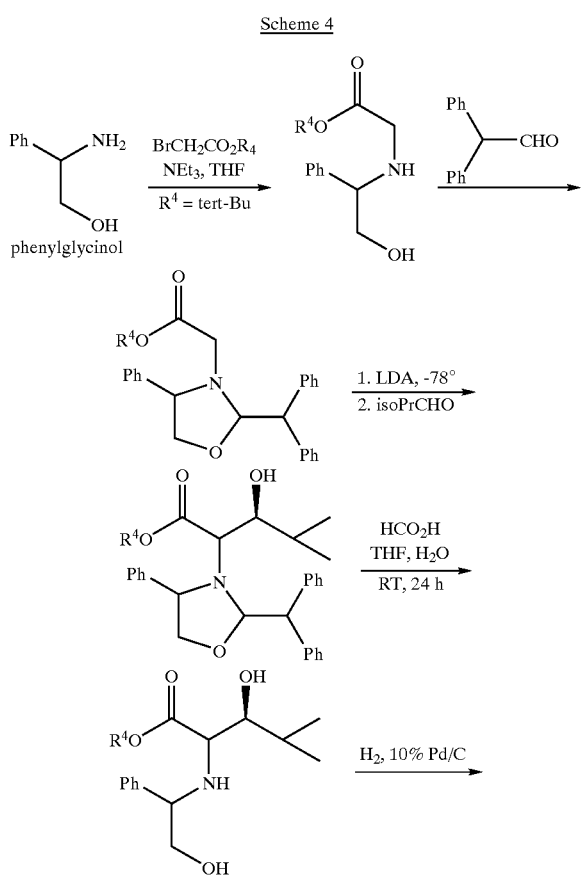

Scheme 4

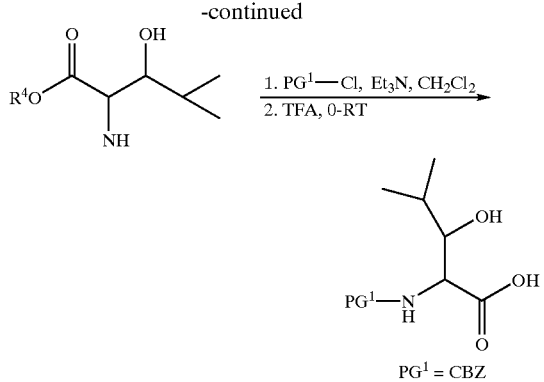

PG¹ = CBZ

Scheme 4 and 5 show routes for preparation of compound of formula 2b. The protected amino acid is either commercially available material or prepared as described in known literature. For example, the CBZ protected (2S,3S)-hydroxyleucine (CBZ: benzyloxycarbonyl) is prepared according to the analogous procedure to that described in the literature (Panek, J., J. Org. Chem., 1998, 63, 2382). As shown in scheme 4, phenylglycinol is alkylated with tert-butyl bromoacetate in the presence of base such as triethylamine in a solvent such as anhydrous tetrahydrofuran, to provide tert-butyl (2-hydroxy-1-phenyl-ethylamino)-acetate. Reaction of tert-butyl (2-hydroxy-1-phenyl-ethylamino)-acetate and diphenylacetaldehyde in the presence of a drying agent such as magnesium sulfate in a solvent such as anhydrous methylene chloride provides tert-butyl (2-benzhydryl-4-phenyl-oxazolidin-3-yl)-acetate. The oxazolidine is treated with a nucleophile such as lithium diisopropylamide in an anhydrous solvent such as anhydrous tetrahydrofuran at low temperature such as −78° C., followed by addition of an electrophile such as isopropylaldehyde, to provide tert-butyl 2-(2-benzhydryl-4-phenyl-oxazolidin-3-yl)-3-hydroxy-4-methyl-pentanoate. The oxazolidine ring is cleaved by treatment with acid such as formic acid in a solvent such as a mixture of water and tetrahydrofuran to provide tert-butyl 3-hydroxy-2-(-2-hydroxy-1-phenyl-ethylamino)-4-methyl-pentanoate. The amine is freed by hydrogenolysis using catalyst such as 5–10% palladium on carbon in a solvent such as methanol or ethanol, to provide tert-butyl 2-amino-3-hydroxy-4-methyl-pentanoate. The resulting free amine is protected by treatment with an agent such as (benzyloxycarbonyloxy)succinimide or benzyloxycarbonyl chloride in a solvent such as anhydrous methylene chloride, then the ester is cleaved by treatment with an acid such as trifluoroacetic acid to provide 2-{[(benzyloxy)carbonyl]-amino}-3-hydroxy-4-methylpentanoic acid. Optically pure compound can be prepared by using an optically pure starting material. For example, optically pure (S)-phenylglycinol provides (2S, 3S)-2-{[(benzyloxy)carbonyl]-amino}-3-hydroxy-4-methylpentanoic acid.

Scheme 5

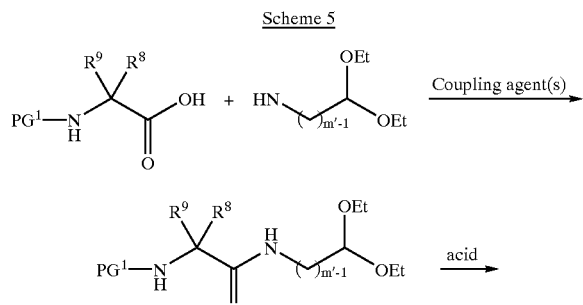

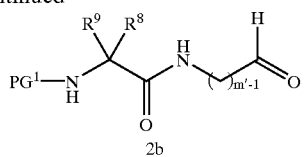

Scheme 5 shows transformation of the protected amino acid to compound of formula 2b. The protected amino acid is coupled with aminoalkyl-acetal such as commercially available 1-amino-3,3-diethoxypropane in the presence of coupling agents such as hydroxybenzotriazole and 1-(3-dimethylaminopropyl)-3-ethylcarbodiimide in a solvent such as anhydrous methylene chloride, to provide [1-(3,3-diethoxy-propylcarbamoyl)-2-hydroxy-3-methyl-butyl]-carbamic acid benzyl ester. Treatment of the acetal with an acid such as 0.5N hydrochloric acid in a solvent such as tetrahydrofuran provides the corresponding aldehyde of formula 2b.

Scheme 6

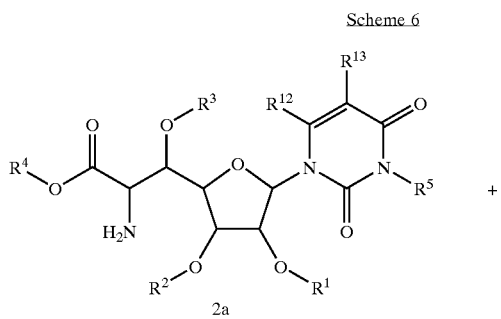

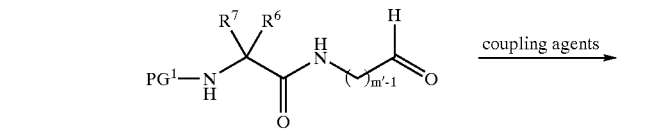

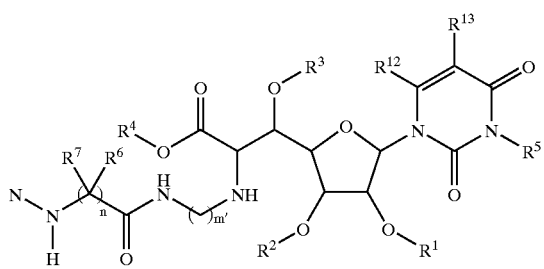

Formula 1
($R^{10} = R^{11} = H$)

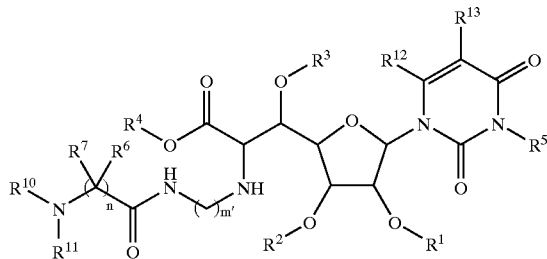

Scheme 6 shows the preparation of compound of formula I from compounds 2a and 2b. Coupling reaction between the amine of the compound of formula 2a and the aldehyde of the compound of formula 2b is carried out by a method of reductive amination in the presence of a reducing agent such as sodium triacetoxyborohydride or sodiumcyanoborohydride and an acid such as acetic acid or 1 N hydrochloric acid in a solvent such as tetrahydrofuran at ambient temperature to provide the compound of formula I in which $R^{10}$=H and $R^{11}$=$PG^3$=CBZ. The protecting group $PG^3$ (=$R^{11}$) in the compound of formula I such as a benzyloxycarbonyl group can be removed by catalytic hydrogenation using a catalyst such as 5–10% palladium on carbon or 10% palladium hydroxide in a solvent such as methanol or ethanol under hydrogen atmosphere to provide the corresponding free amine, which can be alkylated or acetylated to provide the compound of formula I.

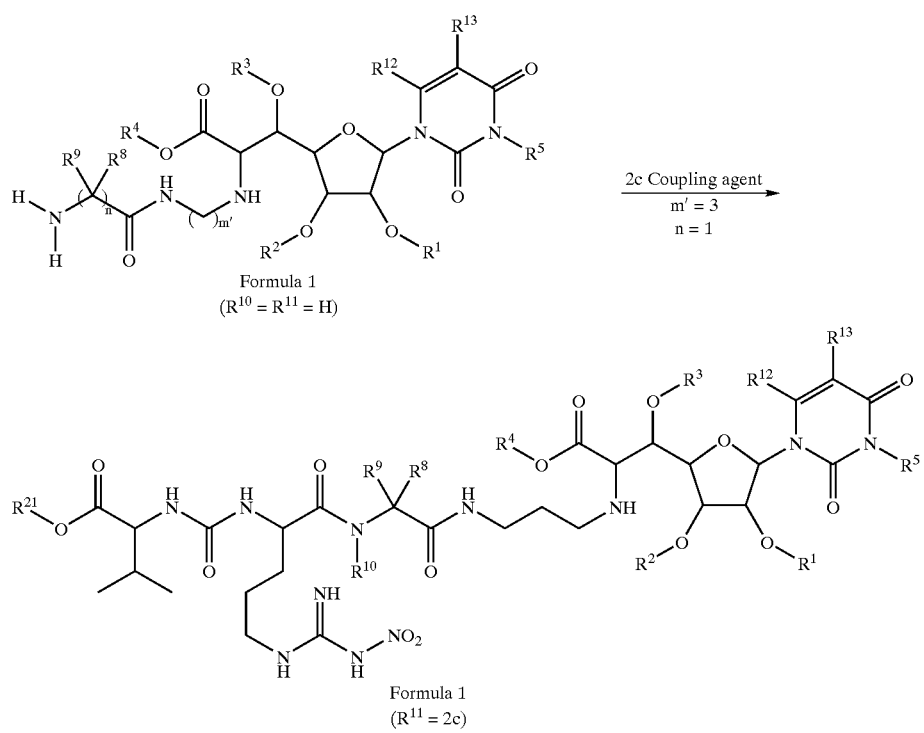

For example, the compound of formula I can be acetylated with an acetylating agent of the compound of formula 2c. As shown in scheme 7, reaction between the amino derivative ($R^{10}$=$R^{11}$=H) of the compound of formula 1a and the compound of formula 2c in the presence of a coupling agent such as 1-(3-dimethylaminopropyl)-3-ethylcarbodiimide and a catalyst such as hydroxybenzotriazole provides the acetylated compound ($R^{10}$=H, $R^{11}$=2c) of formula I.

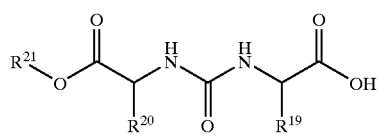

Scheme 8
-continued

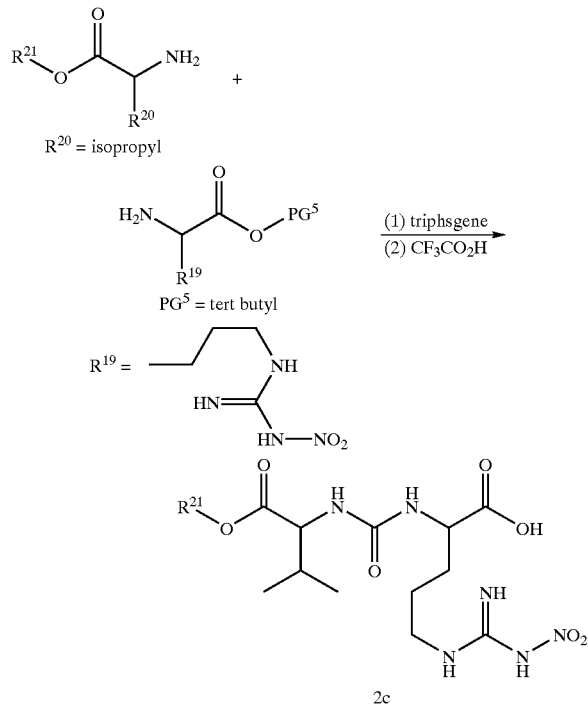

Scheme 8 shows the preparation of compound of formula 2c from two amino acid esters such as valine benzyl ester and N-nitroarginine tert butyl ester. Valine benzyl ester is commercially available material or prepared as described in known literature. The tert-butyl ester of N-nitro-arginine is prepared from commercially available $N^\square$-Fmoc-$N^g$-nitro-L-arginine in two steps: cleavage of Fmoc with a base such as piperidine followed by tert-butyl ester formation with isobutylene in the presence of a catalytic amount of acid such as concentrated sulfuric acid in a solvent such as methylene chloride at ambient temperature. Reaction between two amino acid esters, such as valine benzyl ester, tert-butyl ester of N-nitro-arginine, and a carbonylating agent such as triphosgene or carbonyldiimidazole in the presence of a base such as N,N-diisopropylethylamine or triethylamine in a solvent such as anhydrous methylene chloride under inert atmosphere provides an unsymmetrical urea such as tert-butyl 2-{[(1-[(benzyloxy)carbonyl]-2-methylpropyl}amino)carbonyl]amino}-5-{[(2,2-dioxido-2lambda~1~diazanyl)(imino)methyl]amino}pentanoate. Cleavage of the tert butyl ester with an acid such as trifluoroacetic acid in a solvent such as anhydrous methylene chloride at low temperature such as 0° C. provides the compound of formula 2c.

Selective removal of the (protecting) groups in the compound of formula I such as $R^1$, $R^2$, $R^3$, $R^4$, $R^5$, $R^{10}$, $R^{11}$, and $R^{21}$ can be achieved by using the known standard methods. When $R^1$, $R^2$, $R^3$, $R^4$, $R^5$, $R^{10}$, $R^{11}$, and $R^{21}$ in the compound of formula I are different groups, each group can be removed without changing the rest of the functional groups.

For example, when $R^1=R^2$=TBS (tert-butyldimethylsilyl) group, treatment of the compound of formula I with a reagent such as tetra-n-butylammonium fluoride in a solvent such as tetrahydrofuran gives the corresponding diol derivative of the compound of formula I, in which $R^1=R^2$=H and $R^3$, $R^4$, $R^5$, $R^{10}$, $R^{11}$, and $R^{21}$ are unchanged. When $R^{21}$=benzyl group, treatment of the compound of formula I with hydrogenation condition such as 10% palladium on carbon and hydrogen in a solvent such as methanol gives the corresponding acid of the compound of formula I, in which $R^{21}$=H and $R^1$, $R^2$, $R^3$, $R^4$, $R^5$, $R^{10}$, $R^{11}$ are unchanged. Treatment of the compound of formula I, when $R^5$=para-methoxybenzyl group, with an oxidation agent such as ceric ammonium nitrate in an solvent such as acetonitrile gives the compound of formula I, in which $R^5$=H, $R^1$, $R^2$, $R^3$, $R^4$, $R^{10}$, $R^{11}$, and $R^{21}$ are unchanged. When $R^1=R^2$=tert-butyldimethylsilyl group, $R^4$=tert-butyl group, treatment of the compound of formula I with an acid such as trifluoroacetic acid in an solvent such as methylene chloride gives the corresponding diol-acid of the compound of formula I, in which $R^1=R^2=R^4$=H, and $R^3$, $R^5$, $R^{10}$, $R^{11}$, and $R^{21}$ are unchanged.

Biological Activity

Evaluation of representative compounds of this invention in several standard pharmacological test procedures indicated that the compounds of this invention possess significant antibacterial activity. Based on the activity shown in the standard pharmacological test procedures, the compounds of this invention are therefore useful as antibacterial agents for treating infectious diseases in human and other animals.

The test procedures used and results obtained are shown below:

Methods for In Vitro Antibacteria Evaluation:

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of National Committee for Clinical Laboratory Standards. [Reference for the Methods for dilution antimicrobial susceptibility tests for bacteria that grow aerobically: National Committee for Clinical LaboratoryStandards, 1997. Approved standard M7-A National Committee for Clinical Laboratory Standards, Wayne, Pa.] An inoculum level of $5 \times 10^5$ CFU/ml, and a range of antibiotic concentrations (64–0.06 µg/ml) is used. The MIC is determined after the microtiter plates are incubated for 18 hours at 35° C. in an ambient air incubator. The test organisms comprise a spectrum of gram-positive bacteria including *Staphylococcus* sp., *Streptococcus* sp. and *Enterococcus* sp. These organisms include recent clinical isolates that are resistant to methicillin, penicillin and vancomycin.

Table I lists the in vitro MIC data µg/ml) testing data for representative compounds of the invention against a variety of microorganisms.

TABLE 1

Antimicrobial Activity (MIC, µg/ml) of AA896 Analogs

| Example | 1 | 2 | 3 | 4 | 5 | 6 | 7 |
|---|---|---|---|---|---|---|---|
| E. coli GC 4559 | >128 | >128 | >128 | >128 | >128 | >128 | >128 |
| E. coli GC 4560 | >128 | >128 | 128 | >128 | >128 | 128 | 32 |
| E. coli GC 3226 | >128 | >128 | >128 | >128 | >128 | >128 | >128 |
| S. marcescens GC 4077 | >128 | >128 | >128 | >128 | >128 | >128 | 128 |
| C. albicans GC 3066 | >128 | >128 | 128 | >128 | >128 | >128 | 32 |
| M. morganii GC 4531 | >128 | >128 | 128 | >128 | >128 | 128 | 128 |
| K. pneumoniae GC 4534 | >128 | >128 | >128 | >128 | >128 | >128 | 128 |

TABLE 1-continued

Antimicrobial Activity (MIC, μg/ml) of AA896 Analogs

| | | | | | | | |
|---|---|---|---|---|---|---|---|
| E. cloacae GC 3783 | >128 | >128 | >128 | >128 | >128 | >128 | 128 |
| P. aeruginosa GC 4532 | 128 | >128 | >128 | >128 | >128 | 128 | 128 |
| S. aureus GC 4536 | >128 | 16 | >128 | >128 | 16 | >128 | 1 |
| S. aureus GC 1131 | >128 | 4 | >128 | >128 | 32 | >128 | 1 |
| CNS GC 4537 | >128 | 4 | >128 | >128 | 4 | >128 | 1 |
| CNS GC 4538 | >128 | 4 | >128 | >128 | 8 | >128 | 2 |
| CNS GC 4547 | >128 | 16 | 128 | >128 | 64 | >128 | 2 |
| E. faecalis GC 842 | >128 | 8 | >128 | >128 | 16 | >128 | 2 |
| E. faecalis GC 2242 | 128 | 4 | 128 | 128 | 4 | 64 | 2 |
| E. coli GC 2203 | >128 | >128 | >128 | >128 | >128 | >128 | >128 |
| P. aeruginosa GC 2214 | 128 | >128 | 128 | 128 | >128 | 128 | 128 |
| S. aureus GC 2216 | >128 | 4 | >128 | >128 | 8 | >128 | 2 |
| E. faecalis GC 4555 | 128 | 4 | 128 | >128 | 8 | >128 | 2 |

| Example | 8 | 9 | 10 | 11 | 12 | 13 | 14 |
|---|---|---|---|---|---|---|---|
| E. coli GC 4559 | >128 | >128 | >128 | >128 | >128 | >128 | >128 |
| E. coli GC 4560 | 64 | 128 | >128 | >128 | 128 | >128 | 128 |
| E. coli GC 3226 | >128 | >128 | >128 | >128 | >128 | >128 | >128 |
| S. marcescens GC 4077 | 64 | >128 | >128 | >128 | 128 | >128 | >128 |
| C. albicans GC 3066 | 32 | 128 | 128 | >128 | 128 | >128 | 128 |
| M. morganii GC 4531 | 64 | >128 | >128 | >128 | 128 | >128 | 128 |
| K. pneumoniae GC 4534 | 64 | >128 | >128 | >128 | >128 | >128 | >128 |
| E. cloacae GC 3783 | 64 | >128 | >128 | >128 | 128 | >128 | >128 |
| P. aeruginosa GC 4532 | 64 | 128 | >128 | >128 | 128 | >128 | 128 |
| S. aureus GC 4536 | 128 | 128 | >128 | 4 | >128 | >128 | >128 |
| S. aureus GC 1131 | 128 | 128 | >128 | 8 | >128 | >128 | >128 |
| CNS GC 4537 | 128 | 128 | >128 | 4 | >128 | >128 | >128 |
| CNS GC 4538 | 128 | 128 | >128 | 4 | >128 | >128 | >128 |
| CNS GC 4547 | 128 | 8 | >128 | 8 | 128 | >128 | >128 |
| E. faecalis GC 842 | 64 | >128 | >128 | 4 | 128 | 128 | >128 |
| E. faecalis GC 2242 | 64 | 128 | 128 | 8 | 128 | 16 | 128 |
| E. coli GC 2203 | 64 | >128 | >128 | >128 | >128 | >128 | >128 |
| P. aeruginosa GC 2214 | 64 | 128 | >128 | 128 | 128 | >128 | 128 |
| S. aureus GC 2216 | 128 | 128 | >128 | 4 | >128 | >128 | >128 |
| E. faecalis GC 4555 | 64 | 128 | >128 | 4 | 128 | >128 | 128 |

| Example | 15 | 16 | 17 | 18 | 19 | 20 | 21 |
|---|---|---|---|---|---|---|---|
| E. coli GC 4559 | >128 | >128 | >128 | >128 | >128 | >128 | >128 |
| E. coli GC 4560 | 8 | >128 | >128 | >128 | 8 | >128 | >128 |
| E. coli GC 3226 | >128 | >128 | >128 | >128 | 128 | >128 | >128 |
| S. marcescens GC 4077 | >128 | >128 | >128 | >128 | 128 | >128 | >128 |
| C. albicans GC 3066 | 64 | 128 | >128 | >128 | 128 | 128 | >128 |
| M. morganii GC 4531 | 128 | >128 | >128 | >128 | 128 | >128 | >128 |
| K. pneumoniae GC 4534 | >128 | >128 | >128 | >128 | >128 | >128 | >128 |
| E. cloacae GC 3783 | >128 | >128 | >128 | >128 | >128 | >128 | >128 |
| P. aeruginosa GC 4532 | >128 | >128 | >128 | >128 | 128 | 128 | >128 |
| S. aureus GC 4536 | 4 | >128 | 128 | >128 | 8 | >128 | >128 |
| S. aureus GC 1131 | 4 | >128 | 128 | >128 | 4 | >128 | >128 |
| CNS GC 4537 | 4 | >128 | 128 | >128 | 8 | >128 | >128 |
| CNS GC 4538 | 4 | >128 | 64 | >128 | 8 | >128 | >128 |
| CNS GC 4547 | 8 | >128 | >128 | >128 | 16 | >128 | >128 |
| E. faecalis GC 842 | 4 | >128 | 32 | >128 | 8 | >128 | >128 |
| E. faecalis GC 2242 | 4 | 128 | 4 | >128 | 8 | >128 | >128 |
| E. coli GC 2203 | >128 | >128 | >128 | >128 | 128 | >128 | >128 |
| P. aeruginosa GC 2214 | 128 | >128 | >128 | >128 | 128 | 128 | >128 |
| S. aureus GC 2216 | 4 | >128 | 32 | >128 | 8 | >128 | >128 |
| E. faecalis GC 4555 | 4 | >128 | 16 | >128 | 8 | >128 | >128 |

| Example | 22 | 23 | 24 | 25 | 26 | 27 | 28 |
|---|---|---|---|---|---|---|---|
| E. coli GC 4559 | >128 | >128 | >128 | >128 | >128 | >128 | >128 |
| E. coli GC 4560 | >128 | 128 | 128 | >128 | 128 | >128 | >128 |
| E. coli GC 3226 | >128 | >128 | >128 | >128 | >128 | >128 | >128 |
| S. marcescens GC 4077 | >128 | 128 | 128 | 128 | 128 | >128 | >128 |

TABLE 1-continued

Antimicrobial Activity (MIC, μg/ml) of AA896 Analogs

| | | | | | | | |
|---|---|---|---|---|---|---|---|
| C. albicans GC 3066 | >128 | 128 | 128 | 128 | >128 | >128 | >128 |
| M. morganii GC 4531 | >128 | 128 | 128 | 128 | >128 | >128 | >128 |
| K. pneumoniae GC 4534 | >128 | >128 | >128 | >128 | >128 | >128 | >128 |
| E. cloacae GC 3783 | >128 | >128 | >128 | >128 | >128 | >128 | >128 |
| P. aeruginosa GC 4532 | >128 | 128 | 128 | 128 | >128 | >128 | >128 |
| S. aureus GC 4536 | >128 | 128 | >128 | 128 | >128 | >128 | >128 |
| S. aureus GC 1131 | >128 | >128 | >128 | 128 | >128 | >128 | >128 |
| CNS GC 4537 | >128 | 128 | >128 | 64 | >128 | >128 | >128 |
| CNS GC 4538 | >128 | 128 | >128 | 64 | >128 | >128 | >128 |
| CNS GC 4547 | >128 | >128 | >128 | 128 | >128 | >128 | >128 |
| E. faecalis GC 842 | >128 | 128 | >128 | 128 | >128 | >128 | >128 |
| E. faecalis GC 2242 | >128 | 128 | 128 | 64 | 128 | 128 | >128 |
| E. coli GC 2203 >128 | >128 | >128 | >128 | >128 | >128 | >128 | >128 |
| P. aeruginosa GC 2214 | >128 | 128 | 128 | 128 | 128 | 128 | >128 |
| S. aureus GC 2216 | >128 | 128 | >128 | 128 | >128 | >128 | >128 |
| E. faecalis GC 4555 | >128 | 128 | >128 | 128 | >128 | >128 | >128 |

| Example | 29 | 30 | 31a | 31b | 32 | 33 | 34 |
|---|---|---|---|---|---|---|---|
| E. coli GC 4559 | >128 | >128 | >128 | >128 | >128 | >128 | >128 |
| E. coli GC 4560 | 128 | 64 | 128 | >128 | 128 | >128 | >128 |
| E. coli GC 3226 | >128 | >128 | 128 | >128 | >128 | >128 | >128 |
| S. marcescens GC 4077 | 128 | 128 | 128 | >128 | 128 | >128 | >128 |
| C. albicans GC 3066 | >128 | 64 | 128 | >128 | >128 | >128 | 128 |
| M. morganii GC 4531 | 128 | 128 | 128 | 128 | 128 | >128 | >128 |
| K. pneumoniae GC 4534 | 128 | 128 | 128 | 128 | 128 | >128 | >128 |
| E. cloacae GC 3783 | 128 | 128 | 128 | 128 | 128 | >128 | >128 |
| P. aeruginosa GC 4532 | 128 | 64 | 128 | >128 | 128 | >128 | 128 |
| S. aureus GC 4536 | >128 | 128 | >128 | >128 | >128 | >128 | >128 |
| S. aureus GC 1131 | >128 | 128 | >128 | >128 | 128 | >128 | >128 |
| CNS GC 4537 | >128 | 128 | >128 | >128 | 128 | >128 | >128 |
| CNS GC 4538 | >128 | 128 | >128 | >128 | 128 | >128 | >128 |
| CNS GC 4547 | >128 | 128 | >128 | 128 | 128 | >128 | >128 |
| E. faecalis GC 842 | 128 | 128 | 128 | 128 | >128 | >128 | >128 |
| E. faecalis GC 2242 | 128 | 64 | 128 | >128 | >128 | >128 | 128 |
| E. coli GC 2203 >128 | >128 | >128 | 128 | >128 | >128 | >128 | >128 |
| P. aeruginosa GC 2214 | 128 | 64 | 128 | >128 | >128 | >128 | 128 |
| S. aureus GC 2216 | >128 | 128 | 128 | >128 | >128 | >128 | >128 |
| E. faecalis GC 4555 | >128 | 64 | 128 | >128 | >128 | >128 | >128 |

| Example | 35 | 36 | 37 | 38a | 38b | 39 | 40 |
|---|---|---|---|---|---|---|---|
| E. coli GC 4559 | >128 | >128 | >128 | >128 | >128 | >128 | >128 |
| E. coli GC 4560 | >128 | >128 | >128 | >128 | >128 | >128 | >128 |
| E. coli GC 3226 | >128 | >128 | >128 | >128 | >128 | >128 | >128 |
| S. marcescens GC 4077 | >128 | >128 | >128 | >128 | >128 | 128 | >128 |
| C. albicans GC 3066 | 128 | 128 | 128 | >128 | 128 | 128 | >128 |
| M. morganii GC 4531 | 128 | 128 | 128 | >128 | 128 | 128 | >128 |
| K. pneumoniae GC 4534 | >128 | >128 | >128 | >128 | >128 | >128 | >128 |
| E. cloacae GC 3783 | >128 | >128 | >128 | >128 | >128 | >128 | >128 |
| P. aeruginosa GC 4532 | 128 | 128 | >128 | >128 | >128 | 128 | 128 |
| S. aureus GC 4536 | >128 | >128 | >128 | >128 | >128 | >128 | >128 |
| S. aureus GC 1131 | >128 | >128 | >128 | >128 | >128 | >128 | >128 |
| CNS GC 4537 | >128 | >128 | >128 | >128 | >128 | >128 | >128 |
| CNS GC 4538 | >128 | >128 | >128 | >128 | >128 | >128 | >128 |
| CNS GC 4547 | >128 | >128 | >128 | >128 | >128 | >128 | >128 |
| E. faecalis GC 842 | >128 | >128 | >128 | >128 | >128 | >128 | >128 |
| E. faecalis GC 2242 | 128 | 128 | 128 | >128 | 128 | 128 | 128 |
| E. coli GC 2203 >128 | >128 | >128 | >128 | >128 | >128 | >128 | >128 |
| P. aeruginosa GC 2214 | 128 | 128 | >128 | >128 | >128 | 128 | 128 |
| S. aureus GC 2216 | >128 | >128 | >128 | >128 | >128 | >128 | >128 |
| E. faecalis GC 4555 | >128 | >128 | >128 | >128 | >128 | >128 | >128 |

| Example | 41 | 42 | 43 | 44 | 45 | 46 | 47 |
|---|---|---|---|---|---|---|---|
| E. coli GC 4559 | >128 | >128 | >128 | >128 | >128 | >128 | >128 |

TABLE 1-continued

Antimicrobial Activity (MIC, µg/ml) of AA896 Analogs

| | | | | | | | |
|---|---|---|---|---|---|---|---|
| E. coli GC 4560 | >128 | 128 | >128 | 128 | >128 | 128 | 128 |
| E. coli GC 3226 | >128 | 128 | >128 | >128 | >128 | >128 | >128 |
| S. marcescens GC 4077 | >128 | 128 | >128 | 128 | >128 | >128 | 128 |
| C. albicans GC 3066 | 128 | 128 | 128 | 128 | 128 | 128 | 128 |
| M. morganii GC 4531 | 128 | 128 | >128 | 128 | 128 | 128 | 128 |
| K. pneumoniae GC 4534 | >128 | 128 | >128 | >128 | >128 | >128 | >128 |
| E. cloacae GC 3783 | >128 | 128 | >128 | >128 | >128 | >128 | >128 |
| P. aeruginosa GC 4532 | 128 | 128 | 128 | 128 | 128 | 128 | 128 |
| S. aureus GC 4536 | >128 | >128 | >128 | >128 | >128 | >128 | >128 |
| S. aureus GC 1131 | >128 | >128 | >128 | >128 | >128 | >128 | >128 |
| CNS GC 4537 | >128 | >128 | >128 | >128 | >128 | >128 | >128 |
| CNS GC 4538 | >128 | >128 | >128 | >128 | >128 | >128 | >128 |
| CNS GC 4547 | >128 | 128 | >128 | >128 | >128 | >128 | >128 |
| E. faecalis GC 842 | >128 | 128 | >128 | 128 | >128 | 128 | 128 |
| E. faecalis GC 2242 | 128 | 64 | >128 | 64 | 128 | 128 | 64 |
| E. coli GC 2203 >128 | >128 | >128 | >128 | >128 | >128 | >128 | |
| P. aeruginosa GC 2214 | 128 | 128 | 128 | 128 | 128 | 128 | >128 |
| S. aureus GC 2216 | >128 | >128 | >128 | >128 | >128 | >128 | >128 |
| E. faecalis GC 4555 | >128 | 128 | >128 | 128 | >128 | 128 | 128 |

| Example | 48 | 49 | 50 | 51 | 52 | 53 | 54 |
|---|---|---|---|---|---|---|---|
| E. coli GC 4559 | >128 | >128 | >128 | >128 | >128 | >128 | >128 |
| E. coli GC 4560 | 128 | >128 | >128 | 128 | 128 | 128 | 128 |
| E. coli GC 3226 | >128 | >128 | >128 | >128 | >128 | >128 | >128 |
| S. marcescens GC 4077 | 128 | >128 | >128 | >128 | 128 | >128 | >128 |
| C. albicans GC 3066 | 128 | 128 | 128 | 128 | 128 | 128 | >128 |
| M. morganii GC 4531 | 128 | 128 | 128 | 128 | 128 | >128 | 128 |
| K. pneumoniae GC 4534 | >128 | >128 | >128 | >128 | >128 | >128 | >128 |
| E. cloacae GC 3783 | >128 | >128 | >128 | >128 | >128 | >128 | >128 |
| P. aeruginosa GC 4532 | 128 | 128 | 128 | 128 | 128 | 128 | >128 |
| S. aureus GC 4536 | >128 | >128 | >128 | >128 | >128 | >128 | >128 |
| S. aureus GC 1131 | >128 | >128 | >128 | >128 | >128 | >128 | >128 |
| CNS GC 4537 | >128 | >128 | >128 | >128 | >128 | >128 | >128 |
| CNS GC 4538 | >128 | >128 | >128 | 128 | >128 | >128 | >128 |
| CNS GC 4547 | 128 | >128 | >128 | >128 | >128 | >128 | >128 |
| E. faecalis GC 842 | 128 | 128 | >128 | 128 | 128 | 128 | 128 |
| E. faecalis GC 2242 | 64 | 128 | 128 | 128 | 128 | 128 | 128 |
| E. coli GC 2203 >128 | >128 | >128 | >128 | >128 | >128 | >128 | |
| P. aeruginosa GC 2214 | >128 | 128 | 128 | 128 | 128 | 128 | >128 |
| S. aureus GC 2216 | >128 | >128 | >128 | >128 | >128 | >128 | >128 |
| E. faecalis GC 4555 | 128 | >128 | >128 | 128 | >128 | 128 | >128 |

| Equation | 55 | 56 | 57 | 58 |
|---|---|---|---|---|
| E. coli GC 4559 | >128 | >128 | >128 | >128 |
| E. coli GC 4560 | 128 | >128 | 128 | >128 |
| E. coli GC 3226 | 128 | >128 | >128 | >128 |
| S. marcescens GC 4077 | 128 | >128 | 128 | >128 |
| C. albicans GC 3066 | 128 | >128 | 128 | >128 |
| M. morganii GC 4531 | 128 | 128 | 128 | >128 |
| K. pneumoniae GC 4534 | 128 | >128 | >128 | >128 |
| E. cloacae GC 3783 | 128 | >128 | 128 | >128 |
| P. aeruginosa GC 4532 | 128 | 128 | 128 | >128 |
| S. aureus GC 4536 | >128 | >128 | 8 | >128 |
| S. aureus GC 1131 | >128 | >128 | 64 | >128 |
| CNS GC 4537 | >128 | >128 | 4 | >128 |
| CNS GC 4538 | >128 | >128 | 4 | >128 |
| CNS GC 4547 | >128 | >128 | 64 | >128 |
| E. faecalis GC 842 | 128 | >128 | 8 | >128 |
| E. faecalis GC 2242 | 128 | 128 | 4 | >128 |
| E. coli GC 2203 >128 | 128 | >128 | >128 | >128 |
| P. aeruginosa GC 2214 | 128 | 128 | 128 | >128 |
| S. aureus GC 2216 | >128 | >128 | 32 | >128 |
| E. faecalis GC 4555 | 128 | >128 | 4 | >128 |

Determination of Lipid II Formation by a TLC Methodology

The MurG biochemical assay utilizes S. epidermides membranes to catalyze the late steps in cell wall biosynthesis including MraY, the phospho-MurNAc pentapeptide translocase and MurG, the UDP-N-Acetylglucosaminyl transferase. The following procedure is adapted from the method described by Mengin-Lecreaulx, et al (J. Bacteriol 173(15) 4625–4636,1991). In this procedure, the formation of Lipid II is assessed using radiolabeled UDP-N-Acetylglucosamine.

S. epidermides membranes, compound, UDP-MurNAc pentapeptide, and [$^{14}$C]-UDP-N-Acetylglucosamine were incubated at room temperature for 30 min. The reaction was terminated by boiling in a water bath for 1 minute. 2 µl samples of each reaction are analyzed by TLC. The samples are spotted onto K6 silica plates and chromatographed in Isobutyric Acid:1M NH$_4$OH (5:3). The plates are exposed to film and the inhibition of Lipid II formation can be monitored by comparing the sample area to the control area.

| Example No. | 100 | 50 | 25 | 6.25 |
|---|---|---|---|---|
| 5 | + | + | + | − |
| 19 | + | + | − | − |
| 9 | + | + | − | − |
| 27 | + | + | − | − |
| 17 | + | + | − | − |

In therapeutic use, the compounds of this invention may be administered in the form of conventional pharmaceutical composition appropriate for the intended use as antibacterials. Such compositions may be formulated so as to be suitable for oral, parenteral or topical administration. The active ingredient may be combined in admixture with non-toxic pharmaceutical carrier may take a variety of forms, depending on the form of preparation desired for administration, i.e. oral, parenteral, or topical.

When the compounds are employed as antibacterials, they can be combined with one or more pharmaceutically acceptable carriers, for example, solvents, diluentsand the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotics of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotics of the invention.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an antibacterially effective amount of a compound of this invention and a pharmaceutically acceptable carrier.

The present invention further provides a method of treating bacterial infections in warm-blooded animals including man, which comprises providing to the afflicted warm-blooded animals an antibacterially effective amount of a compound or a pharmaceutical composition of a compound of the invention. The invention will be more fully described in conjunction with the following specific examples which are not to be construed as limiting the scope of the invention.

The following examples illustrate the preparation of the compounds of the invention by fermentation and synthetic procedures and as such are not to be considered as limiting the invention set forth in the claims appended hereto.

EXPERIMENTALS

Preparation of Uridyl-glycine Segment

Reference Example 1

1-[5-[Bis-(4-methoxy-phenyl)-phenyl-methoxymethyl]-3,4-bis-(tert-butyl-dimethylsilanyloxy)-tetrahydro-furan-2-yl]-1H-pyrimidine-2,4-dione

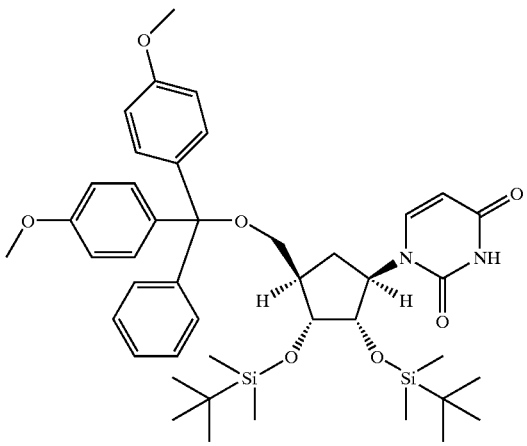

Following the literature procedure (Myers, A. G.; Gin, D. Y.; Rogers, D. H., J. Amer. Chem. Soc., 1994, 116, 4697–4718), a mixture of uridine (10 g, 41 mmole, Aldrich) and dimethoxytrityl chloride (13.9 g, 41 mmole) in dry pyridine (70 ml) was stirred at room temperature under nitrogen for 15 h. The resulting dark red solution was concentrated in vacuo, and the residue was dissolved in ethyl acetate (500 ml). The organic layer was washed with saturated sodium bicarbonate aqueous solution, and saturated sodium chloride solution, dried over magnesium sulfate, filtered and concentrated in vacuo. The residue was triturated with a mixture of diethyl ether and hexanes to give 1-[5-[Bis-(4-methoxy-phenyl)-phenyl-methoxymethyl]-3,4-dihydroxy-tetrahydro-furan-2-yl]-1H-pyrimidine-2,4-dione (21 g, 94%) as a white solid. 1-[5-[Bis-(4-methoxy-phenyl)-phenyl-methoxymethyl]-3,4-dihydroxy-tetrahydro-furan-2-yl]-1H-pyrimidine-2,4-dione (20.5 g, 37. 6 mmole) was dissolved in anhydrous dimethylformamide (100 ml), and imidazole (6.4 g, 93.9 mmole) and tert-butyldimethylsilyl chloride (12.5 g, 82.6 mmole) were added to this solution. The resulting mixture was stirred at room temperature for 15 h under nitrogen, and diluted with ethyl acetate (700 ml). The organic layer was washed with sat. sodium bicarbonate aqueous solution and sat. sodium chloride solution, dried over magnesium sulfate, filtered and concentrated in vacuo. The residue was chromatographed (flash column, silica gel, methylene chloride: n-hexane:diethyl ether:methanol= 49:49:1:1) to give 1-[5-[Bis-(4-methoxy-phenyl)-phenyl-methoxymethyl]-3,4-bis-(tert-butyl-dimethyl-silanyloxy)-tetrahydro-furan-2-yl]-1H-pyrimidine-2,4-dione as pale yellow solid (25 g, 86%).

MS (ES) m/z: 775.2 (M+H).

IR cm$^{-1}$: 1685, 1509, 1253.

H-NMR (δ, DMSO-d$_6$): 11.5 (1H, s), 7.837 (1H, d, J=8.1 Hz), 7.389–7.224 (9H, m), 6.920–6.799 (4H, m), 5.758 (1H, bs), 5.754–5.732 (1H, m), 5.362 (1H, d), 4.289–4.262 (1H, m), 3.982–3.677 (1H, m), 3.741 (6H, s), 3.468–3.432 (1H, m), 3.271–3.202 (1H, m), 0.843 (9H, s), 0.750 (9H, s), 0.100 (3H, s), 0.050 (3H, s), 0.020 (3H, s), −0.050 (3H, s).

Analysis for $C_{42}H_{58}N_2O_8Si_2$: Calcd: C, 65.08; H, 7.54; N, 3.61. Found: C, 62.96; H, 7.84: N, 3.98.

$[\alpha]_D^{25}$=+8±2 (methylene chloride).

Reference Example 2

1-[(2R,3R,4R,5R)-3,4-bis{[tert-Butyl(dimethyl)silyl]oxy-5-(hydroxymethyl)tetrahydro-2-furanyl]-3-(4-methoxybenzyl)-2,4(1H,3H)-pyrimidinedione

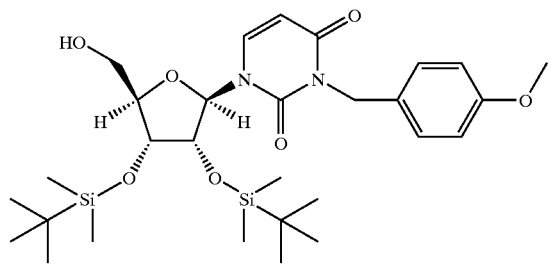

Following the procedure (Myers, A. G.; Gin, D. Y.; Rogers, D. H., J. Amer. Chem. Soc., 1994, 116, 4697–4718), a suspension of sodium hydride (1.55 g, 38.75 mmole, 60% oil dispersion) in anhydrous dimethylformamide (40 ml) was cooled at 0° C. under argon, and to this mixture was added a solution of 1-[5-[bis-(4-methoxy-phenyl)-phenyl-methoxymethyl]-3,4-bis-(tert-butyl-dimethyl-silanyloxy)-tetrahydro-furan-2-yl]-1H-pyrimidine-2,4-dione (20 g, 25.8 mmole, obtained from Reference Example 1) in anhydrous dimethylformamide (35 ml) over a period of 15 min. Neat p-methoxybenzyl chloride (7 ml, 51 mmole) was added to this solution. The resulting mixture was stirred at 0° C. for 15 h under argon, and diluted with ethyl acetate (700 ml). The organic layer was washed with saturated sodium bicarbonate aqueous solution and saturated sodium chloride solution, dried over magnesium sulfate, filtered and concentrated to dryness in vacuo. The oily residue was dissolved in chloroform (200 ml) and cooled at 0° C. under nitrogen. Benzenesulfonic acid (6 g, 37.93 mmole) was added portionwise, and the resulting red solution was stirred at 0° C. under nitrogen for 2 h. The mixture was diluted with ethyl acetate. The organic layer was washed with saturated sodium bicarbonate aqueous solution and saturated sodium chloride solution, dried over magnesium sulfate, filtered and concentrated to dryness in vacuo. The residue was chromatographed (flash column, silica gel, methylene chloride:diethyl ether:methanol=95:3:2) to give 1-[(2R,3R,4R,5R)-3,4-bis{[tert-butyl(dimethyl)silyl]oxy}-5-(hydroxymethyl)tetrahydro-2-furanyl]-3-(4-methoxybenzyl)-2,4(1H,3H)-pyrimidinedione as white solid (9 g, 59%).

Mass (ES): m/z 593.3 (M+H).

IR cm$^{-1}$: 2930, 1708, 1665.

H-NMR (δ, DMSO-d$_6$): 7.988 (1H, d, J=8.1 Hz), 7.294 (2H, d, J=40 Hz), 6.842 (2H, d), 5.897 (1H, s), 5.879–5.826 (1H, m), 5.265 (1H, t, J=4.8 Hz), 4.955–4.842 (2H, m), 4.259–4.224 (1H, m), 4.146–4.124 (1H, m), 3.897–3.889 (1H, m), 3.770 (3H, s), 3.652–3.639 (1H, m), 3.589–3.575 (1H, m), 0.886 (9H, s), 0.751 (9H, s), 0.150 (3H, s), 0.100 (3H, s), −0.050 (3H, s), −0.150 (3H, s).

Analysis for $C_{29}H_{48}N_2O_7Si_2$: Calcd: C, 58.75; H, 8.16; N, 4.72. Found: C, 59.86; H, 8.25: N, 4.53.

$[\alpha]_D^{25}$=−4±2 (methylene chloride).

Reference Example 3

1-[(2R,3R,4R,5R)-3,4-bis{[tert-Butyl(dimethyl)silyl]oxy}-5-[3-(4-methoxybenzyl)-2,4-dioxo-3,4-dihydro-2H-pyrimidin-1-yl]-tetrahydro-furan-2-carbaldehyde

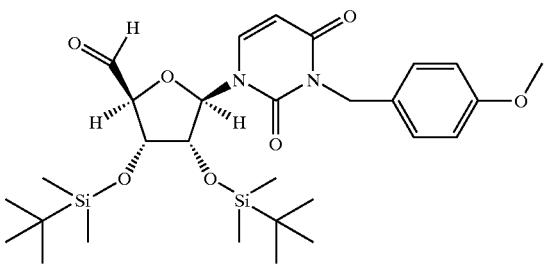

Following the literature procedure (Myers, A. G.; Gin, D. Y.; Rogers, D. H., J. Amer. Chem. Soc., 1994, 116, 4697–4718), anhydrous dimethyl sulfoxide (3.35 ml, 47.23 mmole) was added dropwise to a solution of oxalyl chloride (14.2 ml, 28.34 mmole, 2.0 M solution in methylene chloride, Aldrich) in anhydrous methylene chloride (50 ml) under argon at −78° C. The resulting mixture was stirred at −78° C. for 45 min, and was transferred via cannula to a cooled (−78° C.) solution of 1-[(2R,3R,4R,5R)-3,4-bis{[tert-butyl(dimethyl)silyl]oxy}-5-(hydroxymethyl)tetrahydro-2-furanyl]-3-(4-methoxybenzyl)-2,4(1H,3H)-pyrimidinedione (5.6 g, 9.45 mmole, obtained from Reference Example 2) in anhydrous methylene chloride (50 ml) under argon. The resulting mixture was stirred at −78° C. for 1 h, and triethylamine (9.9 ml, 70.8 mmole) was added all at once. The mixture was stirred at −78° C. for 1.5 h under argon, and diluted with ethyl acetate (500 ml). The organic layer was washed with saturated sodium bicarbonate aqueous solution and saturated sodium chloride solution, dried over magnesium sulfate, filtered and concentrated to dryness in vacuo. Toluene was added to the residue, and evaporated in vacuo. This procedure was repeated for two more times, to give 1-[(2R,3R,4R,5R)-3,4-bis{[tert-butyl(dimethyl)silyl]oxy}-5-[3-(4-methoxybenzyl)-2,4-dioxo-3,4-dihydro-2H-pyrimidin-1-yl]-tetrahydro-furan-2-carbaldehyde as pale yellow solid (5.31 g, 95%). This material was used in its crude form in the following experiment. MS (ES): m/z 591.3 (M+H).

Reference Example 4 tert-Butyl (2S,3S)-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-(dibenzylamino)-3-hydroxypropanoate

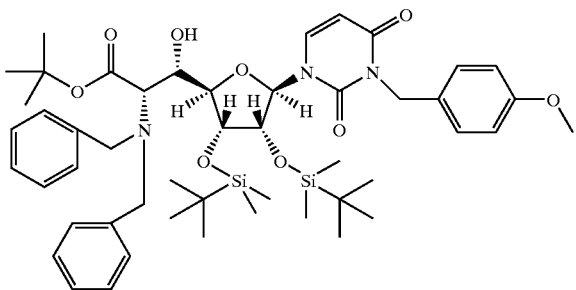

and tert-Butyl (2S,3R)-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-(dibenzylamino)-3-hydroxypropanoate

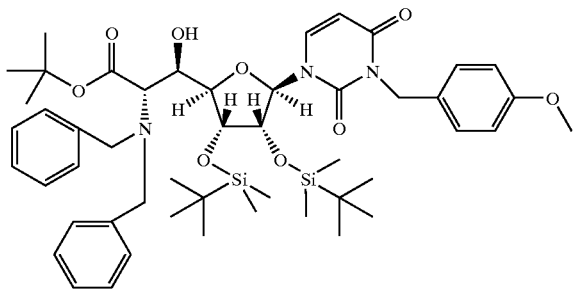

tert-Butyl 2-(dibenzylamino)-propanoate was prepared from tert-butyl bromoacetate (10 ml, 68 mmole) and dibenzylamine (26.5 ml, 138 mmole) in 1,4-dioxane (20 ml) and abs. ethanol (25 ml), following the literature procedure (Scolastico, C. *Tetrahedron Letts.*, 1987, 43, 2317). A solution of tert-butyl 2-(dibenzylamino)-propanoate (4.75 g, 15.23 mmole) in anhydrous tetrahydrofuran (60 ml) was cooled at −78° C. under argon. A solution of lithium diisopropylamide (7.6 ml, 15.23 mmole, 2.0 M solution in tetrahydrofuran, Aldrich) was introduced to this cooled solution over a period of 15 min, and the resulting reddish orange solution was stirred at this temperature for 1 h. A solution of 1-[(2R,3R,4R,5R)-3,4-bis{[tert-butyl(dimethyl)silyl]oxy}-5-[3-(4-methoxybenzyl)-2,4-dioxo-3,4-dihydro-2H-pyrimidin-1-yl]-tetrahydro-furan-2-carbaldehyde (4.5 g, 7.62 mmole, obtained from Reference Example 3) in anhydrous tetrahydrofuran was added via syringe to the cooled mixture over a period of 15 min. The resulting mixture was stirred at −30° C. for 15 h under argon, and diluted with ethyl acetate. The organic layer was washed with saturated sodium bicarbonate aqueous solution and saturated sodium chloride solution, dried over magnesium sulfate, filtered and concentrated to dryness in vacuo. The residue was chromatographed (flash column, silica gel, methylene chloride:n-hexane:methanol:diethyl ether=49:49:1:1) to give tert-butyl (2S,3S)-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-2-(dibenzylamino)-3-hydroxypropanoate (990 mg, 14.4%) as a white amorphous solid.

Mass (ES) m/z: 902.2 (M+H).

IR cm$^{-1}$: 2955, 2930, 1720, 1669.

H-NMR (δ, DMSO-d$_6$): 7.976 (1H, d), 7.439–7.180 (12H, m), 6.828 (2H, d, J=9 Hz), 5.854 (1H, d, J=3.9 Hz), 5.829 (1H, d, J=1.8 Hz), 5.281 (1H, d, J=4.2 Hz), 4.851 (2H, dd), 4.240–4.095 (3H, m), 3.936 (2H, d), 3.746 (1H, d), 3.770 (3H, s), 3.503 (2H, d, J=13.5), 3.266 (1H, d, J=10.5 Hz), 1.476 (9H, s), 0.857 (9H, s), 0.706 (9H, s), 0.150 (3H, s), 0.100 (3H, s), −0.050 (3H, s), −0.150 (3H, s).

Analysis for C$_{49}$H$_{71}$N$_3$O$_9$Si$_2$: Calcd: C, 65.23; H, 7.93; N, 4.66. Found: C, 64.66; H, 7.72: N, 4.41.

[α]$_D^{25}$=+28±4 (methanol).

Further elution gave tert-butyl (2S,3R)-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-(dibenzylamino)-3-hydroxypropanoate (2.14 g, 31%) as a white amorphous solid. Further elution gave the recovered aldehyde (1.66 g, 37%).

Mass (ES) m/z: 902.3 (M+H).

IR cm$^{-1}$: 2955, 2930, 1712, 1667.

H-NMR (δ, DMSO-d$_6$): 7.731 (1H, d, J=8.1 Hz), 7.402–7.034 (12H, m), 6.883 (2H, d, J=11.4 Hz), 5.868–5.739 (1H, m), 5.683 (1H, d, J=8.1 Hz), 4.943 (2H, dd), 4.414–4.406 (1H, m), 4.153–4.090 (3H, m), 3.797–3.777 (2H, m), 3.751 (3H, s), 3.750–3.738 (2H, m), 3.77 (1H, bs), 3.163 (1H, d, J=10.2 Hz), 1.543 (9H, s), 0.857 (9H, s), 0.787 (9H, s), 0.150 (3H, s), 0.100 (3H, s), 0.050 (3H, s), −0.050 (3H, s).

Analysis for C$_{49}$H$_{71}$N$_3$O$_9$Si$_2$: Calcd: C, 65.23; H, 7.93; N, 4.66. Found: C, 65.23; H, 8.00: N, 4.62.

[α]$_D^{25}$=+43±2 (methanol).

Reference Example 5 tert-Butyl (2S,3S)-2-amino-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

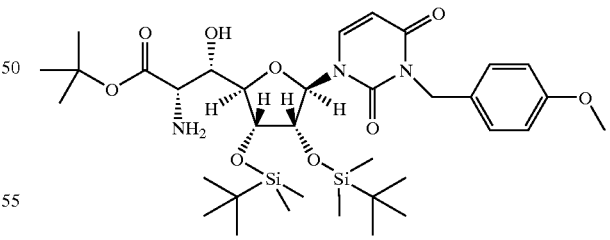

tert-Butyl (2S,3S)-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-2-(dibenzylamino)-3-hydroxy-propanoate (850 mg, 0.942 mmole, obtained from Reference Example 4) was hydrogenated using 10% palladium on carbon in methanol (10 ml) under atmospheric pressure. The catalyst was removed and the volatile was removed in vacuo. The residue was chromatographed (flash column, silica gel, methylene chloride:methanol:diethyl ether=95:2:3) to give the recovered starting material (248 mg, 29%) and tert-butyl (2S,3S)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (141 mg, 21%) as a white amorphous solid.

Mass (ES): m/z 722.2 (M+H).

IR cm$^{-1}$: 2955, 2931, 1716, 1670.

H-NMR (δ, DMSO-d$_6$): 7.933 (1H, d, J=8.1 Hz), 7.375 (2H, d, J=8.7 Hz), 7.267 (1H, d), 6.787–6.711 (2H, m), 5.835 (1H, d, J=4.5 Hz), 5.710–5.570 (2H, m), 5.220 (2H, bs), 4.962 (1H, bs), 4.190–4.044 (2H, m), 3.714 (3H, s), 3.553–3.415 (2H, m), 2.618–2.598 (1H, m), 1.410 (9H, s), 0.828 (9H, s), 0.765 (9H, s), 0.150 (3H, s), 0.100 (3H, s), –0.050 (3H, s), –0.150 (3H, s).

Analysis for C$_{35}$H$_{59}$N$_3$O$_9$Si$_2$: Calcd: C, 58.22; H, 8.24; N, 5.82. Found: C, 58.57; H, 8.42: N, 5.64.

$[\alpha]_D^{25}$=+31±4 (methanol).

The absolute stereochemistry of tert-butyl (2S,3S)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate was determined by the X-ray analysis of the para-nitrophenyl urea derivative, tert-butyl (2S,3S)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl)-3-hydroxy-2-{[(4-nitroanilino)carbonyl]amino}propanate.

Reference Example 6 tert-Butyl (2S,3R)-2-amino-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

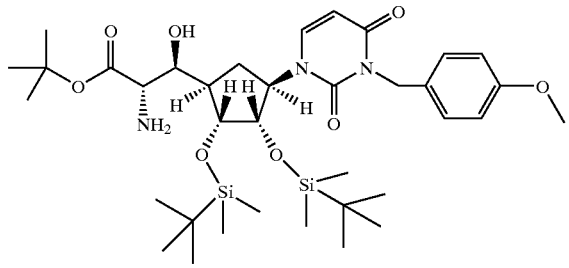

tert-Butyl (2S,3R)-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-2-(dibenzylamino)-3-hydroxy-propanoate (3.0 g, 3.33 mmole, obtained from Reference Example 4) was hydrogenated using 10% palladium on carbon (2 g) in methanol (70 ml) under atmospheric pressure. The catalyst was removed, and the volatile was removed in vacuo. The residue was chromatographed (flash column, silica gel, methylene chloride:methanol:diethyl ether=92:4:4) to give the recovered starting material (1.2 g, 50%) and tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (600 mg, 25%) as a white amorphous solid.

Mass (ES): m/z 722.2 (M+H).

IR cm$^{-1}$: 2955, 2931, 1715, 1671

H-NMR (δ, DMSO-d$_6$): 8.099 (1H, d, J=8.1 Hz), 7.239 (2H, d, J=9.7 Hz), 6.856–6.810 (2H, m), 5.945 (1H, d, J=7.8 Hz), 5.851 (1H, d, J=5.4 Hz), 5.584 (1H, d, J=6.0 Hz), 4.947–4.882 (2H, m), 4.333–4.293 (2H, m), 4.263–4.249 (1H, m), 3.727 (3H, s), 3.265–3.189 (1H, m), 1.794 (1H, bs), 1.414 (9H, s), 1.340 (2H, bs), 0.890 (9H, s), 0.727 (9H, s), 0.150 (3H, s), 0.100 (3H, s), –0.050 (3H, s), –0.150 (3H, s).

Analysis for C$_{35}$H$_{59}$N$_3$O$_9$Si$_2$: Calcd: C, 58.22; H, 8.24; N, 5.82. Found: C, 58.51; H, 8.19: N, 5.65.

$[\alpha]_D^{25}$=–7±8 (methanol).

The absolute stereochemistry of tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate was determined by the X-ray analysis of the para-nitrophenyl urea derivative, tert-butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl)-3-hydroxy-2-{[(4-nitroanilino)carbonyl]amino}propanate Preparation of Linker Segment Containing Hydroxylleucine and other Linker Segments Reference Example 7

(S)-(2-Hydroxy-1-phenyl-ethylamino)-acetic acid tert-butyl ester

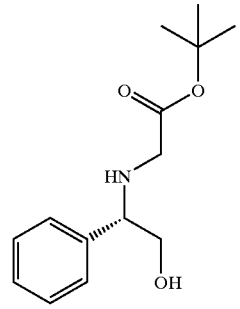

Following the literature procedure (Panek, J., *J. Org. Chem.*, 1998, 63, 2382), triethylamine (6.2 ml, 44.5 mmole) was added to a solution of (S)-phenylglycinol (5 g, 36.45 mmole) in anhydrous tetrahydrofuran (150 ml) under argon at 0° C. After stirring for 15 min, tert-butyl bromoacetate (5.9 ml, 39.96 mmole) was added slowly to this cooled solution. The resulting mixture was warmed to room temperature, and stirred for 15 h. Saturated ammonium chloride aqueous solution was added, and the aqueous layer was extracted with diethyl ether (3 times). The combined extracts were washed with saturated sodium chloride solution, dried over magnesium sulfate, filtered and concentrated to dryness in vacuo. The resulting solid was recrystallized from a diethyl ether/n-hexane mixture to give tert-butyl (S)-(2-Hydroxy-1-phenyl-ethylamino)-acetate as a white solid (3 g, 33%).

MS (ES): m/z 252.3 (M+H).

IR cm$^{-1}$: 1736.

H-NMR (δ, DMSO-d$_6$): 7.400–7.228 (5H, m), 4.975 (1H, bs), 4.248 (1H, dd, J=4.5, 7.8 Hz), 3.705–3.424 (2H, m), 3.117 (1H, d$_{AB}$, J=16.8 Hz), 2.989 (1H, d$_{AB}$), 2.513–2.502 (1H, m), 1.388 (9H, s).

Analysis for C$_{14}$H$_{21}$N$_1$O$_3$: Calcd: C, 66.91; H, 8.42; N, 5.57. Found: C, 65.88; H, 8.14: N, 5.47.

Reference Example 8

((4R)-2-Benzhydryl-4-phenyl-oxazolidin-3-yl)-acetic acid tert-butyl ester

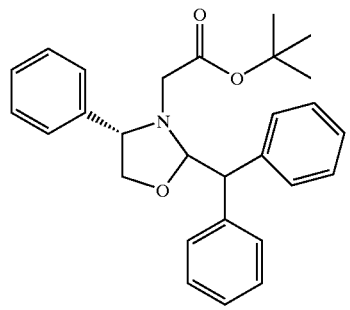

To a solution of tert-butyl (S)-(2-hydroxy-1-phenyl-ethylamino)-acetate (2.5 g, 10 mmole, obtained from Reference Example 9) in anhydrous methylene chloride (35 ml) were added diphenylacetaldehyde (2.16 g, 11 mmole) and magnesium sulfate (1.2 g, 10 mmole) under nitrogen. The resulting mixture was stirred at room temperature under nitrogen for 15 h, and diluted with ether. The organic layer was washed with saturated sodium chloride solution, dried over magnesium sulfate, filtered and concentrated to dryness in vacuo. The oily residue was solidified upon standing, and recrystallized from ether/hexanes to give tert-butyl ((4R)-2-benzhydryl-4-phenyl-oxazolidin-3-yl)-acetate as a white solid (4.9 g, 98%).

MS (ES): m/z 430.4 (M+H).

IR cm$^{-1}$: 1728.

H-NMR (δ, DMSO-d$_6$): 7.50–7.07 (15H, m), 5.335 (1H, d, J=3.0 Hz), 4.362 (1H, d, J=3.6 Hz), 4.285 (1H, t, J=4.2 Hz), 4.219 (2H, dd, J=4.2, 7.2 Hz), 1.330 (9H, s).

Analysis for C$_{28}$H$_{31}$N$_1$O$_3$: Calcd: C, 78.29; H, 7.27; N, 3.26. Found: C, 78.18; H, 7.46: N, 3.12.

Reference Example 9

(2S,3S)-2-((4R)-2-Benzhydryl-4-phenyl-oxazolidin-3-yl)-3-hydroxy-4-methyl-pentanoic acid tert-butyl ester

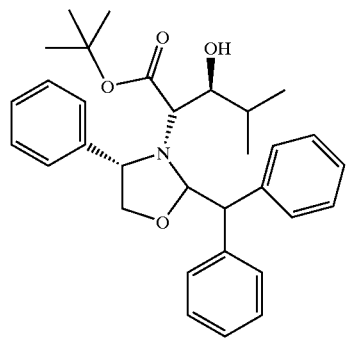

A solution of tert-butyl ((4R)-2-benzhydryl-4-phenyl-oxazolidin-3-yl)-acetate (3.0 g, 6.98 mmole, obtained from Reference Example 10) in anhydrous terahydrofuran (86 ml) was cooled at −78° C. under argon. A solution of lithium diisopropylamide (2M solution in heptane/tetrahydrofuran/ethylbenzene, Aldrich) was added dropwise over a period of 10 min, and the resulting orange solution was stirred at −78° C. for 1 h. A solution of isobutyraldehyde in anhydrous tetrahydrofuran (10 ml) was added to the cooled reaction mixture via syringe, and the resulting mixture was stirred at −78° C. for an additional 1 h. Saturated sodium bicarbonate aqueous solution was added, and the mixture was warmed to room temperature. The organic layer was separated, and the aqueous layer was extracted with ethyl acetate (3 times). The extracts were combined, washed with saturated sodium chloride aqueous solution, dried over magnesium sulfate, filtered and concentrated. The residue was chromatographed (flash column, silica gel, methylene chloride:methanol:diethyl ether=90:2:8) to give (2S,3S)-2-((4R)-2-benzhydryl-4-phenyl-oxazolidin-3-yl)-3-hydroxy-4-methyl-pentanoic acid tert-butyl ester (1.5 g, %) as a pale yellow solid.

MS (ES): m/z 502.4 (M+H).

IR cm$^{-1}$: 3578, 2970, 1699

H-NMR (δ, DMSO-d$_6$): 7.382–6.707 (15H, m), 5.222 (1H, d, J=6.0 Hz), 4.725 (1H, t, J=6.3 Hz), 4.434 (1H, d, J=5.7 Hz), 4.199 (1H, d, J=6.0 Hz), 3.949 (1H, t, J=8.1 Hz), 3.459 (1H, dd, J=5.4, 8.4 Hz), 1.367 (9H, s), 0.150 (3H, d), −0.05 (3H, d).

Analysis for C$_{32}$H$_{39}$N$_1$O$_4$: Calcd: C, 76.62; H, 7.84; N, 2.79. Found: C, 76.28; H, 8.05: N, 2.55.

Reference Example 10

(2S,3S)-3-Hydroxy-2-((1S)-2-hydroxy-1-phenyl-ethylamino)-4-methyl-pentanoic acid tert-butyl ester

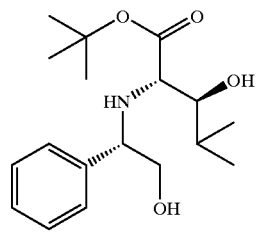

A solution of (2S,3S)-2-((4R)-2-benzhydryl-4-phenyl-oxazolidin-3-yl)-3-hydroxy-4-methyl-pentanoic acid tert-butyl ester (600 mg, 1.196 mmole, obtained from Reference Example 11) in a mixture of tetrahydrofuran : water: formic acid (3:1:1) was stirred at room temperature for 20 h. The volatile was removed in vacuo, and the residue was dissolved in aqueous sodium bicarbonate solution. The aqueous layer was extracted with ethyl acetate (3 times), and the extracts were combined, washed with saturated sodium chloride solution, dried over magnesium sulfate, filtered and concentrated in vacuo. The residue was chromatographed (flash column, silica gel, methylene chloride:methanol:diethyl ether=90:2:10) to give (2S,3S)-3-hydroxy-2-((1S)-2-hydroxy-1-phenyl-ethylamino)-4-methyl-pentanoic acid tert-butyl ester as a white solid (211 mg, 55%).

MS (ES): m/z 323.9 (M+H).

IR cm$^{-1}$: 3340, 2977, 1729.

H-NMR (δ, DMSO-d$_6$): 7.571–7.191 (5H, m), 4.698 (1H, t, J=5.4 Hz), 4.595 (1H, d, J=6.3 Hz), 3.641 (1H, t, J=6.3 Hz), 3.418 (1H, t, J=5.7 Hz), 3.299–3.259 (1H, m), 3.061 (1H, d, J=6.0 Hz), 1.890–1.804 (1H, m), 1.498–1.415 (2H, bs), 1.318 (9H, s), 0.842 (3H, d, J=6.3 Hz), 0.82 (3H, d, J=6.3 Hz).

Analysis for $C_{18}H_{29}NO_4$: Calcd: C, 66.84; H, 9.04; N, 4.33. Found: C, 66.63; H, 8.85: N, 4.07.

Reference Example 11

(2S,3S)-2-Amino-3-hydroxy-4-methyl-pentanoic acid tert-butyl ester

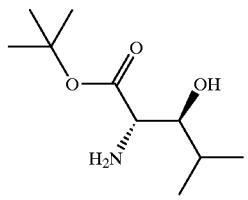

(2S,3S)-3-Hydroxy-2-((1S)-2-hydroxy-1-phenyl-ethylamino)-4-methyl-pentanoic acid tert-butyl ester (450 mg, 1.39 mmole, obtained from Reference Example 12) was hydrogenated using 10% palladium on carbon (120 mg) in methanol (100 ml) under atmospheric pressure at room temperature. The catalyst was removed by filtration, and the filtrate was concentrated in vacuo. The residue was chromatographed (flash column, silica gel, 20–30% methanol in diethyl ether) to give (2S,3S)-2-amino-3-hydroxy-4-methyl-pentanoic acid tert-butyl ester as a white solid (246 mg, 87%).

MS (ES): m/z 203.8 (M+H).

H-NMR (δ, DMSO-$d_6$): 4.569 (1H, d, J=5.7 Hz), 3.218–3.160 (3H, m), 3.113 (1H, d, J=6.3 Hz), 1.916–1.806 (1H, m), 1.403 (9H, s), 0.869 (3H, d, J=6.9 Hz), 0.815 (3H, d, J=6.9 Hz).

Analysis for $C_{10}H_{21}NO_3$: Calcd: C, 59.09; H, 10.41; N, 6.89. Found: C, 59.08; H, 10.33: N, 6.74.

Reference Example 12 tert-Butyl (2S,3S)-2-{[(benzyloxy)carbonyl]amino}-3-hydroxy-4-methylpentanoate

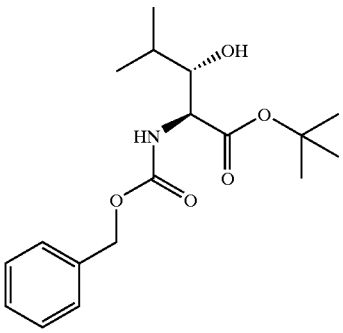

A solution of (2S,3S)-2-amino-3-hydroxy-4-methyl-pentanoic acid tert-butyl ester (297 mg, 1.37 mmol) and triethylamine (139 mg, 1.37 mmol) in anhydrous methylene chloride (2 ml) was cooled to 0° C. under a nitrogen atmosphere. To this solution was added N-(benzyloxycarbonyloxy)-succinimide (343 mg, 1.37 mmol). The resulting mixture was warmed to room temperature and stirred for 15 hours. The reaction mixture was partitioned between ether and water. The organic layer was washed with cold 1N hydrochloric acid and saturated sodium chloride, dried over magnesium sulfate, filtered and concentrated in vacuo, to provide tert-butyl (2S,3S)-2-{[(benzyloxy)carbonyl]-amino}-3-hydroxy-4-methylpentanoate (445 mg, 96%) as a yellow oil.

MS (ES): m/z 338.4 (M+H).

IR cm$^{-1}$: 3436, 2976, 1722.

$^1$H NMR (δ, CDCl$_3$): 7.37–7.28 (m, 5H), 5.70 (d, J=6.9, 1H), 5.12 (s, 2H), 4.40 (dd, J=3.17, 1H), 3.46 (bs, 1H), 2.56 (d, 7.35 Hz, 1H), 1.81–1.69 (m, 1H), 1.48 (s, 9H), 1.02 (d, J=6.6 Hz, 3H), 0.98 (d, J=6.72 Hz, 3H).

Reference Example 13

[1-(3,3-Diethoxy-propylcarbamoyl)-2-hydroxy-3-methyl-butyl]-carbamic acid benzyl ester

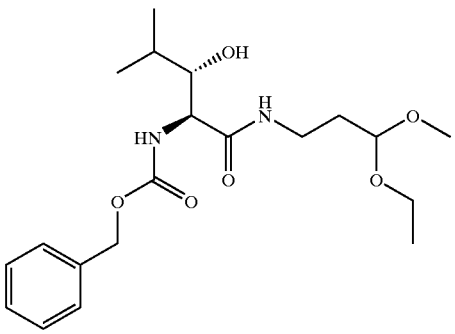

A solution of tert-butyl (2S,3S)-2-{[(benzyloxy)carbonyl]amino}-3-hydroxy-4-methylpentanoate (400 mg, 1.19 mmol) in methylene chloride (7 ml) was cooled to 0° C. under nitrogen atmosphere. To this solution was added trifluoroacetic acid (10 ml), and the resulting mixture was warmed up to room temperature and stirred for 2.5 hours. The volatiles were removed in vacuo to provide (2S,3S)-2-{[(benzyloxy)carbonyl]amino}-3-hydroxy-4-methylpentanoic acid (368 mg, 100%) as an orange oil.

To a solution of (2S,3S)-2-{[(benzyloxy)carbonyl]amino}-3-hydroxy-4-methylpentanoic acid (368 mg, 1.31 mmol) in anhydrous tetrahydrofuran (5 ml) was added hydroxybenzotriazole (177 mg, 1.31 mmol) and 1-(3-dimethylaminopropyl)-3-ethylcarbodiimide hydrochloride (251 mg, 1.31 mmol). The resulting solution was stirred at room temperature under nitrogen for 30 minutes. A solution of 1-amino-3,3-diethoxypropane (183 mg, 1.25 mmol) in tetrahydrofuran (2 ml) and N,N-diisopropylethylamine (0.228 ml, 169 mg, 1.31 mmol) were added and stirred at room temperature for 15 hours. The reaction mixture was partitioned between ethyl acetate (75 ml) and water (40 ml). The organic layer was separated, and the aqueous layer was extracted with ethyl acetate (2×75 ml). The combined extracts were washed with 2% cold hydrochloric acid, saturated sodium bicarbonate solution and saturated sodium chloride, dried over magnesium sulfate, filtered and concentrated in vacuo to provide [1-(3,3-diethoxy-propylcarbamoyl)-2-hydroxy-3-methyl-butyl]-carbamic acid benzyl ester (407 mg, 79%) as a white solid.

MS (ES): m/z 411.3 (M+H).

IR cm$^{-1}$: 3300, 1693, 1647.

$^1$H NMR (δ, CDCl$_3$): 7.39–7.28 (m, 5H), 6.75 (bs, 1H), 5.79 (d, J=8.4 Hz, 1H), 5.11 (bs, 2H), 4.55 (t, J=5.16 Hz, 1H), 4.12 (dd, J=4.23 Hz, 1H), 3.71–3.63 (m, 3H), 3.53–3.44 (m, 2H), 3.39–3.27 (m, 3H), 1.85–1.75 (m, 3H), 1.21 (2t, 6H), 1.01 (d, J=6.6 Hz, 3H), 0.94 (d, J=6.75 Hz, 3H).

Reference Example 14

[2-Hydroxy-3-methyl-1-(3-oxo-propylcarbamoyl)-butyl]-carbamic acid benzyl ester

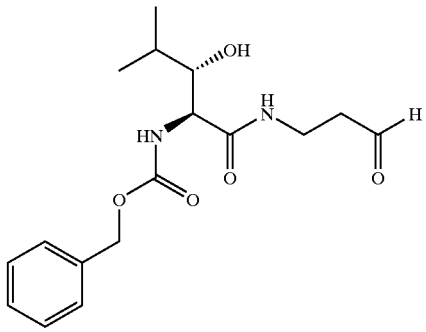

To a solution of [1-(3,3-diethoxy-propylcarbamoyl)-2-hydroxy-3-methyl-butyl]-carbamic acid benzyl ester (350 mg, 0.854 mmol) in anhydrous tetrahydrofuran (2 ml) was added 0.5N hydrochloric acid (2 ml). The resulting solution was stirred for 20 minutes at room temperature. The aqueous layer was basified to pH 8 with sodium bicarbonate solution, and extracted with ethyl acetate (3×40 mL). The combined extracts were washed with saturated sodium chloride, dried over magnesium sulfate, filtered and concentrated in vacuo to provide [2-hydroxy-3-methyl-1-(3-oxo-propylcarbamoyl)-butyl]-carbamic acid benzyl ester (266 mg, 93%) as a white solid.

MS (ES): m/z 337.5 (M+H).

IR cm$^{-1}$: 3303, 1694, 1647.

$^1$H NMR (δ, CDCl$_3$): 9.74 (s, 1H), 7.39–7.29 (m, 5H), 6.74 (bs, 1H), 5.81 (d, J=8.04 Hz, 1H), 5.11 (s, 2H), 4.11 (dd, J=4.34, 1H), 3.56–3.52 (m, 3H), 3.35–3.28 (m, 1H), 2.68 (t, J=5.84 Hz, 2H), 1.83–1.72 (m, 1H), 1.01 (d, J=6.57 Hz, 3H), 0.92 (d, J=6.78 Hz, 3H).

Reference Example 15

[(1S)-1-(3,3-Diethoxy-propylcarbamoyl)-3-methyl-butyl]-carbamic acid benzyl ester

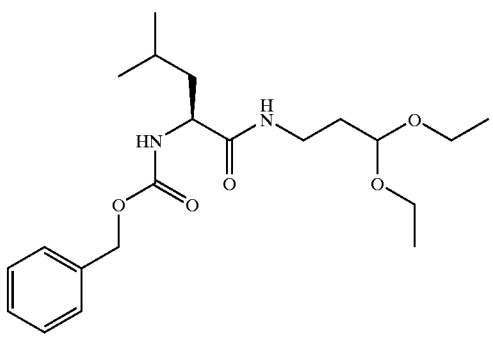

By using an analogous procedure to that described for Reference Example 13, Z-leucine (1.92 g, 7.24 mmol), hydroxybenzotriazole (980 mg, 7.24 mmol), 1-(3-dimethylaminopropyl)-3-ethylcarbodiimide hydrochloride (1.39 g, 7.24 mmol), 1-amino-3,3-diethoxypropane (1.01 g, 6.9 mmol), and N,N-diisopropylethylamine (1.26 ml, 7.24 mmol) were reacted at room temperature in anhydrous tetrahydrofuran (40 ml) for 16 hours, to provide [(1S)-1-(3,3-diethoxy-propylcarbamoyl)-3-methyl-butyl]-carbamic acidbenzyl ester (2.67 g, 98%) as a pale yellow solid.

MS (ES): m/z 395.3 (M+H).

IR cm$^{-1}$: 3301, 1685, 1649.

$^1$H NMR (δ, CDCl$_3$): 7.36–7.32 (m, 5H), 6.53 (bs, 1H), 5.15 (bs, 1H), 5.10 (bs, 2H), 4.55 (t, J=5.03 Hz, 1H), 4.16–4.11 (m, 1H), 3.70–3.62 (m, 2H), 3.54–3.45 (m, 2H), 3.38–3.29 (m, 2H), 1.82 (q, J=5.75 Hz, 2H), 1.69–1.59 (m, 2H), 1.55–1.43 (m, 1H), 1.24–1.15 (m, 6H), 0.93 (d, J=6.24 Hz, 6H).

Analysis for C$_{21}$H$_{34}$N$_2$O$_5$: Calcd: C, 63.94; H, 8.69; N, 7.10. Found: C, 63.92; H, 8.49; N, 7.12.

Reference Example 16

[(1S)-3-Methyl-1-(3-oxo-propylcarbamoyl)-butyl]-carbamic acid benzyl ester

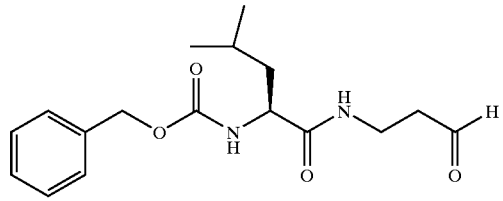

By using an analogous procedure to that described for Reference Example 14, [(1S)-1-(3,3-diethoxy-propylcarbamoyl)-3-methyl-butyl]-carbamic acid benzyl ester (1.0 g, 2.5 mmol, obtained from Reference Example 15) in tetrahydrofuran was reacted with 0.5N hydrochloric acid (5 mL) for 15 min, to provide [(1S)-3-methyl-1-(3-oxo-propylcarbamoyl)-butyl]-carbamic acid benzyl ester (906 mg, 100%) as a white solid.

MS (ES): m/z 321.3 (M+H).

IR cm$^{-1}$: 3309, 1683, 1655.

$^1$H NMR (δCDCl$_3$): 9.76 (bs, 1H), 7.39–7.29 (m, 5H), 6.48 (bs, 1H), 5.17 (bs, 1H), 5.10 (bs, 2H), 4.14–4.10 (m, 1H), 3.54–3.50 (m, 2H), 2.70 (t, J=5.03 Hz, 2H), 1.69–1.57 (m, 2H), 1.53–1.43 (m, 2H), 0.92 (d, J=6.18 Hz, 6H).

Analysis for C$_{17}$H$_{24}$N$_2$O$_4$: Calcd: C, 63.73; H, 7.55; N, 8.74. Found: C, 63.62; H, 7.73; N, 8.79.

Reference Example 17

[(1S,2S)-1-(3,3-Diethoxy-propylcarbamoyl)-2-hydroxy-propyl]-carbamic acid benzyl ester

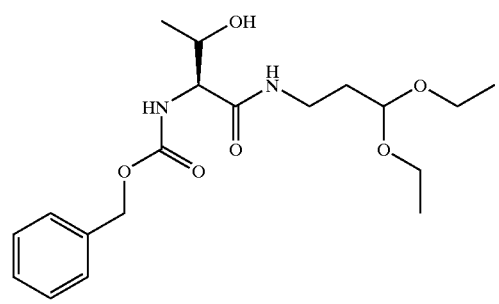

By using an analogous procedure to that described for Reference Example 13, Z-threonine (5 g, 19.74 mmol), hydroxybenzotriazole (2.67 g, 19.74 mmol), 1-(3- dimethylaminopropyl)-3-ethylcarbodiimide hydrochloride (3.79 g, 19.74 mmol), 1-amino-3,3-diethoxypropane (2.78 g, 18.8 mmol) and N,N-diisopropylethylamine (3.44 mL, 19.74 mmol) were reacted in anhydrous tetrahydrofuran (75 mL) at room temperature for 16 h, to provide [(1S,2S)-1-(3,3-diethoxy-propylcarbamoyl)-2-hydroxy-propyl]-carbamic acid benzyl ester (6.52 g, 91%) as a white solid.

MS (ES): m/z 383.3 (M+H).

IR cm$^{-1}$: 3283, 1695, 1646.

$^1$H NMR (δCDCl$_3$): 7.40–7.29 (m, 5H), 6.90 (bs, 1H), 5.67 (d, J=8.25 Hz, 1H), 5.13 (bs, 2H), 4.55 (t, J=5.13 Hz, 1H), 4.40–4.36 (m, 1H), 4.05 (dd, J=1.86, 1H), 3.70–3.63 (m, 2H), 3.52–3.46 (m, 2H), 3.39–3.34 (m, 2H), 3.11 (bs, 1H), 1.82 (q, J=6.12 Hz, 2H), 1.23–1.16 (m, 9H).

Analysis for C$_{19}$H$_{30}$N$_2$O$_6$: Calcd: C, 59.67; H, 7.91; N, 7.32. Found: C, 59.60; H, 8.05; N, 7.32.

Reference Example 18

[(1S,2S)-2-Hydroxy-1-(3-oxo-propylcarbamoyl)-propyl]-carbamic acid benzyl ester

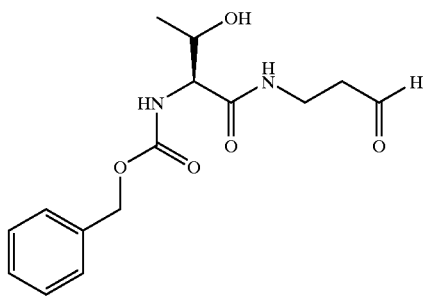

By using an analogous procedure to that described for Reference Example 14, [(1S,2S)-1-(3,3-diethoxy-propylcarbamoyl)-2-hydroxy-propyl]-carbamic acid benzyl ester (2 g, 5.24 mmol, obtained from Reference Example 17) in tetrahydrofuran (10 ml) was reacted with 0.5 N hydrochloric acid (10 ml) for 30 minutes at room temperature, to provide [(1S,2S)-2-hydroxy-1-(3-oxo-propylcarbamoyl)-propyl]-carbamic acid benzyl ester (1.56 g, 97%) as a white solid.

MS (ES): m/z 309.2 (M+H).

IR cm$^{-1}$: 3314, 1689, 1643.

$^1$H NMR (δCDCl$_3$): 9.76 (s, 1H), 7.40–7.26 (m, 5H), 6.89 (bs, 1H), 5.71 (bs, 1H), 5.14 (s, 2H), 4.37–4.35 (m, 1H), 4.04 (dd, J=1.85 Hz, 1H), 3.55 (q, J=6.02 Hz, 2H), 3.08 (bs, 1H), 2.70 (t, J=5.87 Hz, 2H), 1.16 (d, J=6.45 Hz, 3H).

Analysis for C$_{15}$H$_{20}$N$_2$O$_5$: Calcd: C, 58.43; H, 6.54; N, 9.09. Found: C, 58.45; H, 6.71; N, 8.85.

Reference Example 19

Benzyl (1S)-2-[(3,3-diethoxypropyl)amino]-1-methyl-2-oxoethylcarbamate

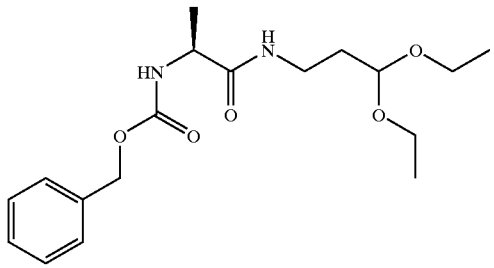

By using an analogous procedure to that described for Reference Example 13, carbobenzyloxy-L-alanine (2 g, 8.99 mmol), hydroxybenzotriazole (1.2 g, 8.99 mmol), 1-(3-dimethylaminopropyl)-3-ethylcarbodiimide hydrochloride (1.72 g, 8.99 mmol), 1-amino-3,3-diethoxypropane (1.25 g, 8.53 mmol) and N,N-diisopropylethylamine (1.56 ml, 8.99 mmol) were reacted in anhydrous tetrahydrofuran (40 ml) at room temperature for 16 h, to provide benzyl (1S)-2-[(3,3-diethoxypropyl)amino]-1-methyl-2-oxoethylcarbamate (2.55 g, 85%) as a pale yellow solid.

MS (ES): m/z 353.4 (M+H).

IR cm$^{-1}$: 3298, 1684, 1649.

$^1$H NMR (δDMSO-d$_6$): 7.79 (s, 1H), 7.40–7.29 (m, 6H), 5.01 (bs, 2H), 4.48 (t, J=5.54 Hz, 1H), 4.01–3.92 (m, 1H), 3.60–3.50 (m, 2H), 3.46–3.36 (m, 2H), 3.08 (q, J=5.93 Hz, 2H), 1.64 (q, J=6.72 Hz, 2H), 1.18 (d, J=7.14 Hz, 3H), 1.10 (2t, 6H).

Analysis for C$_{18}$H$_{28}$N$_2$O$_5$: Calcd: C, 61.34; H, 8.01; N, 7.95. Found: C, 61.05; H, 7.85; N, 8.27.

Reference Example 20

Benzyl (1S)-1-methyl-2-oxo-2-[(3-oxopropyl)amino]ethylcarbamate

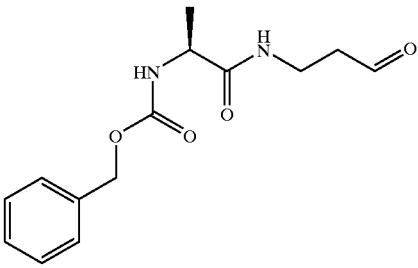

By using an analogous procedure to that described for Reference Example 14, benzyl (1S)-2-[(3,3-diethoxypropyl)amino]-1-methyl-2-oxoethylcarbamate (2.39 g, 6.79 mmol, obtained from Reference Example 19) in tetrahydrofuran (14 ml) was reacted with 0.5 N hydrochloric acid (14 ml) for 45 minutes, to provide benzyl (1S)-1-methyl-2-oxo-2-[(3-oxopropyl)amino]ethylcarbamate (1.92 g, 100%) as a pale yellow waxy solid.

MS (ES): m/z 279.3 (M+H).

IR cm$^{-1}$: 3301, 1686, 1648.

$^1$H NMR (δDMSO-d$_6$): 9.62 (s, 1H), 7.95 (t, J=5.42 Hz, 1H), 7.41–7.29 (m, 6H), 5.01 (bs, 2H), 4.04–3.91 (m, 1H), 3.39–3.24 (m, 2H), 2.56–2.49 (m, 2H), 1.16 (d, 7.14 Hz, 3H).

Analysis for $C_{14}H_{18}N_2O_4$: Calcd: C, 60.42; H, 6.52; N, 10.07. Found: C, 60.40; H, 6.69; N, 10.00.

Reference Example 21

Benzyl (1S)-1-benzyl-2-[(3,3-diethoxypropyl)amino]-2-oxoethylcarbamate

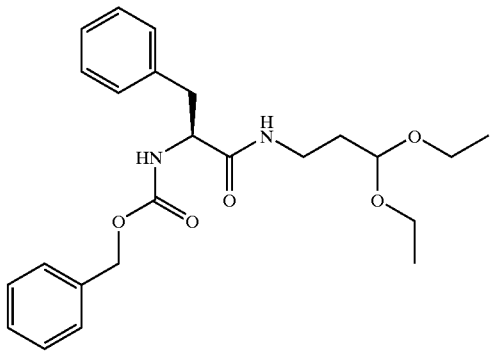

By using an analogous procedure to that described for Reference Example 13, N-(carbobenzyloxy)-L-phenylalanine (2 g, 6.68 mmol), hydroxybenzotriazole (903 mg, 6.68 mmol), 1-(3-dimethylaminopropyl)-3-ethylcarbodiimide hydrochloride 1.28 g, 6.68 mmol), 1-amino-3,3-diethoxypropane (935 mg, 6.36 mmol) and N,N-diisopropylethylamine (1.16 mL, 6.68 mmol) were reacted in anhydrous tetrahydrofuran (32 mL) at room temperature for 16 h, to provide benzyl (1S)-1-benzyl-2-[(3,3-diethoxypropyl)amino]-2-oxoethylcarbamate (2.5 g, 92%) as a white solid.

MS (ES): m/z 429.5 (M+H).

IR cm$^{-1}$: 3292, 1694, 1647, 1544.

$^1$H NMR ($\delta$DMSO-d$_6$): 7.94 (t, J=5.33 Hz, 1H), 7.48 (d, J=8.55 Hz, 11H), 7.35–7.18 (m, 10H), 4.95 (bs, 2H), 4.45 (t, J=5.55 Hz, 1H), 4.21–4.13 (m, 1H), 3.60–3.35 (m, 2H), 3.46–3.35 (m, 2H), 3.14–3.02 (m, 2H), 2.97–2.71 (m, 2H), 1.61 (q, J=6.63 Hz, 2H), 1.10 (2t, 6H).

Analysis for $C_{24}H_{32}N_2O_5$: Calcd: C, 67.27; H, 7.53; N, 6.54. Found: C, 67.23; H 7.57; N, 6.57.

Reference Example 22

Benzyl (1S)-1-benzyl-2-oxo-2-[(3-oxopropyl)amino]ethylcarbamate

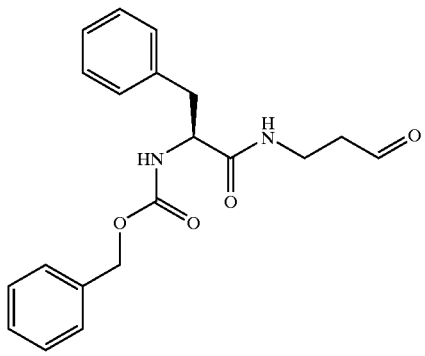

By using an analogous procedure to that described for Reference Example 14, 1-benzyl-2-[(3,3-diethoxypropyl)amino]-2-oxoethylcarbamate (2.37 g, 5.54 mmol, obtained from Reference Example 21) in tetrahydrofuran (11 ml) was reacted with 0.5 N hydrochloric acid (11 ml) for 45 minutes at room temperature, to provide benzyl (1S)-1-benzyl-2-oxo-2-[(3-oxopropyl)amino]ethylcarbamate (1.84 g, 94%) as a white solid.

MS (ES): m/z 355.4 (M+H).

IR cm$^{-1}$: 3306, 1687, 1649, 1533.

$^1$H NMR ($\delta$DMSO-d$_6$): 9.60 (s, 1H), 8.11 (t, J=5.51 Hz, 1H), 7.49 (d, J=8.49 Hz, 1H), 7.36–7.17 (m, 10H), 4.95 (bs, 2H), 4.20–4.13 (m, 1H), 3.42–3.24 (m, 4H), 2.95–2.69 (m, 2H).

Analysis for $C_{20}H_{22}N_2O_4$: Calcd: C, 67.78; H, 6.26; N, 7.90. Found: C, 67.38; H, 6.30; N, 7.54.

Reference Example 23

Benzyl (3S)-3-{[(benzyloxy)carbonyl]amino}-4-[(3,3-diethoxypropyl)amino]-4-oxobutanoate

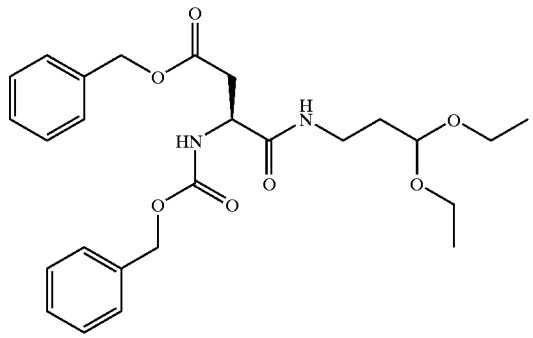

By using an analogous procedure to that described for Reference Example 13, benzyloxycarbonyl-L-aspartic acid [1-benzyl ester (2 g, 5.6 mmol), hydroxybenzotriazole (756 mg, 5.6 mmol), 1-(3-dimethylaminopropyl)-3-ethylcarbodiimide hydrochloride (1.07 g, 5.6 mmol), 1-amino-3,3-diethoxypropane (784 mg, 5.3 mmol) and N,N-diisopropylethylamine (0.986 mL, 5.6 mmol) were reacted in anhydrous tetrahydrofuran (30 ml) at room temperature for 16 hours, to provide benzyl (3S)-3-{[(benzyloxy)carbonyl]amino}-4-[(3,3-diethoxypropyl)amino]-4-oxobutanoate (2.81 g, 100%) as a pale yellow waxy solid.

MS (ES): m/z 504.4 (M+NH$_4$).

IR cm$^{-1}$: 3287, 1729, 1716, 1688, 1644.

$^1$H NMR ($\delta$DMSO-d$_6$): 7.92–7.86 (m, 1H), 7.63–7.58 (m, 1H), 7.34 (bs, 10H), 5.08 (bs, 2H), 5.03 (bs, 2H), 4.47 (t, J=5.51 Hz, 1H), 4.41–4.34 (m, 1H), 3.59–3.38 (m, 4H), 3.08 (q, J=6.56 Hz, 2H), 2.85–2.57 (m, 2H), 1.64 (q, J=6.72 Hz, 2H), 1.10 (t, J=7.04 Hz, 6H).

Analysis for $C_{26}H_{34}N_2O_7$: Calcd: C, 64.18; H, 7.04; N, 5.76. Found: C, 63.16; H, 6.90; N, 6.77.

Reference Example 24

Benzyl (3S)-3-{[(benzyloxy)carbonyl]amino}-4-oxo-4-[(3-oxopropyl)amino]butanoate

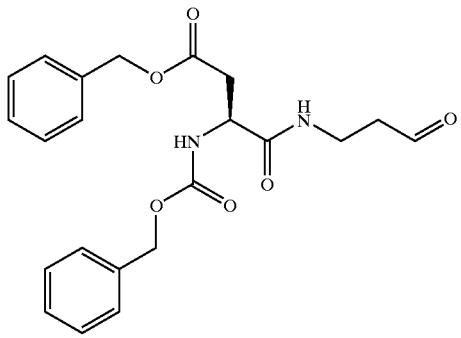

By using an analogous procedure to that described for Reference Example 14, benzyl (3S)-3-{[(benzyloxy)carbonyl]amino}-4-[(3,3-diethoxypropyl)amino]-4-oxobutanoate (2.63 g, 5.41 mmol, obtained from Reference Example 23) in tetrahydrofuran (11 ml) was reacted with 0.5 N hydrochloric acid at room temperature for 1 hour, to provide benzyl (3S)-3-{[(benzyloxy)carbonyl]amino}-4-oxo-4-[(3-oxopropyl)amino]butanoate (2.05 g, 92%) as a pale yellow waxy solid.

MS (ES): m/z 413.3 (M+H).

IR cm$^{-1}$: 3305, 1724, 1685, 1649.

$^1$H NMR (δDMSO-d$_6$): 9.61 (s, 1H), 8.07 (t, 5.34 Hz, 1H), 7.61 (d, 8.22, 1H), 7.35–7.31 (m, 10H), 5.07–4.98 (m, 5H), 4.40–4.33 (m, 2H), 2.80–2.73 (m, 2H), 2.64–2.56 (m, 2H).

Analysis for C$_{22}$H$_{24}$N$_2$O$_6$: Calcd: C, 64.07; H, 5.87; N, 6.79. Found: C, 63.09; H, 5.97; N, 6.30.

Reference Example 25 tert-Butyl (4S)-4-{[(benzyloxy)carbonyl]amino}-5-[(3,3-diethoxypropyl)amino]-5-oxopentanoate

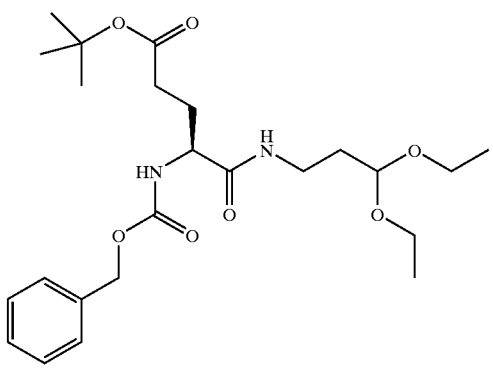

By using an analogous procedure to that described for Reference Example 13, benzyloxycarbonyl-L-glutamic acid □-t-butyl ester (2 g, 5.93 mmol), hydroxybenzotriazole (801 mg, 5.93 mmol), 1-(3-dimethylaminopropyl)-3-ethylcarbodiimide hydrochloride (1.14 g, 5.93 mmol), 1-amino-3,3-diethoxypropane (830 mg, 5.65 mmol), and N,N-diisopropylethylamine (1.03 mL, 5.93 mmol) were reacted in anhydrous tetrahydrofuran (30 mL) at room temperature for 16 hours, to provide tert-butyl (4S)-4-{[(benzyloxy)carbonyl]amino}-5-[(3,3-diethoxypropyl)amino]-5-oxopentanoate (2.92 g, 100%) as a yellow waxy solid.

MS (ES): m/z 467.3 (M+H).

IR cm$^{-1}$: 3289, 2975, 1725, 1689, 1649, 1539.

$^1$H NMR (δDMSO-d$_6$): 7.85 (t, J=5.49, 1H), 7.40–7.31 (m, 6H), 5.02 (bs, 2H), 4.48 (t, J=5.52 Hz, 1H), 3.97–3.89 (m, 1H), 3.60–3.50 (m, 2H), 3.46–3.38 (m, 2H), 3.15–3.04 (m, 2H), 2.20 (t, J=7.68 Hz, 2H), 1.91–1.59 (m, 4H), 1.38 (s, 9H), 1.10 (t, J=6.99, 6H).

Analysis for C$_{24}$H$_{38}$N$_2$O$_7$: Calcd: C, 61.78; H, 8.21; N, 6.00. Found: C, 60.03; H, 7.92; N, 6.19.

Reference Example 26 tert-Butyl (4S)-4-{[(benzyloxy)carbonyl]amino}-5-oxo-5-[(3-oxopropyl)amino]pentanoate

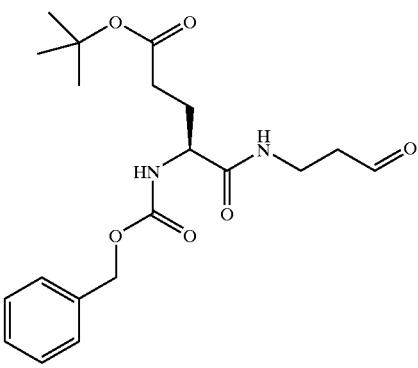

By using an analogous procedure to that described for Reference Example 14, tert-butyl (4S)-4-{[(benzyloxy)carbonyl]amino}-5-[(3,3-diethoxypropyl)amino]-5-oxopentanoate (2.75 g, 5.9 mmol, obtained from Reference Example 25) in tetrahydrofuran (12 ml) was reacted with 0.5 N hydrochloric acid (12 ml) for 1 hour at room temperature, to provide tert-butyl (4S)-4-{[(benzyloxy)carbonyl]amino}-5-oxo-5-[(3-oxopropyl)amino]pentanoate (2.1 g, 91%) as a pale yellow solid.

MS (ES): m/z 393.2 (M+H).

IR cm$^{-1}$: 3358, 3126, 2935, 1634.

¹H NMR (δDMSO-d₆): 9.62 (s, 1H), 7.99 (t, J=5.61 Hz, 1H), 7.40–7.29 (m, 6H), 5.02 (bs, 2H), 3.99–3.89 (m, 1H), 3.4–3.35 (m, 2H), 2.57–2.48 (m, 2H), 2.19 (t, J=7.7 Hz, 2H), 1.89–1.59 (m, 2H), 1.51 (s, 9H).

Analysis for $C_{20}H_{28}N_2O_6$: Calcd: C, 61.21; H, 7.19; N, 7.14. Found: C, 60.58; H, 6.97; N, 6.97.

Reference Example 27

Benzyl (5S)-[5-benzyloxycarbonylamino-5-(3,3-diethoxy-propylcarbamoyl)-pentyl]-carbamate

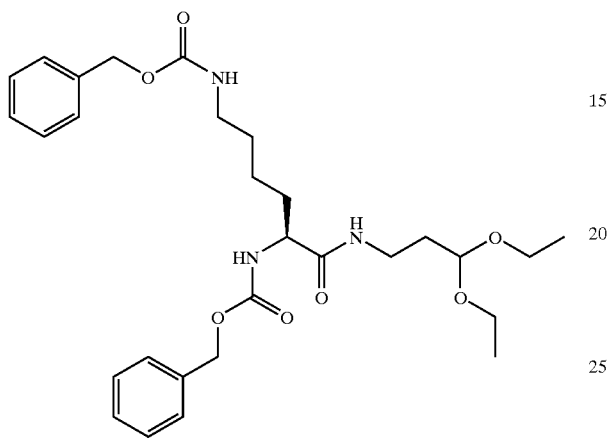

By using an analogous procedure to that described for Reference Example 13, $N^α,N^ε$ dibenzyloxycarbonyl-L-lysine (2 g, 4.83 mmol), hydroxybenzotriazole (652 mg, 4.83 mmol), 1-(3-dimethylaminopropyl)-3-ethylcarbodiimide hydrochloride (925 mg, 4.83 mmol), 1-amino-3,3-diethoxypropane (676 mg, 4.6 mmol) and N,N-diisopropylethylamine (0.84 mL, 4.83 mmol) were reacted in anhydrous terahydrofuran (26 mL) at room temperature for 16 hours, to provide benzyl (5S)-[5-benzyloxycarbonylamino-5-(3-diethoxy-propylcarbamoyl)-pentyl]-carbamate (2.68 g, 100%) as a white waxy solid.

MS (ES): m/z 566.1 (M+Na).

IR cm⁻¹: 3288, 1688, 1637, 1538.

¹H NMR (δDMSO-d₆): 7.83 (t, J=5.51 Hz, 1H), 7.38–7.27 (m, 11H), 7.21 (t, J=5.48 Hz, 1H), 5.00 (bs, 4H), 4.48 (t, J=5.5 Hz, 1H), 3.87 (q, J=8.27 Hz, 1H), 3.60–3.52 (m, 2H), 3.46–3.38 (m, 2H), 3.09–3.03 (m, 2H), 2.99–2.92 (m, 2H), 1.67–1.23 (m, 8H), 1.10 (2t, 6H).

Analysis for $C_{29}H_{41}N_3O_7$: Calcd: C, 64.07; H, 7.60; N, 7.73. Found: C, 63.76; H, 7.24; N, 7.95.

Reference Example 28

Benzyl (5S)-[5-benzyloxycarbonylamino-5-(3-oxo-propylcarbamoyl)-pentyl]-carbamate

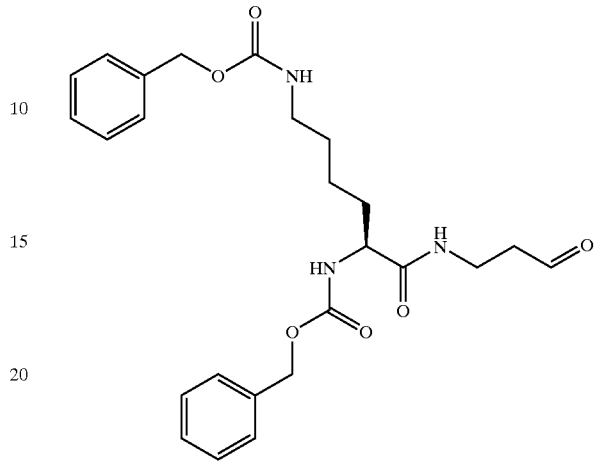

By using an analogous procedure to that described for Reference Example 14, benzyl (5S)-[5-benzyloxycarbonylamino-5-(3-diethoxy-propylcarbamoyl)-pentyl]-carbamate (2.217 g, 4.08 mmol, obtained from Reference Example 27) in tetrahydrofuran (20 ml) was reacted with 0.5 N hydrochloric acid (20 ml) at room temperature for 2.5 hours to provide benzyl (5S)-[5-benzyloxycarbonylamino-5-(3-oxo-propylcarbamoyl)-pentyl]-carbamate (1.88 g, 98%) as a white solid.

MS (ES): m/z 470.2 (M+H).

IR cm⁻¹: 3324, 1689, 1643.

¹H NMR (δDMSO-d₆): 9.62 (s, 1H), 7.98 (t, J=5.6 Hz, 1H), 7.39–7.27 (m, 11H), 7.20 (t, J=5.52 Hz, 1H), 5.00 (bs, 4H), 3.90–3.83 (m, 1H), 2.95 (q, J=6.57 Hz, 2H), 2.56–2.49 (m, 5H), 1.57–1.20 (m, 6H).

Analysis for $C_{25}H_{31}N_3O_6$: Calcd: C, 63.95; H, 6.65; N, 8.95. Found: C, 63.76; H, 6.14; N, 8.68.

Reference Example 29

9H-Fluoren-9-ylmethyl 11-[(3,3-diethoxypropyl)amino]-1-oxoundecylcarbamate

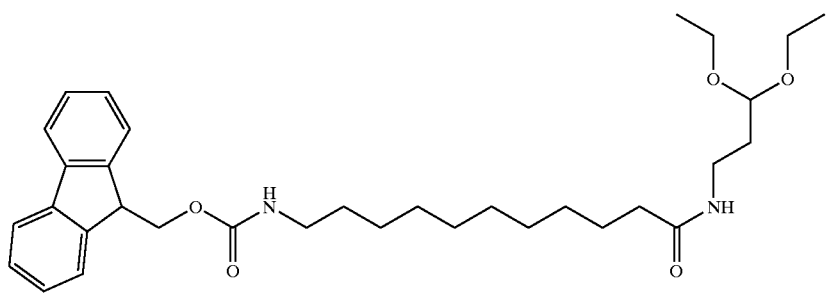

By using an analogous procedure to that described for Reference Example 13, Fmoc-11-aminoundecanoic acid (2 g, 4.7 mmol), hydroxybenzotriazole (639 mg, 4.7 mmol), 1-(3-dimethylaminopropyl)-3-ethylcarbodiimide hydrochloride (906 mg, 4.7 mmol), 1-amino-3,3-diethoxypropane (662 gm, 4.5 mmol) and N,N-diisopropylethylamine (0.834 ml, 4.7 mmol) were reacted in anhydrous tetrahydrofuran (30 ml) at room temperature for 16 hours. Purification by chromatography (flash column, silica gel, 50–80% ethyl acetate in hexanes then 10% methanol in methylene chloride) provided 9H-fluoren-9-ylmethyl 11-[(3,3-diethoxypropyl)amino]-11-oxoundecyl-carbamate (560 mg, 23%) as a white solid.

MS (ES): m/z 553.1 (M+H).

IR cm$^{-1}$: 1687, 1645, 1532.

$^1$H NMR (δDMSO-d$_6$): 7.89 (d, 7.41 Hz, 2H), 7.74–7.67 (m, 3H), 7.44–7.23 (m, 5H), 4.47 (t, 5.63 Hz, 1H), 4.29 (d, 6.66 Hz, 2H), 4.22–4.18 (m, 1H), 3.60–3.50 (m, 2H), 3.46–3.36 (m, 2H), 3.04 (q, 6.8 Hz, 2H), 2.96 (q, 6.57 Hz, 2H), 2.02 (t, 7.34 Hz, 2H), 1.62 (q, 6.8 Hz, 2H), 1.48–1.44 (m, 2H), 1.38–1.31 (m, 2H), 1.23 (bs, 12H), 1.10 (t, 7.07 Hz, 6H).

Analysis for $C_{33}H_{48}N_2O_5$: Calcd: C, 71.71; H, 8.75; N, 5.07. Found: C, 71.40; H, 8.53; N, 5.03.

Reference Example 30

9H-Fluoren-9-ylmethyl 11-oxo-11-[(3-oxopropyl)amino]undecylcarbamate

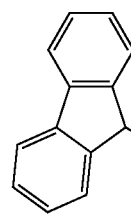

By using an analogous procedure to that described for Reference Example 14, 9H-fluoren-9-ylmethyl 11-[(3,3-diethoxypropyl)amino]-1-oxoundecylcarbamate (480 mg, 0.87 mmol, obtained from Reference Example 29) in tetrahydrofuran (5 ml) was reacted with 0.5 N hydrochloric acid (4 ml) at room temperature for 5 hours. Purification by chromatography (flash column, silica gel, 75% ethyl acetate in hexanes) provided 9H-fluoren-9-ylmethyl-11-oxo-11-[(3-oxopropyl)amino]undecyl-carbamate (348 mg, 84%) as a white waxy solid.

MS (ES): m/z 479.2 (M+H).

IR cm$^{-1}$: 3321, 1684, 1638, 1547.

$^1$H NMR (δDMSO-d$_6$): 9.62 (t, 1.74 Hz, 1H), 7.90–7.88 (m, 3H), 7.68 (d, 7.38 Hz, 2H), 7.44–7.24 (m, 5H), 4.29 (d, 6.6 Hz, 2H), 4.22–4.18 (m, 1H), 3.31–3.27 (m, 2H), 2.96 (q, 6.54 Hz, 2H), 2.55–2.49 (m, 2H), 2.03–1.98 (m, 2H), 1.47–1.38 (m, 4H), 1.22 (bs, 12H).

Analysis for $C_{29}H_{38}N_2O_4$: Calcd: C, 72.77; H, 8.00; N, 5.85. Found: C, 72.90; H, 7.80; N, 5.83.

Preparation of Dipeptide Ureas

Reference Example 31 tert-Butyl (2S)-5-{[(2,2-dioxido-2lambda~1~-diazanyl)(imino)methyl]amino}-2-{[(9H-fluoren-9-ylmethoxy)carbonyl]amino}pentanoate

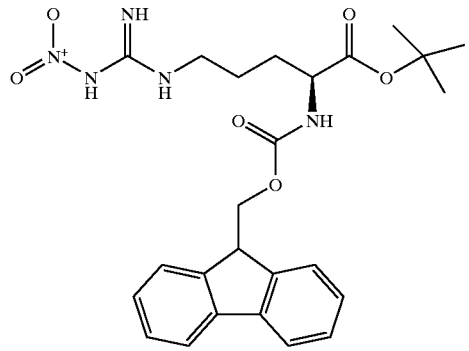

A suspension of N$^□$-Fmoc-N$^g$-nitro-L-arginine (1 g, 2.27 mmol) and sulfuric acid (5 drops) in anhydrous methylene chloride (75 ml) was saturated with isobutylene. The reaction mixture was gently stirred at room temperature for 48 hours. Saturated sodium carbonate (75 ml) was added to the reaction mixture. The organic layer was separated, washed with water, dried over magnesium sulfate, filtered and concentrated in vacuo, to provide tert-butyl (2S)-5-{[(2,2-dioxido-2lambda~1~-diazanyl)(imino)methyl]amino}-2-{[(9H-fluoren-9-ylmethoxy)carbonyl]amino}pentanoate (800 mg, 71%) as a pale tan solid.

MS (ES): m/z 498.3 (M+H).

IR cm$^{-1}$: 3313, 1721, 1628.

$^1$H NMR (δCDCl$_3$): 8.70 (bs, 1H), 7.77 (d, 7.47 Hz, 2H), 7.59–7.56 (m, 2H), 7.43–7.26 (m, 6H), 5.60 (d, 7.95 Hz, 1H), 4.42 (d, 6.96 Hz, 2H), 4.23–4.18 (m, 2H), 3.54–3.49 (m, 1H), 3.29–3.25 (m, 1H), 1.66–1.61 (m, 4H), 1.48 (bs, 9H).

Analysis for $C_{25}H_{31}N_5O_6$: Calcd: C, 60.35; H, 6.28; N, 14.08. Found: C, 62.01; H, 7.10; N, 12.40.

Reference Example 32 tert-Butyl (2S)-2-amino-5-{[(2,2-dioxido-2lambda~1~-do-2lambda~1~-diazanyl)(imino)methyl]amino}pentanoate

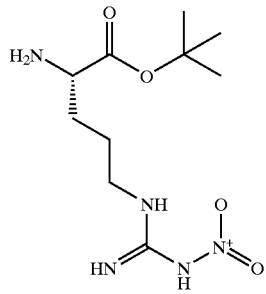

A solution of tert-butyl (2S)-5-{[(2,2-dioxido-2lambda~1~-diazanyl)(imino)methyl]amino}-2-{[(9H-fluoren-9-ylmethoxy)carbonyl]amino}pentanoate (627 mg, 1.26 mmol, obtained from Reference Example 31) in piperidine (30 ml) was stirred at room temperature under a nitrogen atmosphere for 1 hour. The reaction mixture was poured into cold water (250 ml) and filtered. The filtrate was extracted with ethyl acetate (3×75 ml), and the combined extracts were dried over magnesium sulfate, filtered and concentrated in vacuo. The resulting residue was chromatographed (flash column, silica gel, 10% methanol in methylene chloride) to provide tert-butyl (2S)-2-amino-5-{[(2,2-dioxido-2lambda~1~-do-2lambda~1~-diazanyl)(imino)methyl]amino}pentanoate (268 mg, 77%) as a white amorphous solid.

MS (ES): m/z 276.4 (M+H).

IR cm$^{-1}$: 3303, 1726, 1629.

$^1$H NMR ($\delta$CDCl$_3$): 8.82 (bs, 1H), 8.04 (bs, 1H), 3.44–3.40 (m, 1H), 3.35–3.31 (m, 1H), 1.93–1.49 (m, 7H), 1.47 (s, 9H).

Reference Example 33 tert-Butyl (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoate

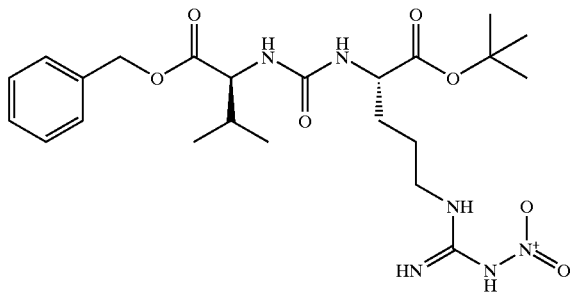

To a solution of triphosgene (595 mg, 2 mmol) in anhydrous methylene chloride (11 ml) was added dropwise a solution of L-valine benzyl ester 4-toluenesulfonate salt (2.06 g, 5.42 mmol) and N,N-diisopropylethylamine (2.2 mL) in methylene chloride (22 mL) over a period of 45 min under a nitrogen atmosphere, and the reaction mixture was stirred 5 min. To this reaction mixture were added a solution of tert-butyl (2S)-2-amino-5-{[(2,2-dioxido-2lambda~1~-do-2lambda~1~-diazanyl)-(imino)methyl]amino}pentanoate (1.49 g, 5.42 mmol, obtained from Reference Example 32) and a solution of N,N-diisopropylethylamine (2.2 ml) in methylene chloride (11 ml). After the reaction mixture was stirred for an additional 1.5 hours at room temperature, the volatiles were removed in vacuo, and the residue was diluted with ethyl acetate. The organic layer was washed with 10% potassium sulfate, 5% sodium bicarbonate, and saturated sodium chloride, dried over magnesium sulfate, filtered and concentrated in vacuo, to provide tert-butyl (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoate (2.58 g, 94%) as a pale orange amorphous solid.

MS (ES): m/z 509.2 (M+H).

IR cm$^{-1}$: 3352, 1736, 1628, 1557.

$^1$H NMR ($\delta$CDCl$_3$): 8.44 (bs, 1H), 7.73–7.61 (m, 2H), 7.34 (bs, 5H), 5.68 (d, 7.86 Hz, 1H), 5.51 (bs, 1H), 5.27–5.07 (m, 2H), 4.34 (q, 4.83 Hz, 2H), 3.37–3.34 (m, 1H), 2.23–2.12 (m, 2H), 1.65–1.49 (m, 4H), 1.46 (bs, 9H), 0.98–0.830 (m, 6H).

Analysis for C$_{23}$H$_{36}$N$_6$O$_7$: Calcd: C, 54.32; H, 7.13; N, 16.52. Found: C, 55.60; H, 7.24; N, 15.82.

Reference Example 34

(2S)-2-{[({(1S)-1-[(Benzyloxy)carbonyl]-2-methylpropyl}amino)carbonyl]amino}-5-{[(2,2-dioxido-2lambda~1~-diazanyl)(imino)methyl]amino}pentanoic acid

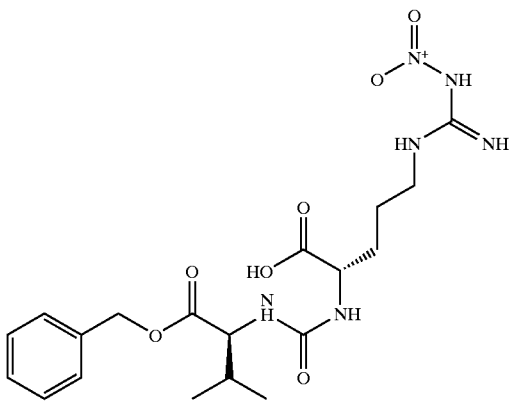

A solution of tert-butyl (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoate (1.25 g, 2.46 mmol) in anhydrous methylene chloride (12 ml) was cooled to 0° C. under a nitrogen atmosphere. Trifluroacetic acid (21 ml) was added, and the solution was warmed to room temperature and stirred for 2 hours. The volatiles were removed in vacuo, and the resultant residue was chromatographed (flash column, silica gel, 10% methanol in methylene chloride) to provide (2S)-2-{[({(1S)-1-[(benzyloxy)carbonyl]-2-methylpropyl}amino)carbonyl]amino}-5-{[(2,2-dioxido-2lambda~1~-diazanyl)-(imino)methyl]amino}pentanoic acid (885 mg, 80%) as a pale tan amorphous solid.

MS (ES): m/z 453.3 (M+H).

IR cm$^{-1}$: 3339, 1735, 1638, 1603.

$^1$H NMR ($\delta$DMSO-d$_6$): 8.15 (bs, 1H), 7.74 (b, 2H), 7.40–7.27 (m, 5H), 6.53 (bs, 2H), 5.14 (q, J=12.32 Hz, 2H), 4.40 (bs, 1H), 4.31 (bs, 1H), 1.87 (m, 2H), 1.77–1.63 (m, 4H), 0.94 (d, 6.84 Hz, 3H), 0.87 (d, 6.87 Hz, 3H).

Reference Example 35

[(3aR,4R,6aR)-6-Methoxy-2,2-dimethyltetrahydrofuro[3,4-d][1,3]dioxol-4-yl]methanol

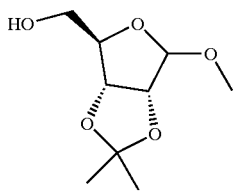

By using the known procedure (Barrett, A. G. M.; Lebold, S. A., *J. Org. Chem.*, 1990, 55, 3853), a solution of D-ribose (30 g, 0.2 mole, Aldrich) in anhydrous acetone (114 ml) and anhydrous methanol (114 ml) containing concentrated hydrogen chloride (3 ml) was heated at reflux for 10 hours. The resulting solution was cooled to room temperature, and the solvent was removed in vacuo. The residue was treated with pyridine to neutralize, and diluted with water. The aqueous layer was extracted with ethyl ether. The combined extracts were washed with aqueous sodium chloride solution, dried over magnesium sulfate, filtered and concentrated. The residue was distilled at b.p. 110° C. at 10 mmHg to give [(3aR,4R,6aR)-6-methoxy-2,2-dimethyltetrahydrofuro[3,4-d][1,3]dioxol-4-yl]methanol (30 g, 73.4%) as a pale yellow oil.

Mass (ES) m/z: 205.2 (M+H).

IR cm$^{-1}$: 3460, 2988, 2940, 1382.

H-NMR (δ, DMSO-d$_6$): 4.867 (1H, s), 4.809 (1H, t, J=6.0 Hz), 4.670 (1H, d), 4.528 (1H, d), 4.031–3.982 (1H, m), 3.440–3.322 (2H, m), 3.203 (3H, s), 1.374 (3H, s), 1.251 (3H, s).

Analysis for C$_9$H$_{16}$O$_5$: Calcd: C, 52.93; H, 7.90. Found: C, 52.61; H, 7.67.

Reference Example 36

[(3aR,4R,6aR)-6-Methoxy-2,2-dimethyltetrahydrofuro[3,4-d][1,3]dioxole-4-carbaldehyde

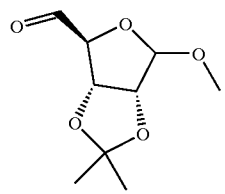

By using the literature known procedure (Barrett, A. G. M.; Lebold, S. A., *J. Org. Chem.*, 1990, 55, 3853), to a solution of dry pyridine (48.5 ml) in anhydrous methylene chloride (700 ml) was added chromium oxide (30 g, 0.3 mole) portionwise under nitrogen. During this procedure the reaction mixture was kept at room temperature by occasional cooling with an ice-water bath. To this dark red solution was added a solution of [(3aR,4R,6aR)-6-methoxy-2,2-dimethyltetrahydrofuro[3,4-d][1,3]dioxol-4-yl]methanol (5 g, 24.48 mmole, obtained from Reference Example 35) in methylene chloride (100 ml) under nitrogen. The resulting mixture was stirred at room temperature for 30 min, and poured into a cold aqueous solution of saturated sodium bicarbonate. The organic layer was separated and the aqueous layer was extracted with methylene chloride. The combined extracts were washed well with saturated sodium chloride solution until the color of the organic layer turned yellow, dried over magnesium sulfate, filtered and concentrated in vacuo. The residue was dissolved in benzene, and the solvent was removed in vacuo. This procedure was repeated several more times, to give [(3aR,4R,6aR)-6-methoxy-2,2-dimethyltetrahydrofuro[3,4-d][1,3]dioxole-4-carbaldehyde (2.8 g, 56.6%) as a yellow amorphous solid. The aldehyde was dissolved in benzene and stored in the freezer under argon.

H-NMR (δ, DMSO-d$_6$): 9.479 (1H, s), 5.088 (1H, s), 5.060 (1H, s, J=5.7 Hz), 4.533 (1H, s), 4.475 (1H, d), 3.383 (3H, s), 1.383 (3H, s), 1.254 (3H, s).

Reference Example 37

Ethyl (2R,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate and Ethyl (2S,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate

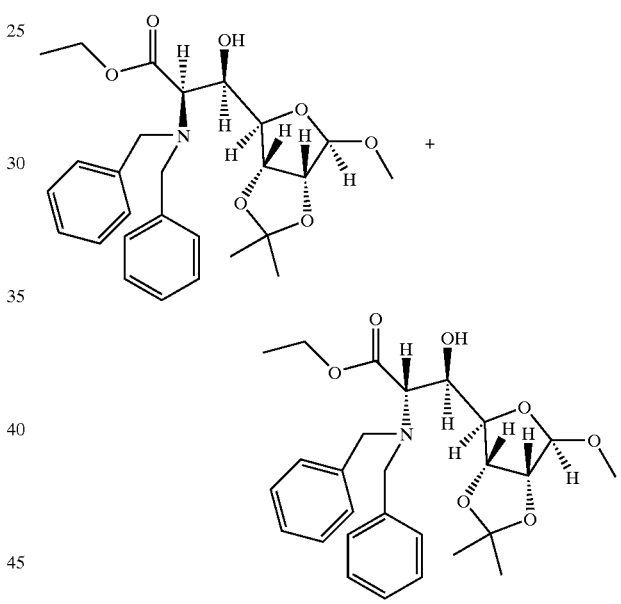

Ethyl 2-(dibenzylamino)propanoate was prepared from ethyl bromoacetate and dibenzylamine in 1,4-dioxane and absolute ethanol following the literature procedure (Scolastico, C., *Tetrahedron Letts.*, 1987, 43, 2317). A solution of ethyl 2-(dibenzylamino)propanoate (1.68 g, 5.941 mmole) in anhydrous tetrahydrofuran (30 ml) was cooled at −78° C. under argon. A solution of lithium diisopropylamide (3.0 ml, 5.941 mmole, 2.0 M solution in tetrahydrofuran/heptane/ethylbenzene, Aldrich) was introduced to this cooled solution over a period of 15 min, and the resulting reddish orange solution was stirred under this condition for 1 hour. A solution of [(3aR,4R,6aR)-6-methoxy-2,2-dimethyltetrahydrofuro[3,4-d][1,3]dioxole-4-carbaldehyde (1.2 g, 5.941 mmole, obtained from Reference Example 36) in anhydrous tetrahydrofuran (10 ml) was added via syringe to the cooled mixture over a period of 15 min. The resulting mixture was stirred at −78° C. for 3 hours under argon, and diluted with ethyl acetate. The organic layer was washed with saturated sodium bicarbonate aqueous solution and saturated sodium chloride solution, dried over sodium sulfate, filtered and concentrated in vacuo. The residue was chromatographed (flash column, silica gel, methylene chloride:diethyl ether:methanol=95:4:1) to give a 3:1 mixture of ethyl (2R,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate and ethyl (2S,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate (2.552 g, 88.5%) as a white amorphous solid. Mass (ES) m/z: 486.0 (M+H).

Reference Example 38

Ethyl (2R,3R)-3-[(3aR,4R,6R,6aR)-6-methoxy-2,2-dimethyltetrahydrofuro[3,4-d][1,3]dioxol-4-yl]-2-amino-3-hydroxypropanoate and Ethyl (2S,3R)-3-[(3aR,4R,6R,6aR)-6-methoxy-2,2-dimethyltetrahydrofuro[3,4-d][1,3]dioxol-4-yl]-2-amino-3-hydroxypropanoate

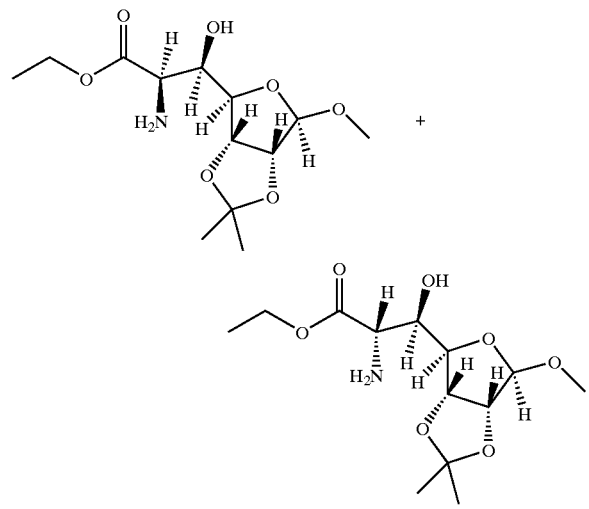

A 3:1 mixture of ethyl (2R,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate and ethyl (2S,3R)-3-[(3aR,4R,6R,6aR)-6-methoxy-2,2-dimethyltetrahydrofuro[3,4-d][1,3]dioxol-4-yl]-2-dibenzylamino-3-hydroxypropanoate (24 g, 49.43 mmole, obtained from Reference Example 37) was hydrogenated using 10% palladium on carbon in absolute methanol under atmospheric pressure at room temperature. The catalyst was removed by filtration, and the filtrate was concentrated in vacuo. The residue (15 g) was chromatographed (silica gel, methylene chloride:ethyl ether:methanol=95:4:1) to give the first diastereomer (5.08 g, 33.7%) as a colorless solid. Recrystallization from ethyl ether/n-hexane gave colorless prism, which was analyzed by the X-ray to determine the absolute stereochemistry as ethyl (2R,3R)-3-[(3aR,4R,6R,6aR)-6-methoxy-2,2-dimethyltetrahydrofuro[3,4-d][1,3]dioxol-4-yl]-2-amino-3-hydroxy propanoate.

Mass (ES) m/z: 306.4 (M+H).

H-NMR (δ, DMSO-$d_6$): 5.130 (1H, d, J=7.8 Hz), 4.914 (1H, s), 4.801 (1H, d, J=6.0 Hz), 4.557 (1H, d, J=6.0 Hz), 4.121–4.013 (3H, m), 3.792–3.672 (m, 1H), 3.531 (1H, s), 3.332 (1H, s), 3.268 (3H, s), 1.376 (3H, s), 1.254 (3H, s), 1.182 (3H, t, J=7.2 Hz).

$[\alpha]_D^{25}$=−71±2 (methylene chloride).

Further elution gave 1.0 g (6.6%) of a 1:1 mixture of two diastereomers, and 3.5 g (23.2%) of the second diastereomer as a colorless oil. The second diastereomer was assigned by NMR study as ethyl (2S,3R)-3-[(3aR,4R,6R,6aR)-6-methoxy-2,2-dimethyltetrahydrofuro[3,4-d][1,3]dioxol-4-yl]-2-amino-3-hydroxypropanoate.

Mass (ES) m/z: 306.4 (M+H).

H-NMR (δ, DMSO-$d_6$): 5.363 (1H, d, J=5.1 Hz), 4.904 (1H, s), 4.765 (1H, d, J=6.0 Hz), 4.518 (1H, d, J=6.0 Hz), 4.137–4.035 (3H, m), 3.540–3.532 (m, 1H), 3.477–3.264 (1H, m), 3.437–3.264 (1H, m), 3.242 (3H, s), 1.833 (1H, bs), 1.378 (3H, s), 1.249 (3H, s), 1.186 (3H, t, J=7.2 Hz).

Reference Example 39

Ethyl (2R,3R)-3-[(3aR,4S,6R,6aR)-6-methoxy-2,2-dimethyltetrahydrofuro[3,4-d][1,3]dioxol-4-yl]-2-{[(benzyloxy)carbonyl]amino}-3-{[(benzyloxy)carbonyl]oxy}propanoate

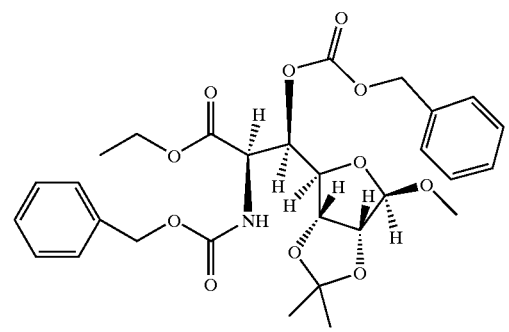

A solution of ethyl (2R,3R)-3-[(3aR,4R,6R,6aR)-6-methoxy-2,2-dimethyltetrahydrofuro[3,4-d][1,3]dioxol-4-yl]-2-amino-3-hydroxypropanoate (5 g, 16.376 mmole, obtained from Reference Example 38), dimethylaminopyridine (195 mg, 1.6 mmole) and N-(benzyloxy)carbonyloxy succinimid (8.2 g, 32.75 mmole) in anhydrous methylene chloride (100 ml) was cooled at 0° C. under argon. Triethylamine (5.1 ml, 36.3 mmole) was introduced to this solution. The resulting mixture was warmed to room temperature and stirred for 15 hours under argon. The mixture was diluted with ethyl acetate. The organic layer was washed with saturated sodium bicarbonate solution and saturated sodium chloride solution, dried over sodium sulfate, filtered and concentrated in vacuo. The residue was chromatographed (silica gel, methylene chloride:ether:methanol=97:2.5:0.5), to give ethyl (2R,3R)-3-[(3aR,4S,6R,6aR)-6-methoxy-2,2-dimethyltetrahydrofuro[3,4-d][1,3]dioxol-4-yl]-2-{[(benzyloxy)carbonyl]amino}-3-{[(benzyloxy)carbonyl]oxy}propanoate as a white solid (8.36 g, 89%).

Mass (ES) m/z: 574.4 (M+H).

IR cm$^{-1}$: 1750, 1724.

H-NMR (δ, DMSO-$d_6$): 8.025 (1H, d, J=8.88), 7.4165–7.3616 (10H, bs), 5.344–4.9061 (5H, m), 4.6827–4.5898 (4H, m), 4.1701–4.1364 (1H, m), 4.1057–4.002 (2H, m), 3.3193 (3H, s), 1.3673 (3H, s), 1.2354 (3H, s), 1.1402 (3H, t, J=7.2 Hz).

Analysis for $C_{29}H_{35}NO_{11}$: Calcd: C, 60.73; H, 6.15; N, 2.44. Found: C, 60.64; H, 5.92; N, 2.52.

$[\alpha]_D^{25}$=−33±2 (methylene chloride).

Reference Example 40

Ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-methoxytetrahydro-2-furanyl]propanoate

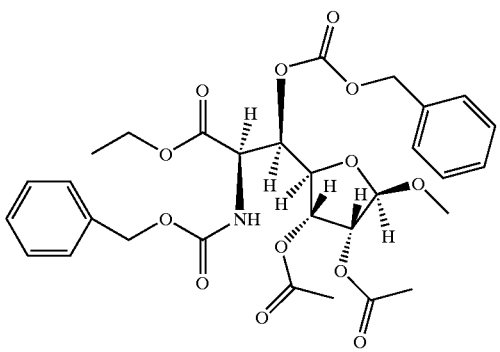

To a solution of ethyl (2R,3R)-3-[(3aR,4S,6R,6aR)-6-methoxy-2,2-dimethyltetrahydrofuro[3,4-d][1,3]dioxol-4-yl]-2-{[(benzyloxy)carbonyl]amino}-3-{[(benzyloxy)carbonyl]oxy}propanoate (800 mg, 1.395 mmole, obtained from Reference Example 39) in methanol (30 ml) was added Dowex 50WH⁺ (1 g, Aldrich). The resulting mixture was heated at 65° C. (bath temperature) for 12 hours under nitrogen. The mixture was cooled and the resin was removed by filtration. The filtrate was concentrated in vacuo to dryness, and the residue was dissolved in a mixture of acetic anhydride (10 ml) and dimethylaminopyridine (200 mg) in dry pyridine (20 ml). The resulting mixture was stirred at room temperature under nitrogen for 15 hours. The solvent was removed in vacuo, and the residue was dissolved in ethyl acetate. The organic layer was washed with saturated sodium bicarbonate solution and saturated sodium chloride solution, dried over sodium sulfate, filtered and concentrated to dryness under high vaccum, to give ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-methoxytetrahydro-2-furanyl]propanoate (800 mg, 93%) as a yellow oil.

Mass (ES) m/z: 618.3 (M+H).

IR cm$^{-1}$: 1752, 1724.

Analysis for $C_{29}H_{35}NO_{11}$: Calcd: C, 58.34; H, 5.71; N, 2.27. Found: C, 58.28; H, 5.35; N, 2.31.

$[\alpha]_D^2$=−21±2 (methylene chloride).

Reference Example 41

Ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-(2,4-dioxo-3,4-dihydro-1(2H)-pyrimidinyl)tetrahydro-2-furanyl]propanoate and Ethyl (2R,3R)-2-{[(benzyloxy)carbonyl]amino}-3-{[(benzyloxy)carbonyl]oxy}-3-[(2S,3R,4R,5S)-3,4-bis(acetyloxy)-5-(2,4-dioxo-3,4-dihydro-1(2H)-pyrimidinyl)tetrahydro-2-furanyl]propanoate

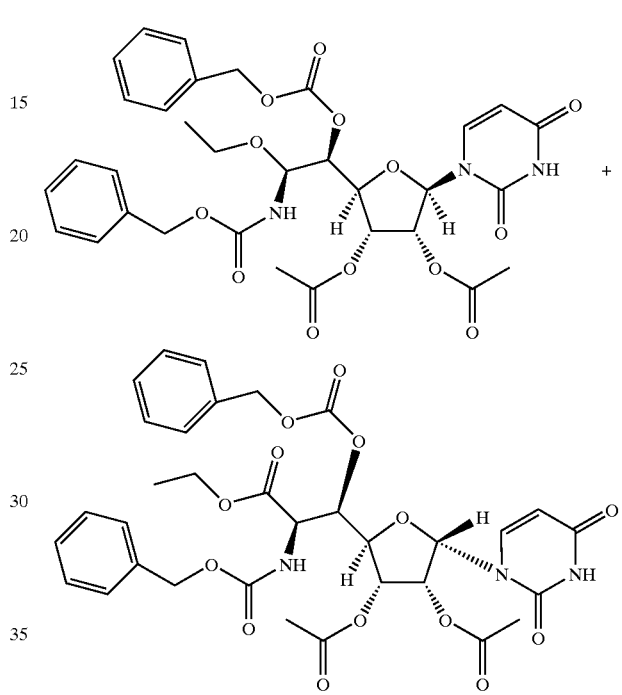

A solution of ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-methoxytetrahydro-2-furanyl]propanoate (800 mg, 1.297 mmole, obtained from Reference Example 40) in acetic anhydride (2 ml), acetic acid (8 ml) and methylene chloride (10 ml) was cooled at 0° C. (ice water bath) under nitrogen. Concentrated sulfuric acid (3 drops) was added to this cooled solution, and the resulting mixture was stirred at 0° C. for 2 hours and the cooling bath was removed. The mixture was stirred at room temperature for an additional 2 hours under nitrogen, and diluted with ethyl acetate. The organic layer was washed with saturated sodium bicarbonate solution and saturated sodium chloride solution, dried over sodium sulfate, filtered and concentrated to dryness to give ethyl (2R,3R)-2-{[(benzyloxy)carbonyl]amino}-3-{[(benzyloxy)carbonyl]oxy}-3-[(2S,3R,4R,5R)-3,4,5-tri(acetyloxy)-methoxytetrahydro-2-furanyl]propanoate as a yellow amorphous solid (800 mg, 100%). The crude material was used for the next step without further purification.

A solution of ethyl (2R,3R)-2-{[(benzyloxy)carbonyl]amino}-3-{[(benzyloxy)carbonyl]oxy}-3-[(2S,3R,4R,5R)-3,4,5-tri(acetyloxy)-methoxytetrahydro-2-furanyl]propanoate (800 mg, 1.24 mmole) and bis-O-(trimethylsilyl) uracil (952 mg, 3.72 mmole, prepared from uracil and trimethylsilyl chloride in hexamethyldisilazan according to the literature procedure; Barrett, A. G. .; Lebold, S. A., *J. Org. Chem.*, 1990, 55, 3853) in anhydrous methylene chloride (10 ml) was cooled at 0° C. (ice-water bath) under argon. To this solution was added trimethylsilyl trifluoromethanesulfonate (0.298 ml, 1.488 mmole) dropwise via syringe. The resulting mixture was stirred at 0° C. for 30 min, then at room temperature for 15 hours, and the mixture was diluted with ethyl acetate. The organic layer was washed with saturated sodium bicarbonate solution and saturated sodium chloride solution, dried over sodium sulfate, filtered and concentrated in vacuo. The residue was chromatographed (silica gel, methylene chloride:ether:methanol= 50:3:2), to give a mixture of the D-uracil isomer, ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-(2,4-dioxo-3,4-dihydro-1(2H)-pyrimidinyl)tetrahydro-2-furanyl]propanoate, and the D-uracil isomer, ethyl (2R,3R)-2-{[(benzyloxy)carbonyl]amino}-3-{[(benzyloxy)carbonyl]oxy}-3-[(2S,3R,4R,5S)-3,4-bis(acetyloxy)-5-(2,4-dioxo-3,4-dihydro-1(2H)-pyrimidinyl)tetrahydro-2-furanyl]propanoate in an approximate ratio of 3:1 (550 mg, 60.7%). This mixture was used for the next step.

The pure □-uracil isomer, ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-(2,4-dioxo-3,4-dihydro-1(2H)-pyrimidinyl)tetrahydro-2-furanyl]propanoate was isolated as a white amorphous solid by further chromatography (silica gel, methylene chloride:ether:methanol=50:3:2).

Mass (ES) m/z: 698.1 (M+H).

IR cm$^{-1}$: 1753, 1722.

H-NMR (δ, DMSO-d$_6$): 11.500 (1H, bs), 8.054 (1H, d, J=9.0 Hz), 7.779 (1H, d, J=9.0 Hz), 7.400–7.370 (10H, bs), 5.843–5.518 (5H, m), 5.182–5.023 (4H, m), 4.549–4.510 (1H, m), 4.203–4.161 (1H, m), 4.068–4.006 (3H, m), 2.058 (3H, s), 2.013 (3H, s), 1.115 (3H, t, J=7.2 Hz).

Analysis for $C_{33}H_{35}N_3O_{14}$: Calcd: C, 56.81; H, 5.06; N, 6.02. Found: C, 56.18; H, 5.25; N, 5.90.

Reference Example 42

Ethyl (2R,3R)-3-[(3aR,4R,6R,6aR)-6-methoxy-2,2-dimethyltetrahydrofuro[3,4-d][1,3]dioxol-4-yl]-2-{[(benzyloxy)carbonyl]amino}-3-hydroxypropanoate

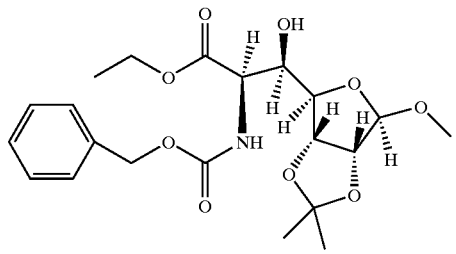

A solution of ethyl (2R,3R)-3-[(3aR,4R,6R,6aR)-6-methoxy-2,2-dimethyltetrahydrofuro[3,4-d][1,3]dioxol-4-yl]-2-amino-3-hydroxypropanoate (3.05 g, 9.99 mmole, obtained from Reference Example 38), dimethylaminopyridine (250 mg, 2.1 mmole) and N-(benzyloxy)carbonyloxy succinimid (2.49 g, 10 mmole) in anhydrous methylene chloride (40 ml) was cooled at 0° C. under argon. Triethylamine (1.394 ml, 10 mmole) was introduced to this solution. The resulting mixture was warmed to room temperature and stirred at room temperature for 15 hours under argon, and the mixture was diluted with ethyl acetate. The organic layer was washed with saturated sodium bicarbonate solution and saturated sodium chloride solution, dried over sodium sulfate, filtered and concentrated in vacuo. The residue was chromatographed (silica gel, methylene chloride:ether:methanol=93:5:2), to give ethyl (2R,3R)-3-[(3aR,4R,6R,6aR)-6-methoxy-2,2-dimethyltetrahydrofuro[3,4-d][1,3]dioxol-4-yl]-2-{[(benzyloxy)carbonyl]amino}-3-hydroxypropanoate as a white solid (2.92 g, 66%).

Mass (ES) m/z: 440.4 (M+H).

IR cm$^{-1}$: 3435, 3379, 1724, 1706.

H-NMR (δ, DMSO-d$_6$): 7.387–7.333 (5H, m), 7.0875 (1H, d, J=9.3 Hz), 5.4135 (1H, d, J=7.5 Hz), 5.129–5.024 (2H, m), 4.941 (1H, s), 4.814 (1H, d, J=6.0 Hz), 4.595 (1H, d, J=6.0 Hz), 4.435 (1H, d, J=9.3 Hz), 4.100 (2H, q), 3.900–3.896 (2H, bs), 3.344 (3H, s), 1.370 (3H, s), 1.255 (3H, s), 1.183 (3H, t, J=7.2 Hz).

Analysis for $C_{21}H_{29}N_1O_9$: Calcd: C, 57.40; H, 6.65; N, 3.19. Found: C, 57.00; H, 6.80; N, 3.09.

$[α]_D^{25}$=–22±1 (methylene chloride).

Reference Example 43

Ethyl (2R,3R)-3-[(3aR,4S,6R,6aR)-6-methoxy-2,2-dimethyltetrahydrofuro[3,4-d][1,3]dioxol-4-yl]-3-(acetyloxy)-2-{[(benzyloxy)carbonyl]amino}propanoate

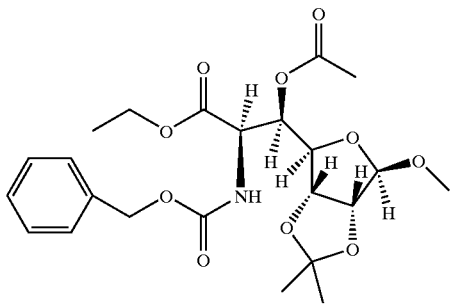

A solution of ethyl (2R,3R)-3-[(3aR,4R,6R,6aR)-6-methoxy-2,2-dimethyltetrahydrofuro[3,4-d][1,3]dioxol-4-yl]-2-{[(benzyloxy)carbonyl]amino}-3-hydroxypropanoate (3.1 g, 7.054 mmole, obtained from Reference Example 42) in acetic anhydride (25 ml) and dry pyridine (50 ml) in the presence of dimethylaminopyridine (500 mg) was stirred at room temperature under nitrogen for 15 hours. The solvent was removed in vacuo, and the residue was dissolved in ethyl acetate. The organic layer was washed with saturated sodium bicarbonate solution and saturated sodium chloride solution, dried over sodium sulfate, filtered and concentrated in vacuo. The residue was chromatographed (silica gel, methylene chloride:ether:methanol=97:2:1) to give ethyl (2R,3R)-3-[(3aR,4S,6R,6aR)-6-methoxy-2,2-dimethyltetrahydrofuro[3,4-d][1,3]dioxol-4-yl]-3-(acetyloxy)-2-{[(benzyloxy)carbonyl]amino}propanoate (3.4 g, 100%) as a white amorphous solid.

Mass (ES) m/z: 482.2 (M+H).

IR cm$^{-1}$: 1750, 1722.

Analysis for $C_{23}H_{31}N_1O_{10}$: Calcd: C, 57.37; H, 6.49; N, 2.91. Found: C, 57.19; H, 6.74; N, 2.84.

$[α]_D^{25}$=–47±1 (methylene chloride).

Reference Example 44

Ethyl (2R,3R)-3-(acetyloxy)-2-{[(benzyloxy)carbonyl]amino}-3-[(2R,3R,4R,5R)-3,4-bis(acetyloxy)-5-methoxytetrahydro-2-furanyl]propanoate

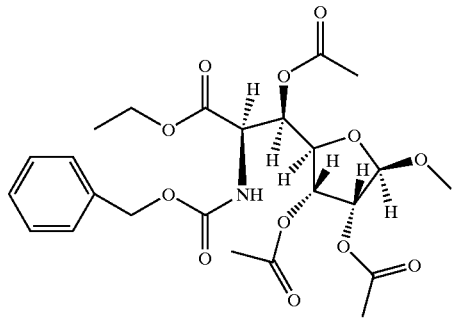

Ethyl (2R,3R)-3-[(3aR,4S,6R,6aR)-6-methoxy-2,2-dimethyltetrahydrofuro[3,4-d][1,3]dioxol-4-yl]-3-(acetyloxy)-2-{[(benzyloxy)carbonyl]amino}propanoate (4 g, 8.307 mmole, obtained from Reference Example 43) was dissolved in methanol (80 ml), and Dowex 50WH+ (4 g, Aldrich) was added to this solution. The resulting mixture was heated at 65° C. (bath temperature) for 12 hours under nitrogen. The resulting mixture was cooled and the resine was removed by filtration. The filtrate was concentrated in vacuo to dryness, and the residue was dissolved in a mixture of acetic anhydride (20 ml), dimethylaminopyridine (500 mg) and dry pyridine (40 ml). The resulting mixture was stirred at room temperature under nitrogen for 15 hours. The solvent was removed in vacuo, and the residue was dissolved in ethyl acetate. The organic layer was washed with saturated sodium bicarbonate solution and saturated sodium chloride solution, dried over sodium sulfate, filtered and concentrated to dryness under high vaccum, to give ethyl (2R,3R)-3-(acetyloxy)-2-{[(benzyloxy)carbonyl]amino}-3-[(2R,3R,4R,5R)-3,4-bis(acetyloxy)-5-methoxytetrahydro-2-furanyl]propanoate (4.098 mg, 93.8%) as a yellow oil.

Mass (ES) m/z: 526.1 (M+H).

IR cm$^{-1}$: 1750, 1722.

H-NMR (δ, DMSO-d$_6$): 7.880 (1H, d, J=4.5 Hz), 7.400–7.360 (5H, m), 5.255–5.219 (2H, m), 5.178–5.014 (4H, m), 4.638–4.590 (1H, m), 4.122–4.052 (3H, m), 3.354 (3H, s), 2.077 (3H, s), 1.989 (3H, s), 1.953 (3H, s), 1.174 (3H t, J=7.2 Hz).

Analysis for $C_{24}H_{31}N_1O_{12}$: Calcd: C, 54.85; H, 5.95; N, 2.67. Found: C, 55.08; H, 5.58; N, 2.70.

$[\alpha]_D^{25}$=−37±2 (methylene chloride).

Reference Example 45

Ethyl (2R,3R)-3-(acetyloxy)-2-{[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate and Ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate

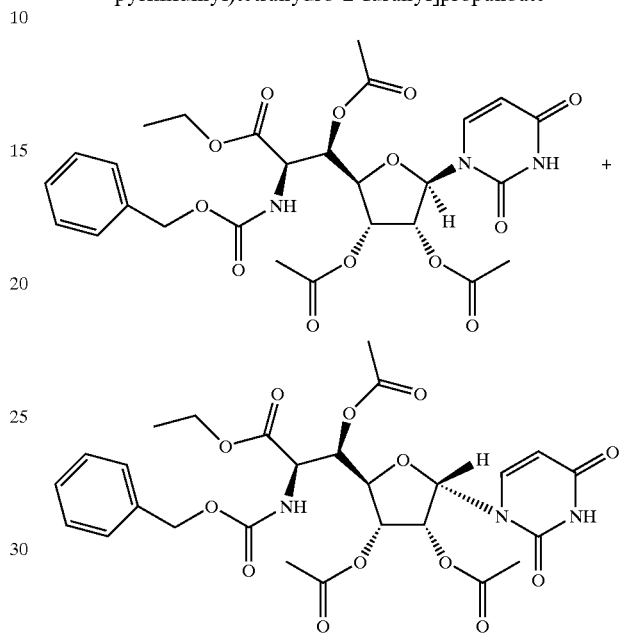

Ethyl (2R,3R)-3-(acetyloxy)-2-{[(benzyloxy)carbonyl]amino}-3-[(2R,3R,4R,5R)-3,4-bis(acetyloxy)-5-methoxytetrahydro-2-furanyl]propanoate (obtained from Reference Example 44) was converted to ethyl (2R,3R)-3-(acetyloxy)-2-{[(benzyloxy)carbonyl]amino}-3-[(2R,3R,4R,5R)-3,4,5-tri(acetyloxy)-tetrahydro-2-furanyl]propanoate by using the procedure described in Reference Example 41.

To a cooled solution of ethyl (2R,3R)-3-(acetyloxy)-2-{[(benzyloxy)carbonyl]amino}-3-[(2R,3R,4R,5R)-3,4,5-tri(acetyloxy)-tetrahydro-2-furanyl]propanoate (594 mg, 1.073 mmole) and bis-O-(trimethylsilyl)uracil (550 mg, 2.146) in anhydrous methylene chloride (10 ml) was added trimethylsilyl trifluoromethanesulfonate (0.258 ml, 1.288 mmole) dropwise via syringe. The resulting mixture was stirred at 0° C. for 30 min, then at room temperature for 15 hours, and the mixture was diluted with ethyl acetate. The organic layer was washed with saturated sodium bicarbonate solution and saturated sodium chloride solution, dried over sodium sulfate, filtered and concentrated in vacuo. The residue was chromatographed (silica gel, methylene chloride:ether:methanol=50:3:2), to give a mixture of the □-uracil isomer, ethyl (2R,3R)-3-(acetyloxy)-2-{[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate and the □-uracil isomer, ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate in an approximate ratio of 2:1 (550 mg, 60.7%). This mixture of two isomers was used for the next step.

The pure □-uracil isomer, ethyl (2R,3R)-3-(acetyloxy)-2-{[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate, was isolated as a white amorphous solid by Further chromatography (silica gel, methylene chloride:ether:methanol=50:3:2).

Mass (ES) m/z: 606.1 (M+H).

IR cm$^{-1}$: 1752, 1716.

Analysis for $C_{27}H_{31}N_3O_{13}$: Calcd: C, 53.55; H, 5.16; N, 6.94. Found: C, 53.66; H, 5.04; N, 6.33.

$[\alpha]_D^{25}$=−18±8 (methylene chloride).

Reference Example 46

The hydrogen chloride salt mixture of

Ethyl (2R,3R)-3-(acetyloxy)-2-[[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate and Ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate

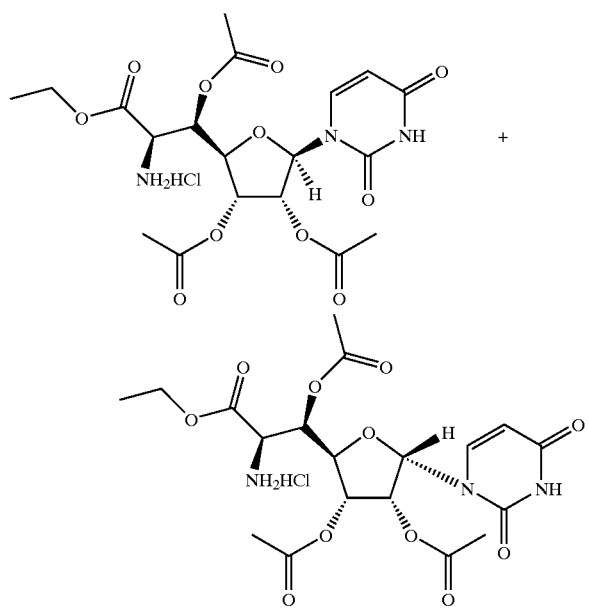

A 2:1 mixture of ethyl (2R,3R)-3-(acetyloxy)-2-{[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate and ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate (413.8 mg, 0.6833 mmole, obtained from Reference Example 45) was hydrogenated using 10% palladium on carbon (110 mg) in absolute methanol (25 ml) containing 1.1 mole equivalent of hydrogen chloride at atmospheric pressure at room temperature. The catalyst was removed by filtration, and the filtrate was concentrated in vacuo to give the hydrogen chloride salt of a mixture of ethyl (2R,3R)-3-(acetyloxy)-2-{[(benzyloxy)carbonyl]amino}-3-[(2R,3R,4R,5R)-3,4-bis(acetyloxy)-5-(2,4-dioxo-3,4-dihydro-1(2H)-pyrimidinyl)tetrahydro-2-furanyl]propanoate and ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate as a white solid. The residual solid was used for the next step without further purification.

Reference Example Example 47

(1S,2S)-2-{[(Benzyloxy)carbonyl]amino}-3-[(3,3-diethoxypropyl)amino]-1-methyl-3-oxopropyl myristate

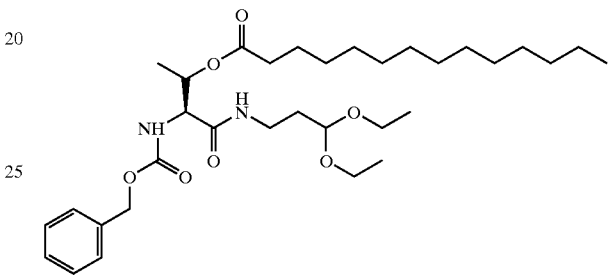

To a solution of [(1S,2S)-1-(3,3-diethoxypropylcarbamoyl)-2-hydroxy-propyl]carbamic acid benzyl ester (300 mg, 0.785 mmol, obtained from Reference Example 17) in methylene chloride (5 ml) was added myristic acid (163 mg, 0.714 mmol), dicyclohexylcarbodiimide (162 mg, 0.785 mmol) and dimethylaminopyridine (9 mg, 0.074 mmol). The resulting mixture was stirred under nitrogen at room temperature for 18 hours. The mixture was filtered, the filtrate was washed with 2% hydrochloric acid, aqueous sodium bicarbonate and saturated sodium chloride solutions, dried over magnesium sulfate, filtered and concentrated in vacuo. The residue was chromatographed (flash column, silica gel, 30% ethyl acetate in hexane) to provide (1S,2S)-2-{[(benzyloxy)carbonyl]amino}-3-[(3,3-diethoxypropyl)amino]-1-methyl-3-oxopropyl myristate (352 mg, 83%) as a white solid.

MS (ES): m/z 615.4 (M+Na).

IR cm$^{-1}$: 3290, 2921, 2851, 1732, 1691, 1649, 1541.

Reference Example Example 48

(1S,2S)-2-{[(Benzyloxy)carbonyl]amino}-1-methyl-3-oxo-3-[(3-oxopropyl)amino]propyl myristate

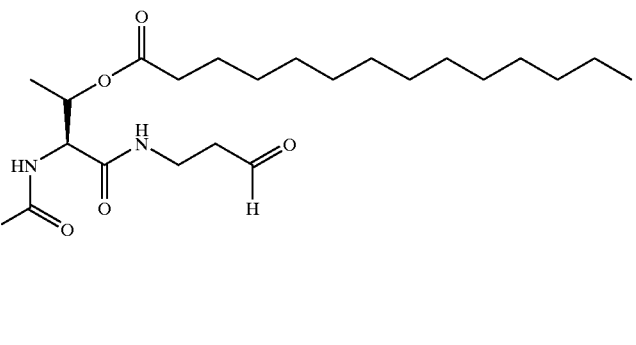

To a solution of (1S,2S)-2-{[(benzyloxy)carbonyl]amino}-3-[-(3,3-diethoxypropyl)amino]-1-methyl-3-oxopropyl myristate (1.06 g, 1.79 mmol, obtained from Reference Example 47) in anhydrous tetrahydrofuran was added 0.5 N hydrochloric acid (4.3 ml). The resulting solution was stirred at room temperature for 5 hours. The reaction mixture was brought to pH 9 with aqueous sodium bicarbonate, extracted with ethyl acetate (3×75 ml), the combined organics were washed with saturated sodium chloride, dried over magnesium sulfate, filtered and concentrated in vacuo. The residue was chromatographed (flash column, silica gel, 45% ethyl acetate in hexane) to provide (1S,2S)-2-{[(benzyloxy)carbonyl]amino}-1-methyl-3-oxo-3-[(3-oxopropyl)amino]propyl myristate (694 mg, 75%) as a white solid.

MS (ES): m/z 519.3 (M+H).

IR cm$^{-1}$: 3294, 2920, 2848, 1733, 1642.

Preparation of Truncated AA896 Analogs

Example 1 tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate chloride) to provide tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate (258 mg, 60%) as a white amorphous solid.

MS (ES): m/z 1042.2 (M+H).

IR cm$^{-1}$: 3387, 1715, 1668.

$^1$H NMR (δ, DMSO-d$_6$): 7.792–7.763 (m, 2H), 7.381–7.144 (m, 7H), 6.827 (d, J=8.73 Hz, 2H), 5.929 (d, J=7.68 Hz, 1H), 5.875 (d, 7.83 Hz, 1H), 5.623 (d, J=6.24 Hz, 1H), 5.011 (s, 2H), 4.885 (d, J=4.35 Hz, 2H), 4.743–4.701 (m, 1H), 4.331–4.291 (m, 1H), 4.215–4.183 (m, 1H), 4.086 (d, J=5.28 Hz, 1H), 3.948–3.889 (m, 2H), 3.703 (s, 3H), 3.452–3.408 (m, 2H), 3.079–3.060 (m, 4H), 1.719–1.707 (m, 2H), 1.503 (m, 2H), 1.416 (s, 9H), 0.886 (s, 9H), 0.876 (s, 3H), 0.850 (s, 3H), 0.777 (m, 3H), 0.709 (s, 9H), 0.100 (s, 3H), 0.050 (s, 3H), −0.100 (s, 3H), −0.200 (s, 3H).

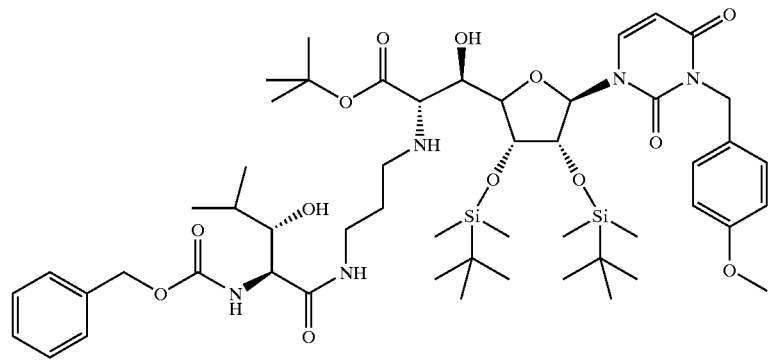

A solution of [2-hydroxy-3-methyl-1-(3-oxo-propylcarbamoyl)-butyl]-carbamic acid benzyl ester (175 mg, 0.519 mmol, obtained from Reference Example 14) and tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (300 mg, 0.416 mmol, obtained from Reference Example 6) in anhydrous tetrahydrofuran was stirred at room temperature under a nitrogen atmosphere for 15 minutes. Acetic acid (3 drops) and sodium triacetoxyborohydride (176 mg, 0.831 mmol) were added and the resulting solution was stirred under nitrogen for an additional 2.5 hours. The reaction mixture was basified to pH 9 with aqueous sodium carbonate solution, and the aqueous layer was extracted with ethyl acetate (3×75 mL). The combined extracts were washed with saturated sodium chloride solution, dried over sodium sulfate, filtered and concentrated in vacuo. The residue was chromatographed (flash column, silica gel, 2.5% methanol in methylene

Example 2 tert-Butyl (2S,3R)-2-[(3-{[(2S,3S)-2-amino-3-hydroxy-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

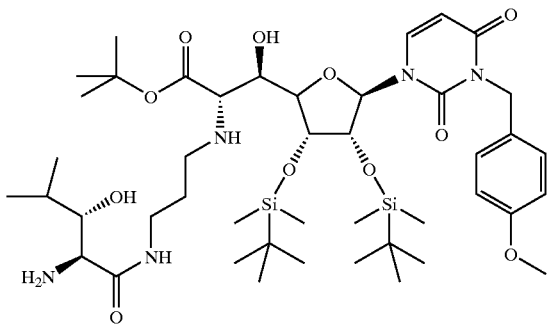

tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate (208 mg, 0.2 mmol, obtained from Example 1) was hydrogenated in methanol (2 ml) using 10% palladium on carbon (42 mg) under atmospheric pressure to provide tert-butyl (2S,3R)-2-[(3-{[(2S,3S)-2-amino-3-hydroxy-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (167 mg, 92%) as a white amorphous solid.

MS (ES): m/z 908.2 (M+H), 454.9 (M+2H)$^{2+}$.

IR cm$^{-1}$: 3389, 1670.

Analytical HPLC (4.6×150 mm Phenomenex ODS3 column eluted with a linear gradient of 10–90% acetonitrile in water containing 0.02% trifluoroacetic acid over 15 minutes): 100% at 12.94 minutes.

$^1$H NMR (δ, DMSO-d$_6$): 7.854–7.817 (m, 1H), 7.781 (d, J=8.16 Hz, 1H), 7.234 (d, J=8.7 Hz, 2H), 6.830 (d, J=8.7 Hz, 2H), 5.926 (d, J=7.65 Hz, 1H), 5.875 (d, J=8.07 Hz, 1H), 5.639 (d, J=6.24 Hz, 1H), 4.944–4.837 (m, 2H), 4.608–4.590 (m, 1H), 4.335–4.295 (m, 1H), 4.219–4.184 (m, 1H), 4.099–4.082 (m, 1H), 3.750–3.730 (m, 1H), 3.705 (s, 3H), 3.254–3.199 (m, 2H), 3.099–3.038 (m, 4H), 2.353 (m, 1H), 2.080 (m, 1H), 1.877–1.794 (m, 1H), 1.728 (m, 2H), 1.533–1.489 (m, 2H), 1.420 (s, 9H), 0.888 (s, 9H), 0.857–0.757 (overlapping 2d, 6H), 0.712 (s, 9H), 0.100 (s, 3H), 0.050 (s, 3H), −0.075 (s, 3H), −0.200 (s, 3H).

Example 3 tert-Butyl (5R,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate

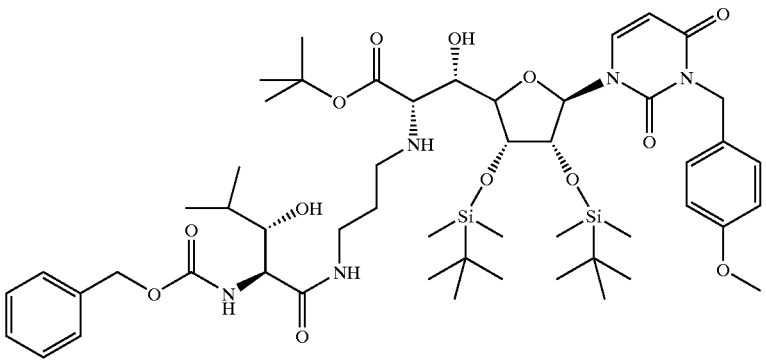

By using an analogous procedure to that described for Example 1, a solution of [2-hydroxy-3-methyl-1-(3-oxo-propylcarbamoyl)-butyl]-carbamic acid benzyl ester (175 mg, 0.519 mmol, obtained from Reference Example 14), tert-butyl (2S,3S)-2-amino-dioxo-3,4-dihydro-1(2H)-pyrimidinyl)-tetrahydro-2-furanyl]-3-hydroxypropanoate (300 mg, 0.416 mmol, obtained from Reference Example 5), acetic acid (5 drops) and sodium triacetoxyborohydride (176 mg, 0.831 mmol) in anhydrous tetrahydrofuran (5 ml) was stirred at room temperature under a nitrogen atmosphere for 2 hours. The product was purified by preparative HPLC (21.2×250 mm Prodigy ODS, 3.5 micron column eluted with 60–100% acetonitrile in water containing 0.02% trifluoroacetic acid over 45 minutes) to provide tert-butyl (5R,12S)-12-[(S)-[(3R,4R,5R)-3,4-bis{[tert-butyl(dimethyl)silyl]oxy}-5-(3-(4-methoxybenzyl)-2,4-dioxo-3, 4-dihydro-1(2H)-pyrimidinyl)tetrahydro-2-furanyl](hydroxy)methyl]-5-[(1S)-1-hydroxy-2-methyl-propyl]-3,6-dioxo-1-phenyl-2-oxa-4,7,11-triazatridecan-13-oate (7 mg, 2%) as a pale yellow solid.

MS (ES): m/z 1042.4 (M+H).

$^1$H NMR (δ, CDCl$_3$): 8.003 (d, J=8.13 Hz, 1H), 7.444 (d, J=8.67 Hz, 2H), 7.378–7.335 (bs, 5H), 7.013 (bs, 1H), 6.805 (d, J=8.67 Hz, 2H), 5.943–5.930 (m, 2H), 5.751 (d, J=8.13 Hz, 1H), 5.092 (bs, 2H), 5.030 (bs, 2H), 4.168–4.131 (m, 1H), 4.117–4.087 (m, 2H), 4.005–3.992 (m, 1H), 3.548–3.490 (m, 1H), 3.396–3.226 (m, 4H), 2.718–2.657 (m, 1H), 2.561–2.522 (m, 1H), 1.857–1.788 (m, 2H), 1.722–1.591 (m, 4H), 1.464 (s, 9H), 1.009 (d, J=6.54 Hz, 3H), 0.940 (d, J=6.75 Hz, 3H), 0.879 (s, 9H), 0.838 (s, 9H), 0.050 (s, 6H), –0.050 (s, 6H).

Example 4 tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (hydroxy)methyl]-5-isobutyl-3,6-dioxo-1-phenyl-2-oxa-4,7,11-triazatridecan-13-oate (276 mg, 97%), as a white amorphous solid.

MS (ES): m/z 1026.2 (M+H).

IR cm$^{-1}$: 3337, 2956, 1715, 1669.

$^1$H NMR (δ, DMSO-d$_6$): 7851–7.776 (m, 2H), 7.386–7.296 (m, 5H), 7.232 (d, J=8.7 Hz, 2H), 6.827 (d, J=8.7 Hz, 2H), 5.912–5.837 (m, 2H), 5.64 (d, J=6.36 Hz, 1H), 5.053–4.962 (m, 2H), 4.892–4.879 (m, 1H), 4.325–4.285 (m, 1H), 4.211–4.181 (m, 1H), 4.112–4.096 (m, 1H), 3.977–3.926 (m, 2H), 3.703 (bs, 4H), 3.127–3.082 (m, 2H), 3.052–2.987 (m, 2H), 2.332–2.157 (m, 2H), 1.693–1.533 (m, 2H), 1.488–1.447 (m, 2H), 1.420 (s, 9H), 1.355–1.320 (m, 2H), 0.884 (s, 9H), 0.865–0.777 (overlapping 2d, 6H), 0.708 (s, 9H), 0.075 (s, 3H), 0.050 (s, 3H), –0.100 (s, 3H), –0.250 (s, 3H).

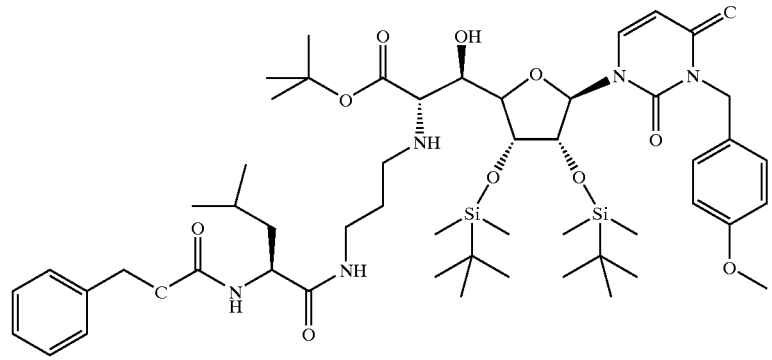

A solution of tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxy-propanoate (200 mg, 0.277 mmol, obtained from Reference Example 6) and [(1S)-3-methyl-1-(3-oxo-propylcarbamoyl)-butyl]-carbamic acid benzyl ester (111 mg, 0.35 mmol, obtained from Reference Example 16) in anhydrous tetrahydrofuran (4 ml) was stirred at room temperature under a nitrogen atmosphere for 15 minutes. Acetic acid (4 drops) and sodium triacetoxyborohydride (117 mg, 0.55 mmol) were added, and the resulting solution was stirred under nitrogen for an additional 3.5 hours. The reaction mixture was basified to pH 9 with sodium carbonate aqueous solution, and the aqueous layer was extracted with ethyl acetate (3×80 ml). The combined extracts were washed with saturated sodium chloride, dried over sodium sulfate, filtered and concentrated in vacuo. The residue was chromatographed (flash column, silica gel, 2.5% methanol in methylene chloride) to provide tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]

Example 5 tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

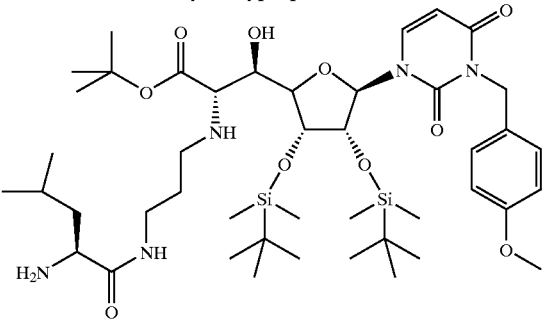

tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (234 mg, 0.228 mmol, obtained from Example 4) was hydrogenated in methanol (3 ml)

using 10% palladium on carbon (58 mg) under atmospheric pressure to provide tert-butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (187 mg, 92%) as a white amorphous solid.

MS (ES): m/z 892.2 (M+H).

IR cm$^{-1}$: 1716, 1671.

Analytical HPLC (4.6×150 mm Phenomenex ODS3 column eluted with a linear gradient of 10–90% acetonitrile in water containing 0.02% trifluoroacetic acid over 15 minutes): 100% at 13.24 minutes.

$^1$H NMR (δ, DMSO-d$_6$): 7.82–7.77 (m, 2H), 7.23 (d, J=8.64 Hz, 2H), 6.83 (d, J=8.67 Hz, 2H), 5.94–5.85 (m, 2H), 5.65 (d, J=6.3 Hz, 1H), 4.94–4.84 (m, 2H), 4.33–4.29 (m, 1H), 4.22–4.18 (m, 1H), 4.10 (d, J=4.98 Hz, 1H), 3.71 (bs, 4H), 3.15–3.11 (m, 2H), 3.09–3.05 (m, 4H), 2.34–2.15 (m, 2H), 1.71–1.64 (m, 2H), 1.52–1.32 (m, 2H), 1.42 (s, 9H), 1.25–1.09 (s, 2H), 0.89 (s, 9H), 0.87–0.78 (overlapping 2d, 6H), 0.71 (s, 9H), 0.094 (s, 3H), 0.074 (s, 3H), −0.06 (s, 3H), −0.24 (s, 3H).

Example 6 tert-Butyl (5S,12S)-12-[(R)-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate

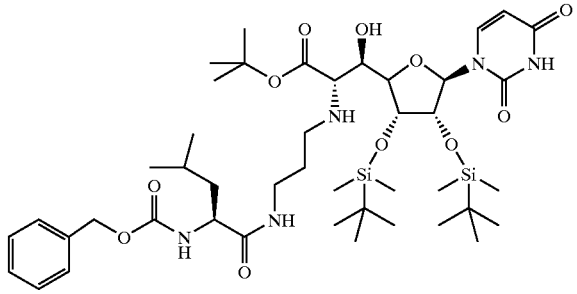

To a solution of tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (420 mg, 0.409 mmol, obtained from Example 4) in acetonitrile (20 ml) was added a solution of ammonium cerium(IV) nitrate (898 mg, 1.6 mmol) in water (4 ml). The resulting solution was stirred for 48 hours at room temperature, and saturated sodium chloride aqueous solution was added. The aqueous layer was extracted with ethyl acetate (3×75 mL). The combined extracts were washed with saturated sodium chloride, dried over sodium sulfate, filtered and concentrated in vacuo. The resultant residue was chromatographed (flash column, silica gel, 5% methanol in methylene chloride) to provide tert-butyl (5S,12S)-12-[(R)-[(3R,4R,5R)-3,4-bis{[tert-butyl(dimethyl)silyl]oxy}-5-(2,4-dioxo -3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (91 mg, 25%) as a pale tan amorphous solid.

MS (ES): m/z 906.4 (M+H).

Example 7 tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl]-3-hydroxypropanoate

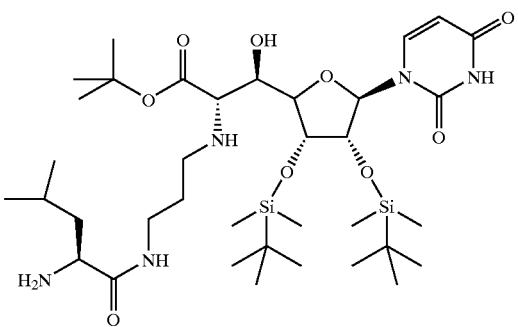

tert-Butyl (5S,12S)-12-[(R)-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (9 mg, 0.0099 mmol, obtained from Example 6) was hydrogenated in methanol (2 ml) using 10% palladium on carbon (7 mg) under atmospheric pressure to provide tert-butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl]-3-hydroxypropanoate (5 mg, 65%) as a pale tan amorphous solid.

MS (ES): m/z 772.4 (M+H).

Example 8 tert-Butyl (5S,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate

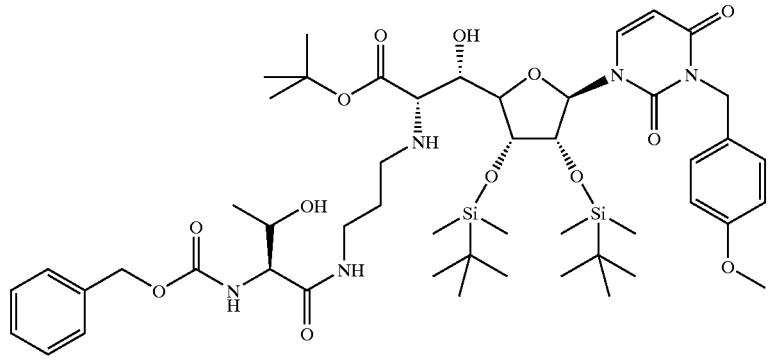

By using an analogous procedure to that described in Example 1, a solution of [(1S,2S)-2-hydroxy-1-(3-oxopropylcarbamoyl)-propyl]-carbamic acid benzyl ester (99 mg, 0.32 mmol, obtained from Reference Example 18), tert-butyl (2S,3S)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (165 mg, 0.229 mmol, obtained from Reference example 5), acetic acid (4 drops) and sodium triacetoxyborohydride (97 mg, 0.457 mmol) in anhydrous tetrahydrofuran (4 ml) was stirred at room temperature under nitrogen for 4 hours. The residue was chromatographed (flash column, silica gel, 5% methanol in methylene chloride) to provide tert-butyl (5S,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate (77 mg, 33%) as a white amorphous solid.

MS (ES): m/z 1014.5 (M+H).

$^1$H NMR (δ, CDCl$_3$): 8.002 (d, J=8.1 Hz, 1H), 7.441 (d, J=8.64 Hz, 2H), 7.359–7.278 (m, 5H), 7.056 (m, 1H), 6.805 (d, J=8.64 Hz, 2H), 6.022 (d, J=5.31 Hz, 1H), 5.786–5.759 (m, 3H), 5.200–4.950 (m, 4H), 4.454–4.435 (m, 1H), 4.242–4.210 (m, 1H), 4.144–4.129 (m, 2H), 4.077–4.067 (m, 1H), 3.728 (s, 3H), 3.403–3.148 (m, 2H), 3.003 (m, 2H), 1.888 (m, 2H), 1.722–1.591 (m, 4H), 1.489 (s, 9H), 1.185 (d, J=6.39 Hz, 3H), 0.880 (s, 9H), 0.813 (s, 9H), 0.030 (s, 3H), 0.027 (s, 3H), 0.025 (s, 3H), −0.100 (s, 3H).

Example 9 tert-Butyl (2S,3S)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

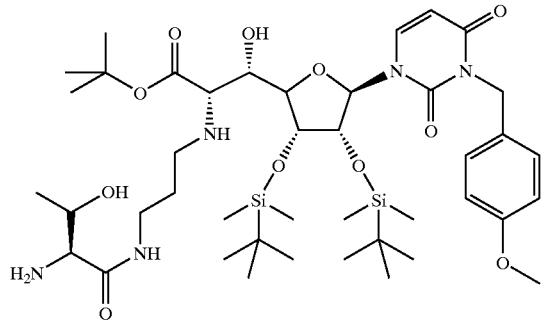

By using an analogous procedure to that described in Example 2, tert-butyl (5S,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate (77 mg, 0.076 mmol, obtained from Example 8) was hydrogenated in methanol (2 ml) using 10% palladium on carbon (15 mg). The product was purified by chromatography (flash column, silica gel, 10 methanol in methylene chloride) to provide tert-butyl (2S,3S)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (20 mg, 30%) as a pale yellow solid.

MS (ES): m/z 880.5 (M+H).

$^1$H NMR (δ, CDCl$_3$): 8.032 (d, J=8.07 Hz, 1H), 7.894–7.829 (m, 1H), 7.451 (d, J=8.55 Hz, 2H), 7.345 (d, J=8.61 Hz, 1H), 6.810 (d, J=8.67 Hz, 2H), 5.999 (d, J=4.65 Hz, 1H), 5.945–5.862 (m, 1H), 5.789–5.730 (m, 1H), 5.040 (bs, 2H), 4.362–4.330 (m, 1H), 4.237–4.129 (m, 2H), 4.000–3.989 (m, 1H), 3.522–3.489 (m, 1H), 3.451–3.354 (m, 2H), 3.267–3.149 (m, 2H), 2.815–2.754 (m, 1H), 2.666–2.646 (m, 1H), 2.530–2.470 (m, 1H), 1.715–1.674 (m, 4H), 1.465 (s, 9H), 1.197 (d, J=6.42 Hz, 3H), 0.884 (s, 9H), 0.834 (s, 9H), 0.100 (s, 3H), 0.050 (s, 3H), −0.050 (s, 6H).

Example 10 tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate

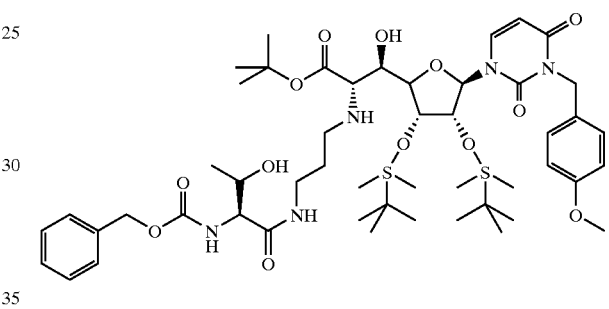

By using an analogous procedure to that described for Example 1, a solution of [(1S,2S)-2-hydroxy-1-(3-oxopropylcarbamoyl)-propyl]-carbamic acid benzyl ester (108 mg, 0.35 mmol, obtained from Reference Example 18), tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (230 mg, 0.319 mmol, obtained from Reference Example 6), acetic acid (3 drops), and sodium triacetoxyborohydride (135 mg, 0.64 mmol) in anhydrous tetrahydrofuran (5 ml) was stirred under nitrogen at room temperature for 4 hours. The residue was chromatographed (flash column, silica gel, 5% methanol in methylene chloride) to provide tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate (174 mg, 54%) as a pale yellow solid.

MS (ES): m/z 1014.1 (M+H).

IR cm$^{-1}$: 3398, 1715, 1670.

$^1$H NMR (δ, CDCl$_3$): 7.441–7.313 (m, 8H), 6.816–6.787 (m, 3H), 5.990 (m, 1H), 5.813 (d, J=8.01 Hz, 1H), 5.600 (m, 1H), 5.129 (s, 2H), 5.059–5.014 (m, 2H), 4.590 (m, 1H), 4.420 (m, 1H), 4.270–4.255 (m, 2H), 4.148–4.028 (m, 4H), 3.767 (s, 3H), 3.525 (m, 2H), 3.330 (m, 2H), 2.742 (m, 2H), 1.862 (m, 1H), 1.741 (m, 1H), 1.474–1.425 (bs, 9H), 1.175 (d, J=6.6 Hz, 3H), 0.910 (s, 9H), 0.775 (s, 9H), 0.104 (s, 3H), 0.093 (s, 3H), −0.040 (s, 3H), −0.232 (s, 3H).

Analytical HPLC (4.6×150 mm Phenomenex ODS3 column eluted with a linear gradient of 10–90% acetonitrile in water containing 0.02% trifluoroacetic acid over 16 minutes): 94% at 15.258 minutes.

Example 11 tert-Butyl (2S,3R)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

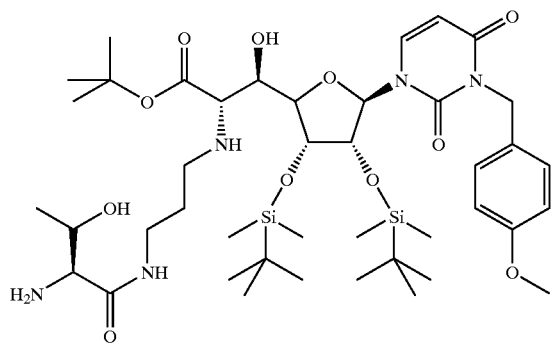

By using an analogous procedure to that described for Example 2, tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(11S)-1-hydroxyethyl]-3,6-dioxo-1-phenyl-2-oxa-4,7,11-triazatridecan-13-oate (146 mg, 0.144 mmol, obtained from Example 10) was hydrogenated in methanol (3 ml) using 10% palladium on carbon (30 mg) to provide tert-butyl (2S,3R)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (123 mg, 97%) as a white amorphous solid.

MS (ES): m/z 880.1 (M+H).

IR cm$^{-1}$: 3373, 1716, 1669.

$^1$H NMR ($\delta$, CDCl$_3$): 8.122 (bs, 1H), 7.382 (d, J=8.7 Hz, 2H), 6.799 (d, J=8.7 Hz, 2H), 5.809 (d, J=7.8 Hz, 1H), 5.680 (m, 1H), 5.077–4.943 (m, 2H), 4.537 (m, 1H), 4.336 (m, 1H), 4.286–4.272 (m, 1H), 4.079–4.053 (m, 2H), 3.771 (s, 3H), 3.454 (m, 2H), 3.287 (m, 1H), 2.810–2.414 (m, 9H), 1.843 (m, 1H), 1.688 (m, 1H), 1.479 (s, 9H), 1.213 (d, J=6.6 Hz, 3H), 0.912 (s, 9H), 0.773 (s, 9H), 0.060 (s, 6H), −0.050 (s, 3H), −0.250 (s, 3H).

Example 12 tert-Butyl (5S,12S)-5-benzyl-12-[(R)-[(3R,4R,5R)-3,4-bis{[tertbutyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate

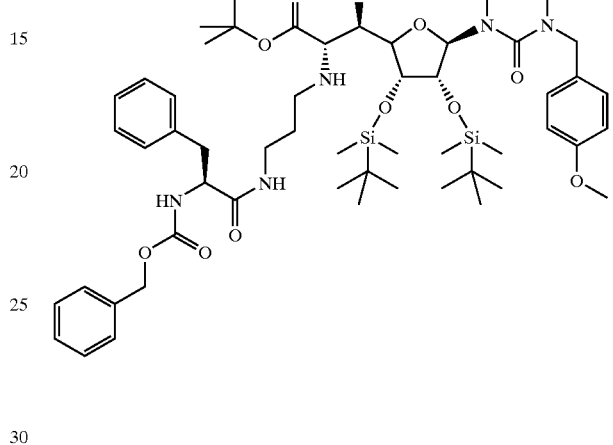

By using an analogous procedure to that described for Example 1, a solution of benzyl (1S)-1-benzyl-2-oxo-2-[(3-oxopropyl)amino]ethylcarbamate (61 mg, 0.173 mmol, obtained from Reference Example 22), tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (100 mg, 0.139 mmol, obtained from Reference Example 6), acetic acid (1 drop), and sodium triacetoxyborohydride (59 mg, 0.277 mmol) in anhydrous tetrahydrofuran (4 ml) was stirred at room temperature under nitrogen for 5 hours. The product was purified by chromatography (flash column, silica gel, 2.5% methanol in methylene chloride) to provide tert-butyl (5S,12S)-5-benzyl-12-[(R)-[(3R,4R,5R)-3,4-bis{[tertbutyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate (31 mg, 21%) as a white solid.

MS (ES): m/z 1060.4 (M+H).

IR cm$^{-1}$: 3382, 1715, 1669.

$^1$H NMR ($\delta$, CDCl$_3$): 7.521–7.193 (m, 13H), 6.787 (d, J=8.64 Hz, 2H), 5.777 (d, J=8.04 Hz, 1H), 5.655–5.609 (m, 1H), 5.434 (m, 1H), 5.069–4.882 (m, 4H), 4.549 (m, 2H), 4.332–4.269 (m, 2H), 4.058–3.944 (m, 1H), 3.756 (s, 3H), 3.384 (m, 2H), 3.181–3.137 (m, 4H), 2.657 (m, 2H), 1.589 (m, 6H), 1.476 (s, 9H), 0.889 (s, 9H), 0.772 (s, 9H), 0.075 (s, 6H), −0.060 (s, 3H), −0.230 (s, 3H).

Example 13 tert-Butyl (2S,3R)-2-[(3-{[(2S)-2-amino-3-phenylpropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

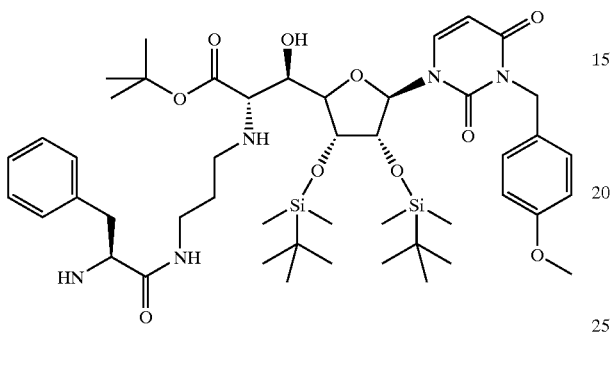

By using an analogous procedure to that described for Example 2, tert-butyl (5S,12S)-5-benzyl-12-[(R)-[(3R,4R,5R)-3,4-bis{[tertbutyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate (Example 12) (49 mg, 0.046 mmol) was hydrogenated in methanol (1.5 ml) using 10% palladium on carbon (12 mg) to provide tert-butyl (2S,3R)-2-[(3-{[(2S)-2-amino-3-phenylpropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (30 mg, 70%) as a white amorphous solid.

MS (ES): m/z 926.4 (M+H).

$^1$H NMR (δ, DMSO-$d_6$): 7.824–7.769 (m, 2H), 7.280–7.145 (m, 7H), 6.826 (d, J=8.73 Hz, 2H), 5.934 (d, J=7.62 Hz, 1H), 5.870 (d, J=8.07 Hz, 1H), 5.649 (d, J=6.15 Hz, 1H), 4.941–4.838 (m, 2H), 4.338–4.298 (m, 1H), 4.219–4.204 (m, 1H), 4.111–4.094 (m, 1H), 3.703 (s, 3H), 3.049–3.026 (m, 2H), 2.929–2.912 (m, 1H), 2.885–2.869 (m, 1H), 2.183 (m, 1H), 2.127 (m, 1H), 1.610–1.205 (m, 8H), 1.420 (s, 9H), 0.885 (s, 9H), 0.713 (s, 9H), 0.092 (s, 3H), 0.073 (s, 3H), −0.060 (s, 3H), −0.229 (s, 3H).

Analytical HPLC (4.6×150 mm Phenomenex ODS3 column eluted with a linear gradient of 10–90% acetonitrile in water containing 0.02% trifluoroacetic acid over 16 minutes): 86% at 13.580 minutes.

Example 14 tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-methyl-3,6-dioxo-1-phenyl-2-oxa-4,7,11-triazatridecan-13-oate

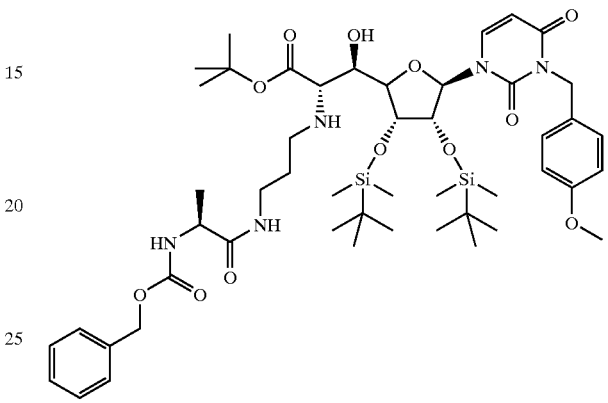

By using an analogous procedure to that described for Example 1, a solution of tert-(4-methoxybenzyl)-2,4-dioxo-3,4-dihydro-1(2H)-pyrimidinyl)-tetrahydro-2-furanyl]-3-hydroxypropanoate (80 mg, 0.111 mmol, obtained from Reference Example 6), benzyl (1S)-1-methyl-2-oxo-2-[(3-oxopropyl)amino]ethylcarbamate (39 mg, 0.139 mmol, obtained from Reference Example 20), acetic acid (1 drop), and sodium triacetoxyborohydride (47 mg, 0.222 mmol) in anhydrous tetrahydrofuran (4 ml) was stirred at room temperature under nitrogen for 3 hours. The product was purified by chromatography (flash column, silica gel, 5% methanol in methylene chloride) to provide tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-methyl-3,6-dioxo-1-phenyl-2-oxa-4,7,11-triazatridecan-13-oate (43 mg, 39%) as a white amorphous solid.

MS (ES): m/z 984.4 (M+H).

IR cm$^{-1}$: 3403, 1714, 1668.

Analytical HPLC (4.6×150 mm Phenomenex ODS3 column eluted with a linear gradient of 10–90% acetonitrile in water containing 0.02% trifluoroacetic acid over 17 minutes): 94% at 16.274 minutes.

Example 15 tert-Butyl (2S,3R)-2-[(3-{[(2S)-2-aminopropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

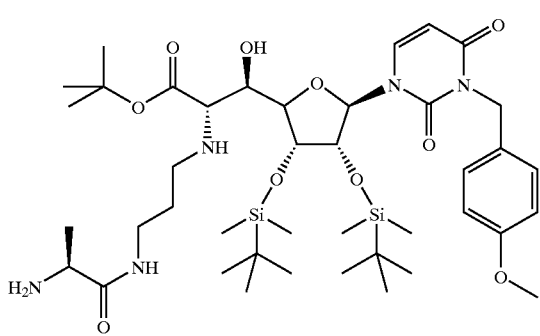

By using an analogous procedure to that described in Example 2, tert-butyl (5S,12S)-dioxo-3,4-dihydro-1(2H)-pyrimidinyl)tetrahydro-2-furanyl](hydroxy)methyl]-5-methyl-3,6-dioxo-1-phenyl-2-oxa-4,7,11-triazatridecan-13-oate (43 mg, 0.044 mmol, obtained from Example 14) was hydrogenated in methanol (1.5 ml) using 10% palladium on carbon (10 mg) to provide tert-butyl (2S,3R)-2-[(3-{[(2S)-2-aminopropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (35 mg, 94%) as a white amorphous solid.

MS (ES): m/z 850.4 (M+H).

$^1$H NMR (δ, DMSO-d$_6$): 7.783 (d, J=8.1 Hz, 2H), 7.234 (d, J=8.67 Hz, 2H), 6.831 (d, J=8.67 Hz, 2H), 5.925 (d, J=7.65 Hz, 1H), 5.865 (d, J=8.07 Hz, 1H), 5.648 (d, J=6.03 Hz, 1H), 4.943–4.836 (m, 2H), 4.317–4.291 (m, 1H), 4.216–4.202 (m, 1H), 4.101 (d, J=5.1 Hz, 1H), 3.705 (bs, 4H), 3.227–3.159 (m, 1H), 3.097–3.054 (m, 2H), 2.326 (m, 2H), 2.157 (m, 2H), 1.760 (m, 2H), 1.521–1.476 (m, 2H), 1.418 (s, 9H), 1.087 (d, J=6.9 Hz, 3H), 0.887 (s, 9H), 0.711 (s, 9H), 0.094 (s, 3H), 0.074 (s, 3H), −0.046 (s, 3H), −0.230 (s, 3H).

Analytical HPLC (4.6×150 mm Phenomenex ODS3 column eluted with a linear gradient of 10–90% acetonitrile in water containing 0.02% trifluoroacetic acid over 17 minutes): 72% at 12.797 minutes.

Example 16 tert-Butyl (5S,12S)-5-[2-(benzyloxy)-2-oxoethyl]-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate

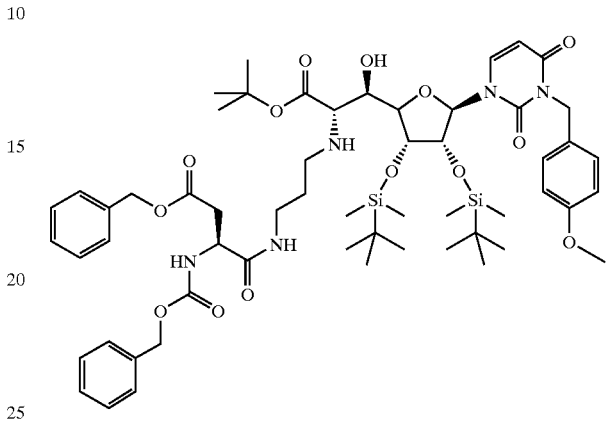

By using an analogous procedure to that described in Example 1, a solution of tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (100 mg, 0.139 mmol, obtained from Reference Example 6), benzyl (3S)-3-{[(benzyloxy)carbonyl]amino}-4-oxo-4-[(3-oxopropyl)amino]butanoate (71 mg, 0.173 mmol, obtained from Reference example 24), acetic acid (1 drop), and sodium triacetoxyborohydride (59 mg, 0.277 mmol) in anhydrous tetrahydrofuran (4 ml) was stirred under nitrogen at room temperature for 5 hours. The product was purified by chromatography (flash column, silica gel, 5% methanol in methylene chloride) to provide tert-butyl (5S,12S)-5-[2-(benzyloxy)-2-oxoethyl]-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate (109 mg, 70%) as a white amorphous solid.

MS (ES): m/z 1118.4 (M+H).

IR cm$^{-1}$: 3403, 1716, 1670.

$^1$H NMR (δ, DMSO-d$_6$): 7.916 (m, 1H), 7.781 (d, J=8.13 Hz, 1H), 7.552 (d, J=8.31 Hz, 1H), 7.341–7.307 (m, 10H), 7.229 (d, J=8.7 Hz, 2H), 6.824 (d, J=8.73 Hz, 2H), 5.926 (d, J=7.68 Hz, 1H), 5.865 (d, J=8.1 Hz, 1H), 5.629 (d, J=6.33 Hz, 1H), 5.069 (s, 2H), 5.024–5.012 (m, 2H), 4.935–4.826 (m, 2H), 4.286–4.340 (m, 1H), 4.327–4.287 (m, 1H), 4.209–4.195 (m, 1H), 4.101–4.084 (m, 1H), 3.725–3.701 (bs, 4H), 3.111–3.049 (m, 2H), 2.794–2.724 (m, 1H), 2.649–2.566 (m, 1H), 2.315 (m, 2H), 2.073 (m, 2H), 1.483 (m, 2H), 1.408 (s, 9H), 0.878 (s, 9H), 0.706 (s, 9H), 0.085 (s, 3H), 0.064 (s, 3H), −0.056 (s, 3H), −0.237 (s, 3H).

Example 17

(3S)-3-Amino-4-[(3-{[(1S,2S)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-4-oxobutanoic acid

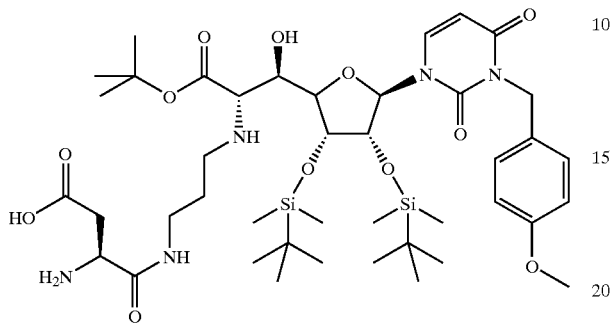

By using an analogous procedure to that described for Example 2, tert-butyl (5S,12S)-5-[2-(benzyloxy)-2-oxoethyl]-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate (20 mg, 0.018 mmol, obtained from Example 16) was hydrogenated in methanol (1.5 ml) using 10% palladium on carbon (10 mg) to provide (3S)-3-amino-4-[(3-{[(1S,2S)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-4-oxobutanoic acid (16 mg, 99%) as a white solid.

MS (ES): m/z 894.3 (M+H), 447.9 (M+2H)$^{2+}$.

IR cm$^{-1}$: 1717, 1673.

Analytical HPLC (4.6×150 mm Phenomenex ODS3 column eluted with a linear gradient of 10–90% acetonitrile in water containing 0.02% trifluoroacetic acid over 17 minutes): 82% at 12.761 minutes.

Example 18 tert-Butyl (9S,16S)-9-{[(benzyloxy)carbonyl]amino}-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,10-dioxo-1-phenyl-2-oxa-4,11,15-triazaheptadecan-17-oate

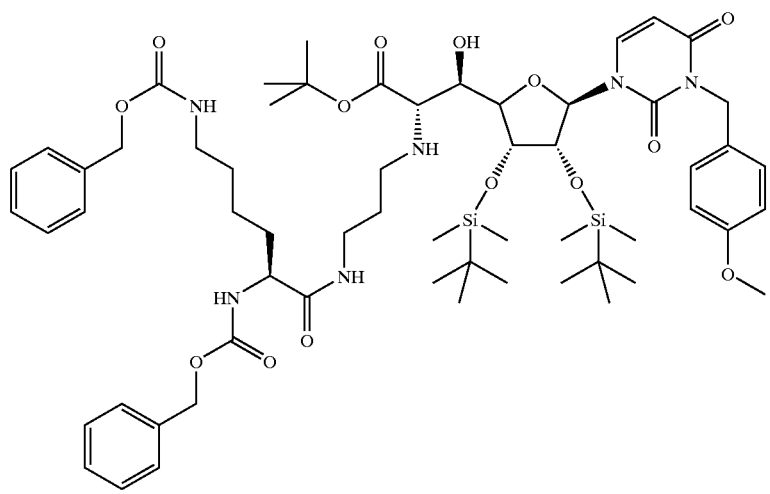

BY using an analogous procedure to that described for Example 1, a solution of tert-(4-methoxybenzyl)-2,4-dioxo-3,4-dihydro-1(2H)-pyrimidinyl)-tetrahydro-2-furanyl]-3-hydroxypropanoate (Reference Example 6) (100 mg, 0.139 mmol), benzyl (5S)-[5-benzyloxycarbonylamino-5-(3-oxo-propylcarbamoyl)-pentyl]-carbamate (71 mg, 0.152 mmol, Reference Example 28), acetic acid (2 drops), and sodium triacetoxyborohydride (59 mg, 0.277 mmol) in anhydrous tetrahydrofuran (4 ml) was stirred under nitrogen at room temperature for 3.5 hours. The product was purified by chromatography (flash column, silica gel, 4% methanol in methylene chloride) to provide tert-butyl (9S,16S)-9-{[(benzyloxy)carbonyl]amino}-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,10-dioxo-1- phenyl-2-oxa-4,11,15-triazaheptadecan-17-oate (92 mg, 56%) as a white amorphous solid.

MS (ES): m/z 1175.5 (M+H).

IR cm⁻¹: 1715, 1669.

¹H NMR (δ, CDCl₃): 7.394–7.293 (m, 13H), 6.783 (d, J=8.61 Hz, 2H), 5.783–5.756 (m, H), 5.696 (m, 1H), 5.565 (m, 1H), 5.076–4.936 (m, 7H), 4.495 (m, 1H), 4.304 (m, 1H), 4.065–4.045 (m, 2H), 3.854 (m, 1H), 3.757 (s, 3H), 3.466 (m, 2H), 3.251–3.174 (m, 4H), 2.723–2.529 (m, 2H), 1.835–1.364 (m, 10H), 1.462 (s, 9H), 0.907 (s, 9H), 0.767 (s, 9H), 0.094 (s, 6H), −0.060 (s, 3H), −0.230 (s, 3H).

Analytical HPLC (4.6×150 mm Prodigy ODS3 column eluted with 10–95% acetonitrile in water containing 0.02% trifluoroacetic acid over 30 minutes): 71% at 17.8 minutes.

Example 19 tert-Butyl (2S,3R)-3-[(3R,4R,5R)-3,4-bis{[tert-butyl (dimethyl)silyl]oxy}-5-(3-(4-methoxybenzyl)-2,4-dioxo-3,4-dihydro-1(2H)-pyrimidinyl)tetrahydro-2-furanyl]-2-[(3-{[(2S)-2,6-diaminohexanoyl] amino}propyl)amino]-3-hydroxypropanoate

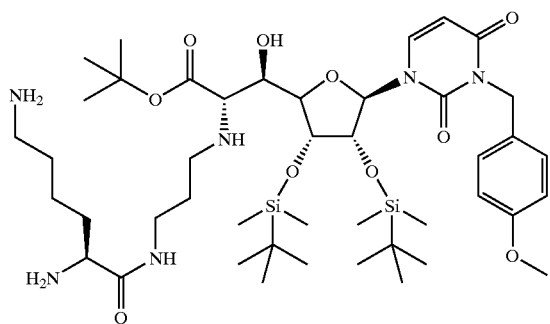

By using an analogous procedure to that described for Example 2, tert-butyl (9S,16S)-9-{[(benzyloxy)carbonyl] amino}-16-[(R)-[(3R,4R,5R)-3,4-bis{[tert-pyrimidinyl) tetrahydro-2-furanyl](hydroxy)methyl]-3,10-dioxo-1-phenyl-2-oxa-4,11,15-triazaheptadecan-17-oate (70 mg, 0.06 mmol, obtained from Example 18) was hydrogenated in methanol (2 ml) using 10% palladium on carbon (17 mg) to provide tert-butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(3-{[(2S)-2,6-diaminohexanoyl]amino}propyl) amino]-3-hydroxypropanoate (50 mg, 92%) as a white solid.

MS (ES): m/z 907.5 (M+H), 454.4 (M+2H)²⁺.

¹H NMR (δ, DMSO-d₆): 7.801–7.775 (m, 2H), 7.234 (d, J=8.64 Hz, 2H), 6.830 (d, J=8.73 Hz, 2H), 5.926 (d, J=7.68 Hz, 1H), 5.868 (d, J=8.04 Hz, 1H), 5.666 (bs, 1H), 4.944–4.835 (m, 2H), 4.333–4.294 (m, 1H), 4.219–4.185 (m, 1H), 4.104–4.088 (m, 1H), 3.705 (m, 2H), 3.315–3.045 (m, 12H), 2.342 (m, 2H), 2.231 (m, 2H), 1.496 (m, 2H), 1.419 (s, 9H), 1.280 (m, 4H), 0.887 (s, 9H), 0.711 (s, 9H), 0.094 (s, 3H), 0.074 (s, 3H), −0.060 (s, 3H), −0.230 (s, 3H).

Analytical HPLC (4.6×150 mm Prodigy ODS3 column eluted with 40–90% acetonitrile in water containing 0.02% trifluoroacetic acid over 23 minutes): 71% at 7.6 minutes.

Example 20 tert-Butyl (5S,12S)-12-[(R)-[(3R,4R,5R)-3,4-bis{ [tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[3-(tert-butoxy)-3-oxopropyl]-3,6-dioxo-1-phenyl-2-oxa-4,7,11-triazatridecan-13-oate

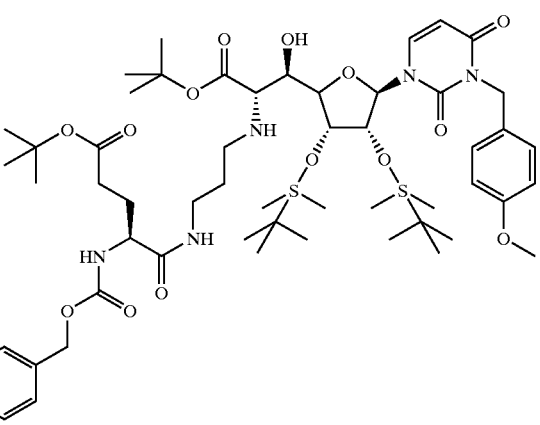

By using an analogous procedure to that described for Example 1, a solution of tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (100 mg, 0.139 mmol, obtained from Reference Example 6), tert-butyl (4S)-4-{[(benzyloxy)carbonyl]amino}-5-oxo-5-[(3-oxopropyl)amino]pentanoate (60 mg, 0.152 mmol, obtained from Reference Example 26), acetic acid (2 drops), and sodium triacetoxyborohydride (59 mg, 0.277 mmol) in anhydrous tetrahydrofuran (4 ml) was stirred under nitrogen at room temperature for 3.5 hours. The product was purified by chromatography (flash column, silica gel, 4% methanol in methylene chloride) to provide tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[3-(tert-butoxy)-3-oxopropyl]-3,6-dioxo-1-phenyl-2-oxa-4,7,11-triazatridecan-13-oate (126 mg, 83%) as a white amorphous solid.

MS (ES): m/z 1098.5 (M+H).

¹H NMR (δ, DMSO-d₆): 7.864–7.827 (m, 1H), 7.789 (d, J=8.2 Hz, 1H), 7.346–7.250 (m, 5H), 7.232 (d, J=8.7 Hz, 2H), 6.827 (d, J=8.7 Hz, 2H), 5.925 (d, J=7.65 Hz, 1H), 5.864 (d, J=8.1 Hz, 1H), 5.634 (d, J=6.36 Hz, 1H), 5.064–4.961 (m, 2H), 4.939–4.831 (m, 2H), 4.326–4.286 (m, 1H), 4.212–4.198 (m, 1H), 3.942–3.924 (m, 1H), 3.747–3.726 (m, 2H), 3.726 (s, 3H), 1.416 (s, 9H), 1.372 (s, 9H), 0.884 (s, 9H), 0.720 (s, 9H), 0.195 (s, 3H), 0.091 (s, 3H), −0.049 (s, 3H), −0.204 (s, 3H).

Analytical HPLC (4.6×150 mm Prodigy ODS3 column eluted with 30–90% acetonitrile in water containing 0.02% trifluoroacetic acid over 23 minutes): 67% at 15.5 minutes.

Example 21 tert-Butyl (4S)-4-amino-5-[(3-{[(1S,2R)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-5-oxopentanoate

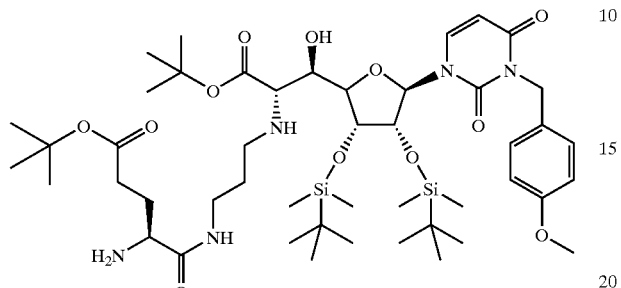

By using an analogous procedure to that described for Example 2, tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[3-(tert-butoxy)-3-oxopropyl]-3,6-dioxo-1-phenyl-2-oxa-4,7,11-triazatridecan-13-oate (94 mg, 0.086 mmol, obtained from Example 20) was hydrogenated in methanol (3 ml) using 10% palladium on carbon (24 mg) to provide tert-butyl (4S)-4-amino-5-[(3-{[(1S,2R)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-5-oxopentanoate (80 mg, 96%) as a white solid.

MS (ES): m/z 964.6 (M+H), 482.9 (M+2H)$^{2+}$.

$^{1}$H NMR (δ, DMSO-d$_6$): 7.801–7.774 (m, 2H), 7.234 (d, J=8.64 Hz, 2H), 6.829 (d, J=8.7 Hz, 2H), 5.925 (d, J=7.74 Hz, 1H), 5.865 (d, J=8.16 Hz, 1H), 5.651 (bs, 1H), 4.943–4.835 (m, 2H), 4.746 (bs, 1H), 4.329–4.289 (m, 1H), 4.216–4.189 (m, 1H), 4.112–4.095 (m, 1H), 3.705 (s, 3H), 3.083–3.059 (m, 5H), 2.330 (m, 2H), 2.242–2.145 (m, 4H), 1.717–1.543 (m, 2H), 1.521–1.475 (m, 2H), 1.418 (s, 9H), 1.380 (s, 9H), 0.886 (s, 9H), 0.727 (s, 9H), 0.094 (s, 3H), 0.073 (s, 3H), −0.046 (s, 3H), −0.205 (s, 3H).

Example 22 tert-Butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(11-{[(9H-fluoren-9-ylmethoxy)carbonyl]amino}undecanoyl)-amino]-3-hydroxypropanoate

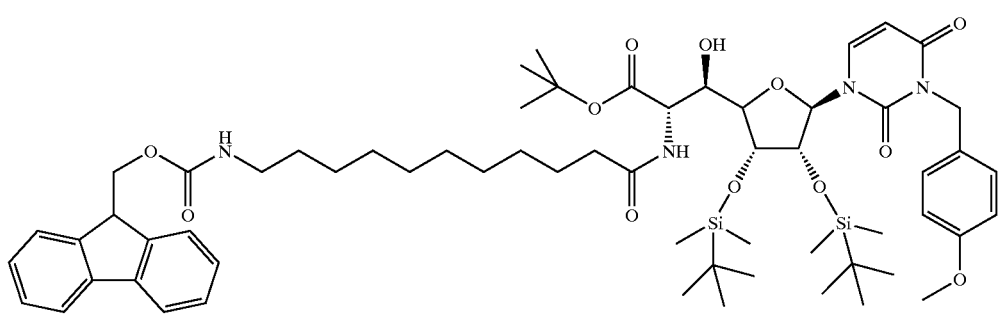

By using an analogous procedure to that described in Reference Example 13, a solution of Fmoc-11-aminoundecanoic acid (62 mg, 0.145 mmol), hydroxybenzotriazole (19 mg, 0.145 mmol), 1-(3-dimethylaminopropyl)-3-ethylcarbodiimide hydrochloride (28 mg, 0.145 mmol), ), tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (100 mg, 0.139 mmol, obtained from Reference Example 6), and N,N-diisopropylethylamine (0.025 mL, 0.145 mmol) in anhydrous tetrahydrofuran (4 ml) was stirred at room temperature under nitrogen for 48 hours. The product was purified by chromatography (flash column, silica gel, 40% ethyl acetate in hexanes) to provide tert-butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(11-[(9H-fluoren-9-ylmethoxy)carbonyl]amino}undecanoyl)amino]-3-hydroxypropanoate (87 mg, 55%) as a white solid.

MS (ES): m/z 1127.2 (M+H).

$^{1}$H NMR (δ, CDCl$_3$): 7.778–7.753 (m, 2H), 7.606–7.583 (m, 2H), 7.532 (d, J=8.1 Hz, 1H), 7.425–7.261 (m, 6H), 6.790 (d, J=8.7 Hz, 2H), 6.440–6.423 (m, 1H), 6.066 (d, J=7.71 Hz, 1H), 5.863 (d, J=8.07 Hz, 1H), 5.085–4.971 (m, 2H), 4.762 (m, 1H), 4.658–4.640 (m, 1H), 4.410–4.388 (m, 2H), 4.240–4.168 (m, 1H), 4.149–4.099 (m, 2H), 3.909–3.837 (m, 1H), 3.762 (s, 3H), 3.197–3.153 (m, 2H), 2.283–2.233 (m, 2H), 1.633 (m, 2H), 1.557–1.469 (m, 2H), 1.421 (s, 9H), 1.286 (bs, 14H), 0.904 (s, 9H), 0.765 (s, 9H), 0.050 (s, 6H), −0.050 (s, 3H), −0.200 (s, 3H).

Analytical HPLC (4.6×150 mm Prodigy ODS3 column eluted with 10–100% isopropanol in water containing 0.02% trifluoroacetic acid over 27 minutes): 90% at 17.9 minutes.

Example 23 tert-Butyl (2S,3R)-2-[(11-aminoundecanoyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

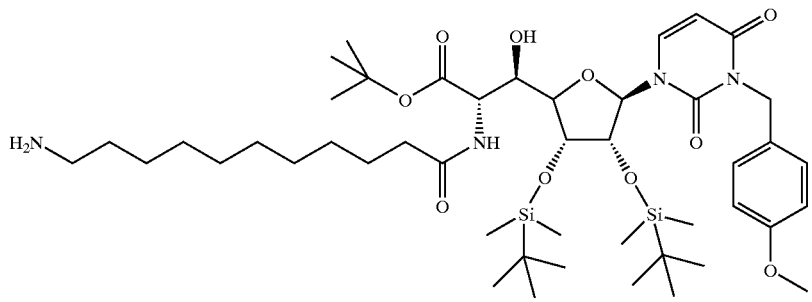

By using an analogous procedure to that described for Reference Example 32, tert-butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(11-{[(9H-fluoren-9-ylmethoxy)carbonyl]amino}undecanoyl)amino]-3-hydroxypropanoate (73 mg, 0.065 mmol, obtained from Example 22) was stirred with piperidine (1.5 ml) for 1 hour under nitrogen at room temperature. The product was purified by chromatography (flash column, silica gel, 50–60% methanol in methylene chloride) to provide tert-butyl (2S,3R)-2-[(11-aminoundecanoyl)amino]-3-[(3R,4R,5R)-3,4-bis{[tert-butyl (dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (38 mg, 65%) as a white solid.

MS(ES): m/z 905.0 (M+H), 452.8 (M+2H)$^{2+}$.

$^1$H NMR (δ, DMSO-d$_6$): 8.020 (d, J=8.28 Hz, 1H), 7.848 (d, J=8.16 Hz, 1H), 7.229 (d, J=8.7 Hz, 2H), 6.829 (d, J=8.76 Hz, 2H), 5.949 (d, J=7.92 Hz, 1H), 5.801 (d, J=8.04 Hz, 1H), 5.734 (m, 1H), 4.932–4.832 (m, 2H), 4.454–4.414 (m, 1H), 4.317–4.276 (m, 1H), 4.241–4.227 (m, 1H), 4.065–3.973 (m, 2H), 3.930–3.901 (m, 1H), 3.703 (s, 3H), 2.211–2.093 (m, 3H), 1.513–1.491 (m, 4H), 1.380 (s, 9H), 1.314–1.093 (m, 14H), 0.886 (s, 9H), 0.706 (s, 9H), 0.050 (s, 6H), −0.0500 (s, 3H), −0.250 (s, 3H).

Analytical HPLC (4.6×150 mm Prodigy ODS3 column eluted with 10–100% acetonitrile in water containing 0.02% trifluoroacetic acid over 25 minutes): 87% at 18.1 minutes.

Example 24 tert-Butyl (21S)-21-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-1-(9H-fluoren-9-yl)-3,15-dioxo-2-oxa-4,16,20-triazadocosan-22-oate

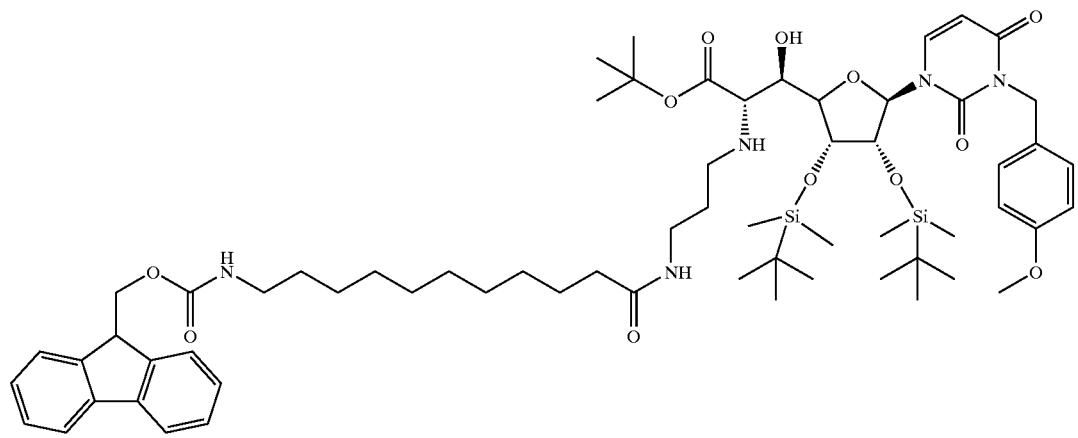

By using an analogous procedure to that described for Example 1, a solution of tert-butyl (2S,3R)-2-amino-3-[(2R,3R,4R,5R)-3,4-bis{[tert-butyl-(dimethyl)silyl]oxy}-5-(3-(4-methoxybenzyl)-2,4-dioxo-3,4-dihydro-1(2H)-pyrimidinyl)-tetrahydro-2-furanyl]-3-hydroxypropanoate (125 mg, 0.173 mmol, obtained from Reference Example 6), 9H-fluoren-9-ylmethyl-11-oxo-11-[(3-oxopropyl)amino]undecyl-carbamate (99 mg, 0.208 mmol, obtained from Reference Example 30), acetic acid (2 drops) and sodium triacetoxyborohydride (73 mg, 0.346 mmol) in anhydrous tetrahydrofuran (4 ml) was stirred at room temperature under nitrogen for 5.5 hours. The product was purified by chromatography (flash column, silica gel, ethyl acetate) to provide tert-butyl (21S)-21-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]

(hydroxy)methyl]-1-(9H-fluoren-9-yl)-3,15-dioxo-2-oxa-4,16,20-triazadocosan-22-oate (133 mg, 65%) as a white solid.

MS (ES): m/z 1184.2 (M+H).

$^1$H NMR (δ, DMSO-d$_6$): 7.897–7.872 (m, 2H), 7.785 (d, J=8.19 Hz, 1H), 7.691–7.666 (m, 2H), 7.433–7.218 (m, 6H), 6.826 (d, J=8.7 Hz, 2H), 5.923 (d, J=7.62 Hz, 1H), 5.861 (d, J=8.1 Hz, 1H), 5.642 (d, J=6.36 Hz, 1H), 4.941–4.832 (m, 2H), 4.322–4.272 (m, 3H), 4.208–4.194 (m, 2H), 4.110–4.094 (m, 1H), 4.041–3.967 (m, 1H), 3.737 (m, 1H), 3.700 (s, 3H), 3.033 (m, 4H), 2.964–2.922 (m, 2H), 2.329 (m, 1H), 2.028–1.978 (m, 4H), 1.585–1.307 (m, 4H), 1.415 (s, 9H), 1.221 (m, 14H), 0.880 (s, 9H), 0.705 (s, 9H), 0.100 (s, 3H), 0.050 (s, 3H), –0.100 (s, 3H), –0.200 (s, 3H).

Analytical HPLC (4.6×150 mm Prodigy ODS3 column eluted with 10–100% acetonitrile in water containing 0.02% trifluoroacetic acid over 25 minutes): 87% at 19.9 minutes.

Example 25 tert-Butyl (2S,3R)-2-({3-[(11-aminoundecanoyl)amino]propyl}amino)-3-[(3R,4R,5R)-3,4-bis{[tert-butyl](dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate

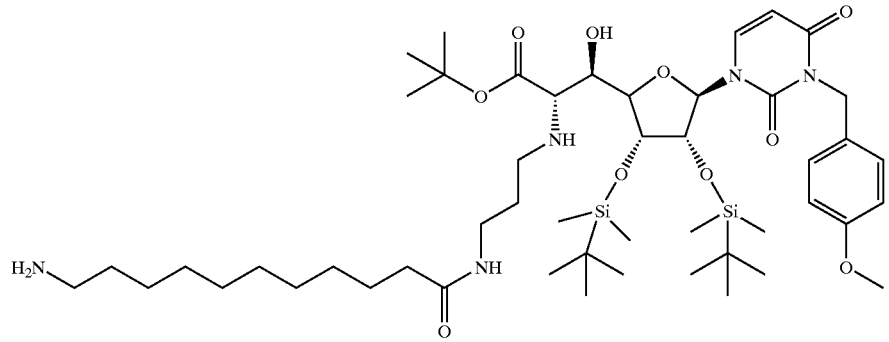

By using an analogous procedure to that described for Reference Example 32, a solution of tert-butyl (21S)-21-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-11-(9H-fluoren-9-yl)-3,15-dioxo-2-oxa-4,16,20-triazadocosan-22-oate (106 mg, 0.09 mmol, obtained from Example 24) in piperidine (3 ml) was stirred for 1.5 hours under nitrogen at room temperature. The product was purified by chromatography (flash column, silica gel, 60–100% methanol in methylene chloride) to provide tert-butyl (2S,3R)-2-({3-[(11-aminoundecanoyl)amino]propyl}amino)-3-[(3R,4R,5R)-3,4-bis{[tert-butyl (dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (44 mg, 51%) as a white solid.

MS (ES): m/z 962.4 (M+H), 482.1 (M+2H)$^{2+}$.

$^1$H NMR (δ, DMSO-d$_6$): 7.817–7.790 (m, 1H), 7.775–7.706 (m, 1H), 7.234 (d, J=8.7 Hz, 2H), 6.829 (d, J=8.73 Hz, 2H), 5.925 (d, J=7.62 Hz, 1H), 5.863 (d, J=8.1 Hz, 1H), 4.943–4.835 (m, 2H), 4.327–4.287 (m, 1H), 4.213–4.199 (m, 1H), 4.108–4.092 (m, 1H), 3.704 (bs, 4H), 3.462–3.309 (m, 7H), 3.052–3.030 (m, 2H), 2.883 (m, 1H), 2.330–2.272 (m, 1H), 2.029–1.980 (m, 2H), 1.474–1.452 (m, 4H), 1.418 (s, 9H), 1.223 (bs, 14H), 0.885 (s, 9H), 0.709 (s, 9H), 0.100 (s, 3H), 0.050 (s, 3H), –0.050 (s, 3H), –0.25 (s, 3H).

Analytical HPLC (4.6×150 mm Prodigy ODS3 column eluted with 10–100% acetonitrile in water containing 0.02% trifluoroacetic acid over 25 minutes): 95% at 14 minutes.

Example 26

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxy-2-methylpropyl]-2-isopropyl-4,7,10-trioxo-3,5,8,11,15-pentaazaheptadecane-1,17-dioate

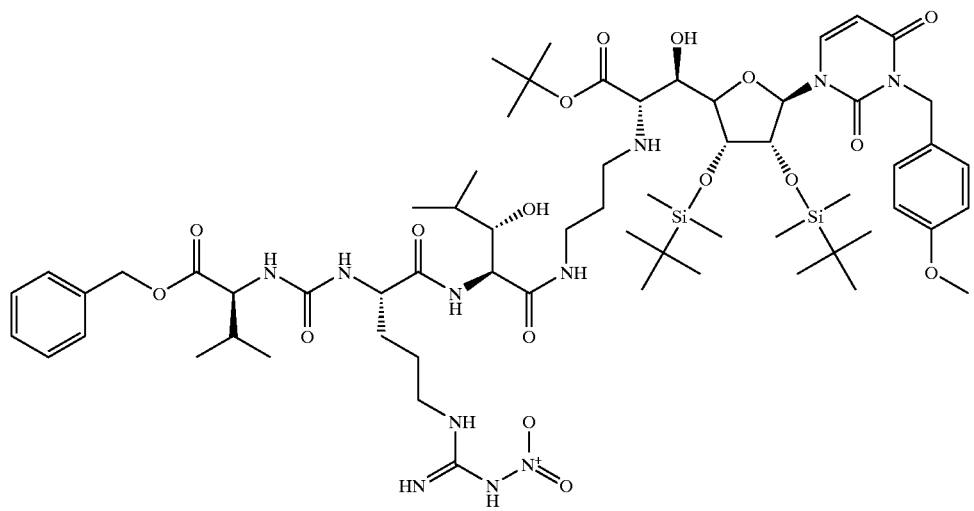

To a solution of (2S)-2-{[({(1S)-1-[(benzyloxy)carbonyl]-2-methylpropyl}amino)carbonyl]amino}-5-{[(2,2-dioxido-2lambda~1~-diazanyl)-(imino)methyl]amino}pentanoic acid (59 mg, 0.13 mmol, obtained from Reference Example 34) in anhydrous tetrahydrofuran (2 ml) were added hydroxybenzotriazole (18 mg, 0.13 mmol) and 1-(3-dimethylaminopropyl)-3-ethylcarbodiimide hydrochloride (25 mg, 0.13 mmol) at room temperature under nitrogen. The resulting solution was stirred at this condition for 30 minutes, and a solution of tert-butyl (2S,3R)-2-[(3-{[(2S,3S)-2-amino-3-hydroxy-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxy-propanoate (113 mg, 0.12 mmol, obtained from Example 2) in anhydrous tetrahydrofuan (2 ml) and N,N-diisopropylethylamine (4 drops) were added. The mixture was stirred at room temperature for an additional 15 hours under nitrogen. The reaction mixture was partitioned between ethyl acetate (30 ml) and water (15 ml). The organic layer was separated, and the aqueous layer was extracted with ethyl acetate (2×30 mL). The combined extracts were washed with saturated aqueous sodium bicarbonate solution and saturated sodium chloride solution, dried over sodium sulfate, filtered and concentrated in vacuo. The resultant solid was purified by chromatography (flash column, silica gel, 7% methanol in methylene chloride) to provide 1-benzyl 17-(tert-butyl) (2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxy-2-methylpropyl]-2-isopropyl-4,7,10-trioxo-3,5,8,11,15-pentaazaheptadecane-1,17-dioate (108 mg, 67%) as a white solid.

MS (ES): m/z 1342.4 (M+H), 671.9 (M+2H)$^{2+}$.

IR cm$^{-1}$: 3373, 1665.

Analytical HPLC (4.6×150 mm Phenomenex ODS3 column eluted with a linear gradient of 10–90% acetonitrile in water containing 0.02% trifluoroacetic acid over 17 minutes): 80% at 16.183 minutes.

Example 27

(2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-19,19-dimethyl-4,7,10,17-tetraoxo-18-oxa-3,5,8,11,15-pentaazaicosan-1-oic acid

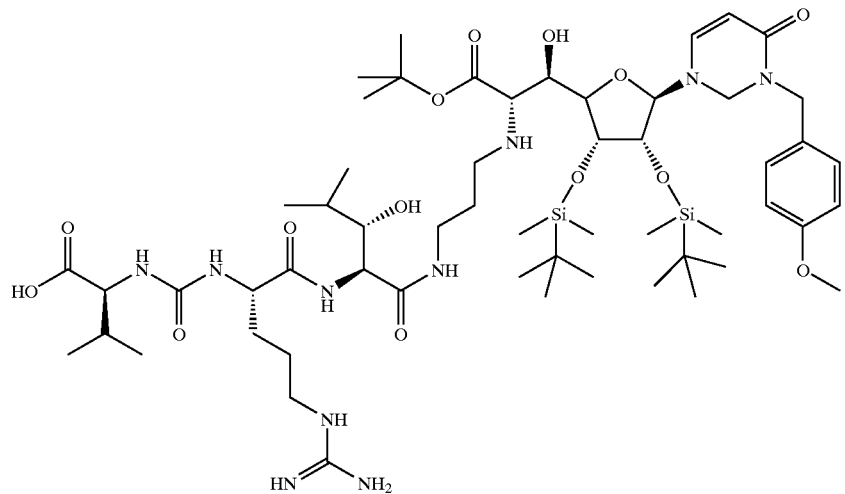

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxy-2-methyl propyl]-2-isopropyl-4,7,10-trioxo-3,5,8,11,15-pentaazaheptadecane-1,17-dioate (10 mg, 0.0075 mmol, obtained from Example 26) was hydrogenated in methanol (2 ml) using 10% palladium on carbon (7 mg) under atmospheric pressure. The catalyst was removed and the filtrate was concentrated in vacuo to provide (2S,6S,9S,16S)-6-(3-{[amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-19,19-dimethyl-4,7,10,17-tetraoxo-18-oxa-3,5,8,11,15-pentaazaicosan-1-oic acid (7 mg, 77%) as a gray solid.

MS (ES): m/z 1207.3 (M+H), 604.4 (M+2H)$^{2+}$.

Example 28

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate

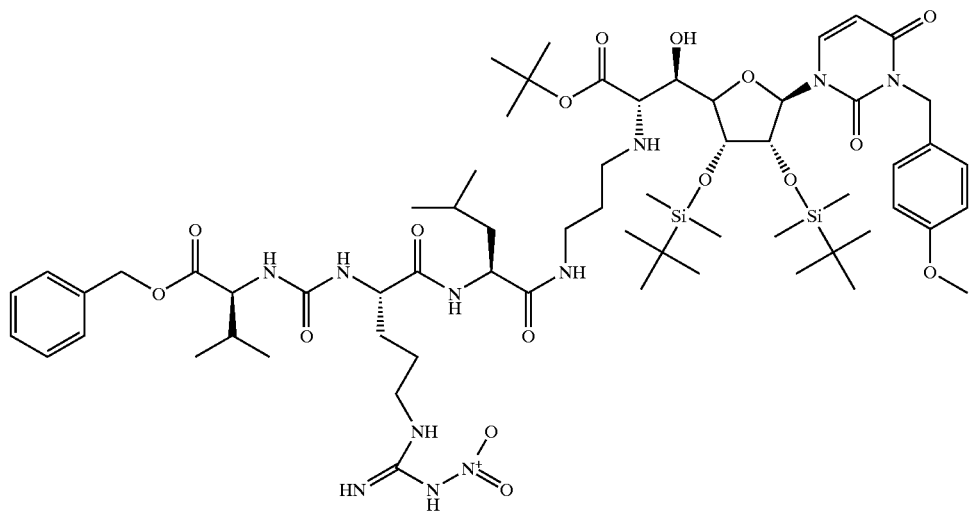

By using an analogous procedure to that described in Example 26, a solution of (2S)-2-{[({(1S)-1-[(benzyloxy)carbonyl]-2-methylpropyl}amino)carbonyl]amino}-5-{[(2,2-dioxido-2lambda~1~-diazanyl)-(imino)methyl]amino}pentanoic acid (71 mg, 0.158 mmol, obtained from Reference Example 34), hydroxybenzotriazole (21 mg, 0.158 mmol), tert-butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (134 mg, 0.15 mmol, obtained from Example 5), 1-(3-dimethylaminopropyl)-3-ethylcarbodiimide hydrochloride (30 mg, 0.158 mmol) and N,N-diisopropylethylamine (4 drops) in anhydrous tetrahydrofuran (6 ml) was stirred at room temperature under nitrogen for 16 hours. The product was purified by chromatography (flash column, silica gel, 5% methanol in methylene chloride) to provide 1-benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate (88 mg, 44%) as a white amorphous solid.

MS (ES): m/z 1326.4 (M+H), 663.8 (M+2H)$^{2+}$.

IR cm$^{-1}$: 3354, 1666.

Analytical HPLC (4.6×150 mm Phenomenex ODS3 column eluted with a linear gradient of 10–90% acetonitrile in water containing 0.02% trifluoroacetic acid over 17 minutes): 76% at 16.351 minutes.

Example 29

(2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-19,19-dimethyl-4,7,10,17-tetraoxo-18-oxa-3,5,8,11,15-pentaazaicosan-1-oic acid

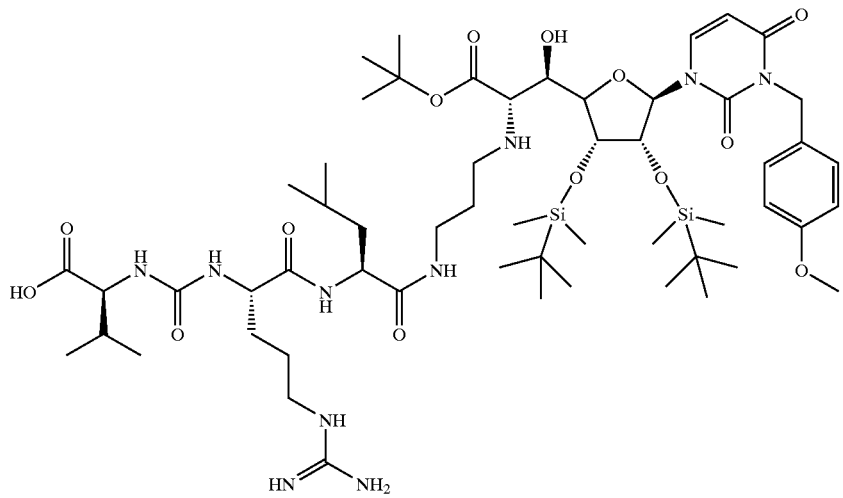

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate (10 mg, 0.0075 mmol, obtained from Example 28) was hydrogenated in 0.1% acetic acid in methanol (2 ml) using 10% palladium on carbon (8 mg) under atmospheric pressure, to provide (2S,6S,9S,16S)-6-(3-{[amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-19,19-dimethyl-4,7,10,17-tetraoxo-18-oxa-3,5,8,11,15-pentaazaicosan-1-oic acid (5.4 mg, 60%) as a gray solid.

MS (ES): m/z 1191.3 (M+H), 596.5 (M+2H)$^{2+}$.

Example 30

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxyethyl]-2-isopropyl-4,7,10-trioxo-3,5,8,11,15-pentaazaheptadecane-1,17-dioate

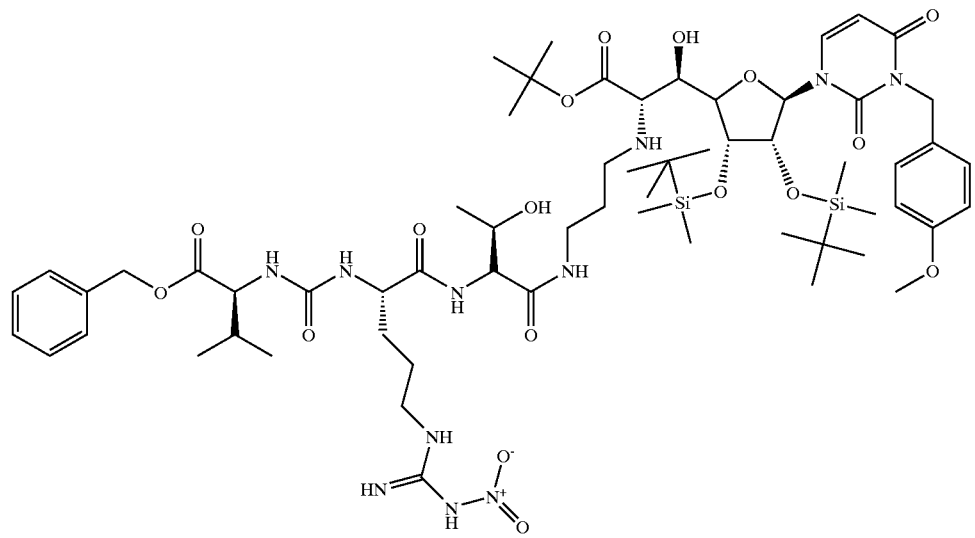

By using an analogous procedure to that described for Example 26, (2S)-2-{[({(1S)-1-[(benzyloxy)carbonyl]-2-methylpropyl}amino)carbonyl]amino}-5-{[(2,2-dioxido-2lambda~1~-diazanyl)-(imino)methyl]amino}pentanoic acid (53 mg, 0.117 mmol, obtained from Reference Example 34), hydroxybenzotriazole (16 mg, 0.117 mmol), tert-butyl (2S,3R)-2-[(3-{[(2S,3S)-2-amino-3-hydroxybutanoyl]amino}propyl)amino]-3-[(3R,4R,5R)-3,4-bis{[tert-butyl(dimethyl) silyl]oxy}-5-(3-(4-methoxybenzyl)-2,4-dioxo-3,4-dihydro-1(2H)-pyrimidinyl)tetrahydro-2-furanyl]-3-hydroxypropanoate (98 mg, 0.111 mmol, obtained from Example 11), 1-(3-dimethylaminopropyl)-3-ethylcarbodiimide hydrochloride (22 mg, 0.117 mmol) and N,N-diisopropylethylamine (4 drops) were stirred in anhydrous tetrahydrofuran (5 ml) at room temperature under nitrogen for 16 hours. The product was purified by chromatography (flash column, silica gel, 7% methanol in methylene chloride) to provide 1-benzyl 17-(tert-butyl) (2S,6S,9S, 16S)-16-[(R)-[(3R,4R,5R)-3,4-bis{[tert-butyl(dimethyl) silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxyethyl]-2-isopropyl-4,7,10-trioxo-3,5,8,11,15-pentaazaheptadecane-1,17-dioate (84 mg, 58%) as a white solid.

MS (ES): m/z 1314.3 (M+H), 657.9 (M+2H)$^{2+}$.

IR cm$^1$: 3345, 1665.

Analytical HPLC (4.6×150 mm Phenomenex ODS3 column eluted with a linear gradient of 10–90% acetonitrile in water containing 0.02% trifluoroacetic acid over 17 minutes): 73% at 14.935 minutes.

Example 31

Ethyl (5S)-12-[(R)-[(2R,3R,4R,5S)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate

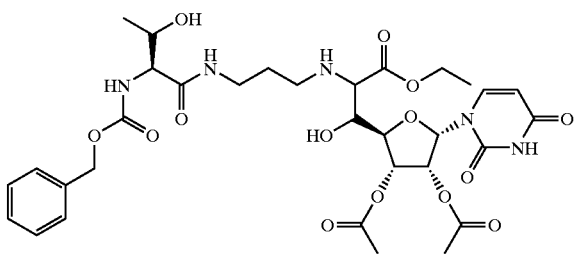

and

103

Ethyl (5S)-12-[(R)-[(2R,3R,4R,5R)-3,4-bis
(acetyloxy)-5-(2,4-dioxo-3,4-dihydro-1(2H)-
pyrimidinyl)tetrahydro-2-furanyl](hydroxy)methyl]-
5-[(1S)-1-hydroxyethyl]-3,6-dioxo-11-phenyl-2-oxa-
4,7,11-triazatridecan-13-oate

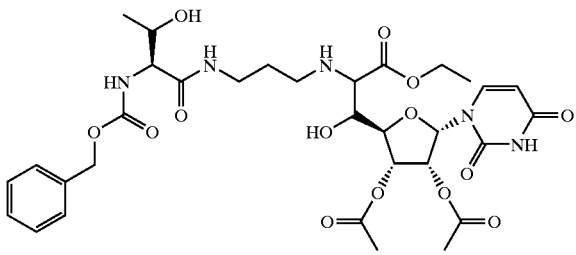

A mixture of ethyl (2R,3R)-2-amino-3-hydroxy-3-[(2S, 3R,4R,5R)-3,4-bis(acetyloxy)-5-(2,4-dioxo-3,4-dihydro-1 (2H)-pyrimidinyl)tetrahydro-2-furanyl]propanoate and ethyl dihydro-1(2H)-pyrimidinyl)tetrahydro-2-furanyl] propanoate (a 3:1 mixture) was obtained by hydrogenation of a mixture of ethyl (2R,3R)-2-{[(benzyloxy)carbonyl] amino}-3-{[(benzyloxy)carbonyl]oxy}-3-[(2S,3R,4R,5R)- 3,4-bis(acetyloxy)-5-(2,4-dioxo-3,4-dihydro-1(2H)- pyrimidinyl)tetrahydro-2-furanyl]propanoate and ethyl (2R, 3R)-2-{[(benzyloxy)carbonyl]amino}-3-{[(benzyloxy) carbonyl]oxy}-3-[(2S,3R,4R,5S)-3,4-bis(acetyloxy)-5-(2,4- dioxo-3,4-dihydro-1(2H)-pyrimidinyl)tetrahydro-2-furanyl] propanoate (obtained from Reference Example 41) using 10% palladium on carbon in absolute methanol under atmospheric pressure at room temperature. The catalyst was removed by filtration, and the filtrate was concentrated in vacuo, to give the desired amine mixture [MS (ES) 430 (M+H)].

A solution of [(1S,2S)-2-hydroxy-1-(3-oxo-propylcarbamoyl)-propyl]-carbamic acid benzyl ester (215 mg, 0.699 mmol, obtained from Reference Example 18) and a mixture of ethyl (2R,3R)-2-amino-3-hydroxy-3-[(2S,3R, 4R,5R)-3,4-bis(acetyloxy)-5-(2,4-dioxo-3,4-dihydro-1(2H)- pyrimidinyl)tetrahydro-2-furanyl]propanoate and ethyl (2R, 3R)-2-amino-3-hydroxy-3-[(2S,3R,4R,5S)-3,4-bis (acetyloxy)-5-(2,4-dioxo-3,4-dihydro-1(2H)-pyrimidinyl) tetrahydro-2-furanyl]propanoate (300 mg, 0.699 mmol) in anhydrous tetrahydrofuran (3 ml) were stirred at room temperature under a nitrogen atmosphere for 15 minutes. Acetic acid (40 μl) and sodium triacetoxyborohydride (0.296 mg, 1.4 mmole) were added and the resulting solution was stirred under nitrogen for an additional 2.5 hours. The reaction mixture was partitioned between ethyl acetate and aqueous sodium bicarbonate solution, and the aqueous layer was separated and extracted with ethyl acetate (2×75 ml). The combined extracts were washed with saturated sodium chloride solution, dried over sodium sulfate, filtered and concentrated in vacuo. The residue was chromatographed (flash column, silica gel, 5% methanol in methylene chloride) to provide ethyl (5S)-12-[(R)-[(2R,3R,4R,5S)-3,4- bis(acetyloxy)-5-(2,4-dioxo-3,4-dihydro-1(2H)- pyrimidinyl)tetrahydro-2-furanyl](hydroxy)methyl]-5- [(1S)-1-hydroxyethyl]-3,6-dioxo-1-phenyl-2-oxa-4,7,11- triazatridecan-13-oate (230 mg, 46%) as a white solid.

MS (ES): m/z 722.2 (M+H).

IR cm$^{-1}$: 3371, 1748, 1698, 1242.

Further elution provided ethyl (5S)-12-[(R)-[(2R,3R,4R, 5R)-3,4-bis(acetyloxy)-5-(2,4-dioxo-3,4-dihydro-1(2H)- pyrimidinyl)tetrahydro-2-furanyl](hydroxy)methyl]-5- [(1S)-1-hydroxyethyl]-3,6-dioxo-1-phenyl-2-oxa-4,7,11- triazatridecan-13-oate (117 mg, 23%) as white solids.

104

MS (ES): m/z 722.3 (M+H).

IR cm$^{-1}$: 3344, 1711, 1243.

Example 32

Ethyl (3R)-2-[(3-{[(2S,3S)-2-amino-3-
hydroxybutanoyl]amino}propyl)amino]-3-[(2R,3R,
4R,5S)-3,4-bis(acetyloxy)-5-(2,4-dioxo-3,4-dihydro-
1(2H)-pyrimidinyl)tetrahydro-2-furanyl]-3-
hydroxypropanoate

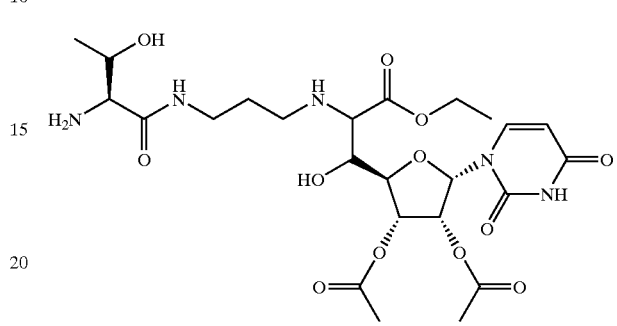

Ethyl (5S)-12-[(R)-[(2R,3R,4R,5S)-3,4-bis(acetyloxy)-5- (2,4-dioxo-3,4-dihydro-1(2H)-pyrimidinyl)tetrahydro-2- furanyl](hydroxy)methyl]-5-[(1S)-1-hydroxyethyl]-3,6- dioxo-1-phenyl-2-oxa-4,7,11-triazatridecan-13-oate (194 mg, 0.269 mmol, obtained from Example 31) was hydrogenated using 10% palladium on carbon in methanol (3 ml) under atmospheric pressure. The catalyst was removed and the volatiles were removed in vacuo to provide ethyl (3R)- 2-[(3-{[(2S,3S)-2-amino-3-dioxo-3,4-dihydro-1(2H)- pyrimidinyl)tetrahydro-2-furanyl]-3-hydroxypropanoate (155 mg, 98%) as a white solid.

MS (ES): m/z 588.3 (M+H), 295.8 (M+2H)$^{2+}$.

IR cm$^{-1}$: 3388, 1746, 1704.

Example 33

Ethyl (3R)-2-[(3-{[(2S,3S)-2-amino-3-
hydroxybutanoyl]amino}propyl)amino]-3-[(2R,3R,
4R,5R)-3,4-bis(acetyloxy)-5-(2,4-dioxo-3,4-dihydro-
1(2H)-pyrimidinyl)tetrahydro-2-furanyl]-3-
hydroxypropanoate

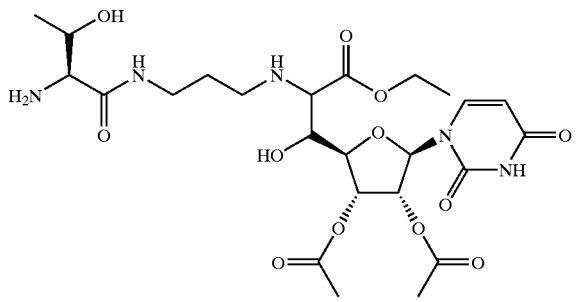

Ethyl (5S)-12-[(R)-[(2R,3R,4R,5R)-3,4-bis(acetyloxy)-5- (2,4-dioxo-3,4-dihydro-1(2H)-pyrimidinyl)tetrahydro-2- furanyl](hydroxy)methyl]-5-[(1S)-1-hydroxyethyl]-3,6- dioxo-1-phenyl-2-oxa-4,7,11-triazatridecan-13-oate (86 mg, 0.119 mmole, obtained from Example 31) was hydrogenated using 10% palladium on carbon in methanol (2 ml) under atmospheric pressure. The catalyst was removed and the volatiles were removed in vacuo to provide ethyl (3R)-2- [(3-{[(2S,3S)-2-amino-3-hydroxybutanoyl]amino}propyl)

amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate (66 mg, 94%) as a white amorphous solid.

MS (ES): m/z 588.3 (M+H), 294.8 (M+2H)$^{2+}$.

IR cm$^{-1}$: 3324, 1694, 1241.

Example 34

16-Benzyl 2-ethyl (1R,9S,12S,16S)-1-[(2R,3R,4R,5S)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate washed with aqueous sodium bicarbonate solution and saturated sodium chloride solution, dried over sodium sulfate, filtered and concentrated in vacuo. The residue was chromatographed (flash column, silica gel, 5% methanol in methylene chloride) to provide 16-benzyl 2-ethyl (1R,9S,12S,16S)-1-[(2R,3R,4R,5S)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate (59 mg, 25%) as a white solid.

MS (ES): m/z 1022.3 (M+H), 511.9 (M+2H)$^{2+}$.

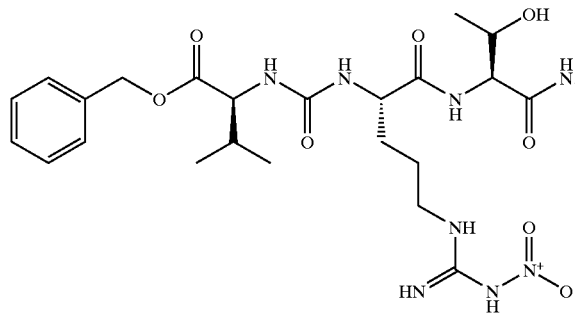
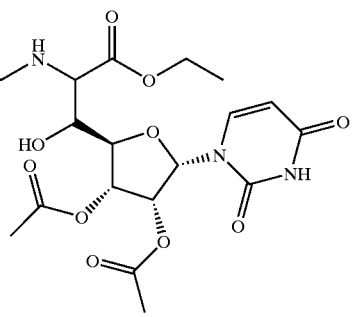

To a solution of (2S)-2-{[([{(1S)-1-[(benzyloxy)carbonyl]-2-methylpropyl}amino)carbonyl]amino}-5-{[(2,2-dioxido-2lambda~1~-diazanyl)(imino)methyl]amino}pentanoic acid (111 mg, 0.245 mmole, obtained from Reference Example 34) in anhydrous tetrahydrofuran (1 ml) was added hydroxybenzotriazole (33 mg, 0.245 mmole) and 1-(3-dimethylaminopropyl)-3-ethylcarbodiimide hydrochloride (47 mg, 0.245 mmole). The resulting solution was stirred at room temperature under a nitrogen atmosphere for 30 minutes. A solution of ethyl (3R)-2-[(3-{[(2S,3S)-2-amino-3-hydroxybutanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]-3-hydroxypropanoate (137 mg, 0.233 mmole, obtained from

Example 35

16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate

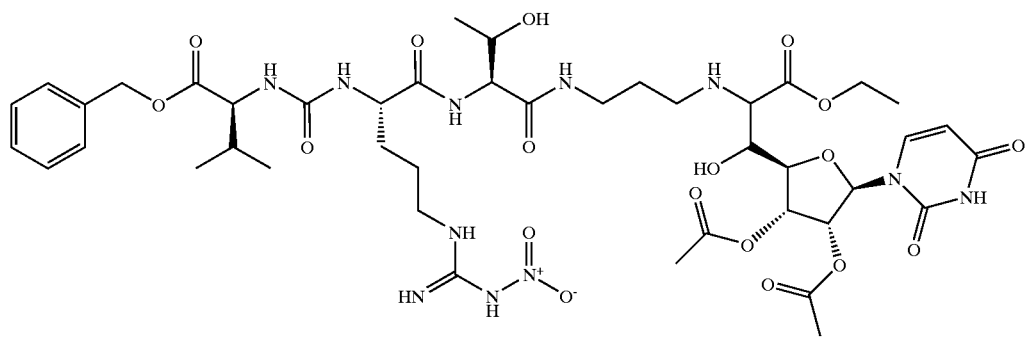

Example 32) in tetrahydrofuran (2 ml) and N,N-diisopropylethylamine (43 □l, 32 mg, 0.245 mmole) were added and stirred at room temperature for 16 hours. The reaction mixture was partitioned between ethyl acetate (75 ml) and water (30 ml). The aqueous layer was separated and extracted with ethyl acetate (2×75 ml), the extracts were To a solution of (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoic acid (47 mg, 0.104 mmole, obtained from Reference Example 34) in anhydrous tetrahydrofuran (0.5 ml) was added hydroxybenzotriazole (14 mg, 0.104 mmole)

and 1-(3-dimethylaminopropyl)-3-ethylcarbodiimide hydrochloride (20 mg, 0.104 mmole). The resulting solution was stirred at room temperature under a nitrogen atmosphere for 30 minutes. A solution of ethyl (3R)-2-[(3-{[(2S,3S)-2-amino-3-hydroxybutanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate (58 mg, 0.0988 mmol, contained from Example 33) in tetrahydrofuran (1.5 ml) and N,N-diisopropylethylamine (2 drops) were added and stirred at room temperature for 16 hours. The reaction mixture was partitioned between ethyl acetate (40 ml) and water (10 ml). The aqueous layer was separated and extracted with ethyl acetate (2×40 ml), the extracts were washed with aqueous sodium bicarbonate solution and saturated sodium chloride solution, dried over sodium sulfate, filtered and concentrated in vacuo. The residue was chromatographed (flash column, silica gel, 10% methanol in methylene chloride) to provide 16-benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate (23 mg, 22%) as a white solid.

MS (ES): m/z 1022.2 (M+H).

Example 36

Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate

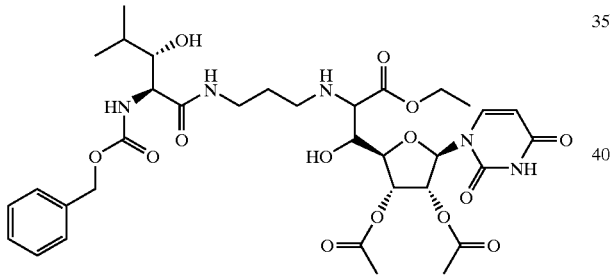

A solution of [2-hydroxy-3-methyl-1-(3-oxopropylcarbamoyl)-butyl]-carbamic acid benzyl ester (313 mg, 0.93 mmol, obtained from Reference Example 14) and ethyl (2R,3R)-2-amino-3-hydroxy-3-[(2S,3R,4R,5R)-3,4-bis(acetyloxy)-5-(2,4-dioxo-3,4-dihydro-1(2H)-pyrimidinyl)tetrahydro-2-furanyl]propanoate [400 mg, 0.93 mmol, obtained by hydrogenation of ethyl (2R,3R)-2-{[(benzyloxy)carbonyl]amino}-3-{[(benzyloxy)carbonyl]oxy}-3-[(2S,3R,4R,5R)-3,4-bis(acetyloxy)-5-(2,4-dioxo-3,4-dihydro-1(2H)-pyrimidinyl)tetrahydro-2-furanyl]propanoate (from Reference Example 41)] in anhydrous tetrahydrofuran (7 ml) was stirred at room temperature under a nitrogen atmosphere for 15 minutes. Acetic acid (53 μl) and sodium triacetoxyborohydride (395 mg, 1.86 mmol) were added, and the resulting solution was stirred for 3 hours. The reaction mixture was partitioned between ethyl acetate and aqueous sodium bicarbonate solution and the aqueous layer was separated and extracted with ethyl acetate (2×75 ml). The combined extracts were washed with saturated sodium chloride solution, dried over sodium sulfate, filtered and concentrated in vacuo. The residue was purified by preparative HPLC (250×21 mm Phenomenex Prodigy ODS3 column eluted with 10–90% acetonitrile in water containing 0.02% trifluoroacetic acid over 72 minutes) to provide ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate as white amorphous solid.

MS (ES): m/z 750.1 (M+H).

IR cm$^{-1}$: 3419, 1693.

Example 37

16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-hydroxy-2-methylpropyl]-17-methyl-8,11,14-trioxo-3,7,10,13,15-pentaazaoctadecane-2,16-dicarboxylate

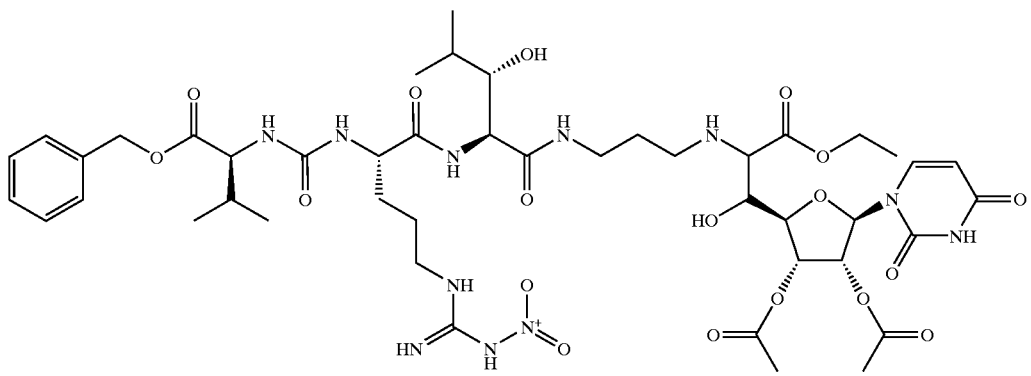

Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate (obtained from Example 36) was hydrogenated using 10% palladium on carbon in absolute methanol under atmospheric pressure, to give ethyl (3R)-2-[(3-{[(2S,3S)-2-amino-3-hydroxy-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate as a white amorphous solid [MS (ES) 616.1 (M+H)].

To a solution of (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoic acid (140 mg, 0.311 mmole, obtained from Reference Example 34) in anhydrous tetrahydrofuran (2 ml) was added hydroxybenzotriazole (42 mg, 0.311 mmole) and 1-(3-dimethylaminopropyl)-3-ethylcarbodiimide hydrochloride (60 mg, 0.311 mmole). The resulting solution was stirred at room temperature under a nitrogen atmosphere for 30 minutes. A solution of ethyl (3R)-2-[(3-{[(2S,3S)-2-amino-3-hydroxy-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate (182 mg, 0.296 mmole) in tetrahydrofuran (2 ml) and N,N-diisopropylethylamine (54 µl, 40 mg, 0.311 mmole) were added and stirred at room temperature for 16 hours. The reaction mixture was partitioned between ethyl acetate (75 ml) and water (40 ml). The aqueous layer was separated and extracted with ethyl acetate (2×75 ml), the extracts were washed with aqueous sodium bicarbonate solution and saturated sodium chloride solution, dried over sodium sulfate, filtered and concentrated in vacuo. The residue was chromatographed (flash column, silica gel, 7.5% methanol in methylene chloride) to provide 16-benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-[[(2,2-dioxido-2lambda~1~-diazanyl)(imino) methyl]amino}propyl)-1-hydroxy-9-[(1S)-hydroxy-2-methylpropyl]-17-methyl-8,11,14-trioxo-3,7,10,13,15-pentaazaoctadecane-2,16-dicarboxylate (125 mg, 40%) as a white solid.

MS (ES): m/z 1050.5 (M+H).

IR cm⁻¹: 3338, 1740, 1690, 1251.

Example 38

Ethyl (5S)-12-{(R)-(acetyloxy)[(2R,3R,4R,5S)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate

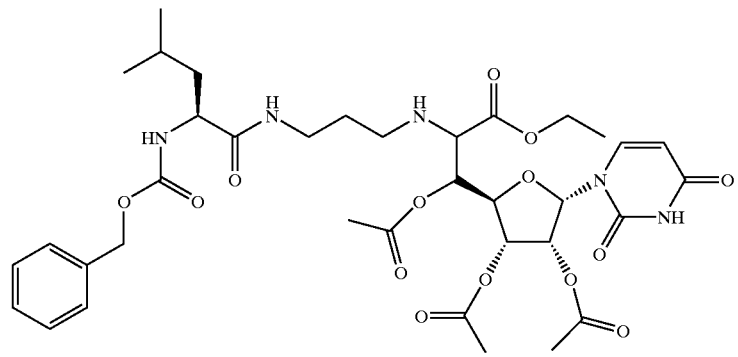

Ethyl (5S)-12-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate

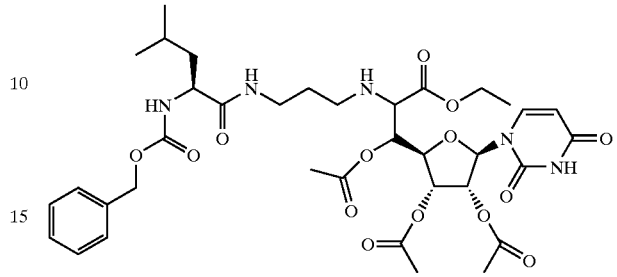

To a solution of [(1S)-3-methyl-1-(3-oxo-propylcarbamoyl)-butyl]-carbamic acid benzyl ester (218 mg, 0.682 mmole, obtained from Reference Example 16) and the hydrogen chloride salt mixture of ethyl (2R,3R)-3-(acetyloxy)-2-dihydro-1(2H)-pyrimidinyl)tetrahydro-2-furanyl]propanoate and ethyl (2R,3R)-3-(2,4-dioxo-3,4-dihydro-1(2H)-pyrimidinyl)tetrahydro-2-furanyl]propanoate (346 mg, 0.682 mmole, obtained from Reference Example 46) in anhydrous tetrahydrofuran (4 ml) were added sodium triacetoxyborohydride (289 mg, 1.36 mmol) and acetic acid (4 drops). The resulting solution was stirred at room temperature under a nitrogen atmosphere for 2 hours. The reaction mixture was partitioned between ethyl acetate and aqueous sodium bicarbonate solution and the aqueous layer was separated and extracted with ethyl acetate (2×75 ml). The combined extracts were washed with saturated sodium chloride solution, dried over magnesium sulfate, filtered and concentrated in vacuo. The residue was chromatographed (flash column, silica gel, ethyl acetate) to provide ethyl (5S)-12-{(R)-(acetyloxy)[(2R,3R,4R,5S)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate as a colorless glass.

MS (ES): m/z 776.2 (M+H).

IR cm⁻¹: 3327, 1701, 1239.

Further elution provided ethyl (5S)-12-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate as a white solid.

MS (ES): m/z 776.5 (M+H).

IR cm$^{-1}$: 3393, 1697, 1241.

Example 39

Ethyl (3R)-3-(acetyloxy)-2-[(3-{[(2S)-2-amino-4-methylpentanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]propanoate

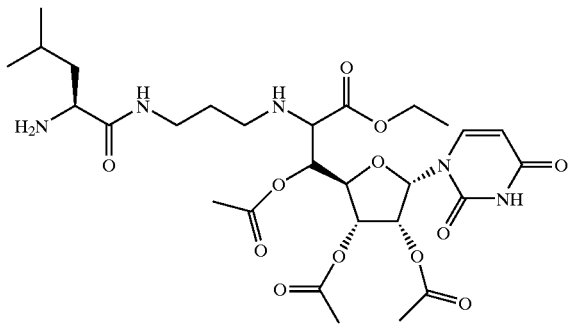

Ethyl (5S)-12-[(R)-(acetyloxy)[(2R,3R,4R,5S)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-1-oate (88 mg, 0.114 mmole, obtained from Example 38) was hydrogenated using 10% palladium on carbon in methanol (2 ml) under atmospheric pressure to provide ethyl (3R)-3-(acetyloxy)-2-[(3-{[(2S)-2-amino-4-methylpentanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]propanoate (76 mg, 95%) as a white glassy solid.

MS (ES): m/z 642.3 (M+H), 321.9 (M+2H)$^{2+}$.

IR cm$^{-1}$: 3328, 1749, 1697, 1238.

Example 40

Ethyl (3R)-3-(acetyloxy)-2-[(3-{[(2S)-2-amino-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]propanoate

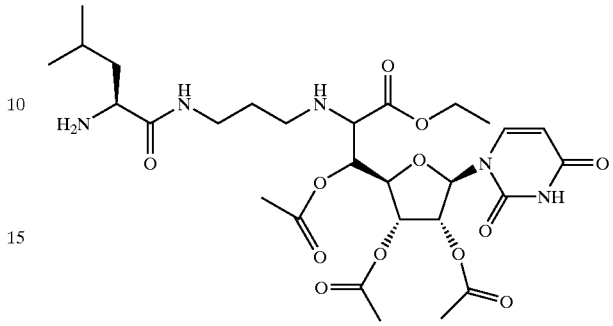

Ethyl (5S)-12-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate (97 mg, 0.125 mmole, obtained from Example 38) was hydrogenated using 10% palladium on carbon in methanol (2 ml) under atmospheric pressure. The catalyst was removed and the volatiles were removed in vacuo to provide ethyl (3R)-3-(acetyloxy)-2-[(3-{[(2S)-2-amino-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]propanoate (76 mg, 95%) as a white glassy solid.

MS (ES): m/z 642.3 (M+H).

IR cm$^{-1}$: 3359, 1746, 1695, 1241.

Example 41

19-Benzyl 5-ethyl (4R,12S,15S,19S)-4-[(2R,3R,4R,5S)-3,4-bis(acetyloxy)-5-(2,4-dioxo-3,4-dihydro-1(2H)-pyrimidinyl)tetrahydro-2-furanyl]-15-(3-{[(2,2-dioxido-2lambda~1~-diazanyl)(imino)methyl]amino}propyl)-12-isobutyl-20-methyl-2,11,14,17-tetraoxo-3-oxa-6,10,13,16,18-pentaazahenicosane-5,19-dicarboxylate

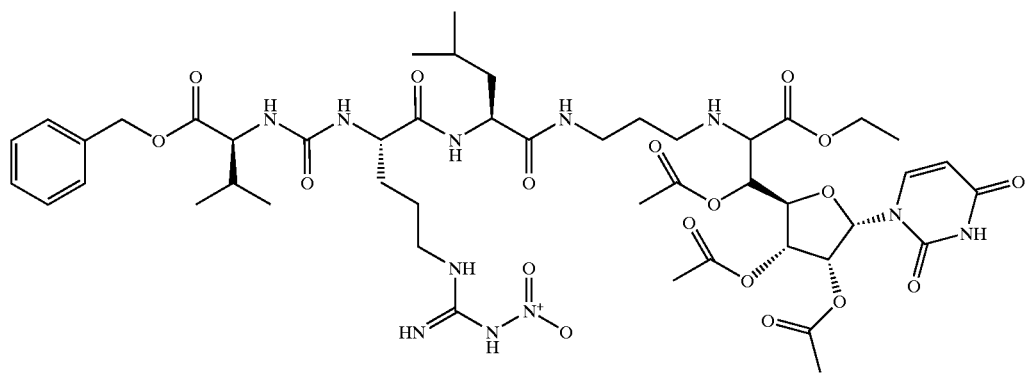

To a solution of (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoic acid (44 mg, 0.0966 mmole, obtained from Reference Example 34) in anhydrous tetrahydrofuran (0.5 ml) was added hydroxybenzotriazole (13 mg, 0.0966 mmole) and 1-(3-dimethylaminopropyl)-3-ethylcarbodiimide hydrochloride (19 mg, 0.0966 mmole). The resulting solution was stirred at room temperature under a nitrogen atmosphere for 30 minutes. A solution of ethyl (3R)-3-(acetyloxy)-2-[(3-{[(2S)-2-amino-4-methylpentanoyl]amino}propyl)amino]-3-[(2R,3R,4R,5S)-

3,4-bis(acetyloxy)-5-(2,4-dioxo-3,4-dihydro-1(2H)-pyrimidinyl)tetrahydro-2-furanyl]propanoate (59 mg, 0.092 mmole, obtained from Example 39) in tetrahydrofuran (1 ml) and N,N-diisopropylethylamine (17 µl, 12 mg, 0.0966 mmole) were added and stirred at room temperature for 16 hours. The reaction mixture was partitioned between ethyl acetate (40 ml) and water (10 ml). The aqueous layer was separated and extracted with ethyl acetate (2×40 ml), the extracts were washed with aqueous sodium bicarbonate solution and saturated sodium chloride solution, dried over sodium sulfate, filtered and concentrated in vacuo. The residue was chromatographed (flash column, silica gel, 5% methanol in methylene chloride) to provide 19-benzyl 5-ethyl (4R,12S,15S,19S)-4-[(2R,3R,4R,5S)-3,4-bis(acetyloxy)-5-(2,4-dioxo-3,4-dihydro-1(2H)-pyrimidinyl)tetrahydro-2-furanyl]-15-(3-{[(2,2-dioxido-2lambda~1~-diazanyl)(imino) methyl]amino}propyl)-12-isobutyl-20-methyl-2,11,14,17-tetraoxo-3-oxa-6,10,13,16,18-pentaazahenicosane-5,19-dicarboxylate (24 mg, 24%) as a white solid.

MS (ES): m/z 1076.3 (M+H), 538.9 (M+2H)$^{2+}$.

Example 42

1-Benzyl 17-ethyl (2S,6S,9S)-16-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate 40) in tetrahydrofuran (1.5 ml) and N,N-diisopropylethylamine (17 □l, 0.127 mmole) were added and stirred at room temperature for 48 hours. The reaction mixture was partitioned between methylene chloride and water. The aqueous layer was separated and extracted with methylene chloride, the extracts were washed with aqueous sodium bicarbonate solution and saturated sodium chloride solution, dried over sodium sulfate, filtered and concentrated in vacuo. The residue was chromatographed (flash column, silica gel, 10% methanol in methylene chloride) to provide 1-benzyl 17-ethyl (2S,6S,9S)-16-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate (54 mg, 44%) as a colorless glass. The product was further purified by preparative HPLC (250×21 mm Phenomenex Prodigy ODS3 column eluted with 10 to 90% acetonitrile in water containing 0.02% trifluoroacetic acid over 100 minutes).

MS (ES): m/z 1076.4 (M+H), 538.8 (M+2H)$^{2+}$.

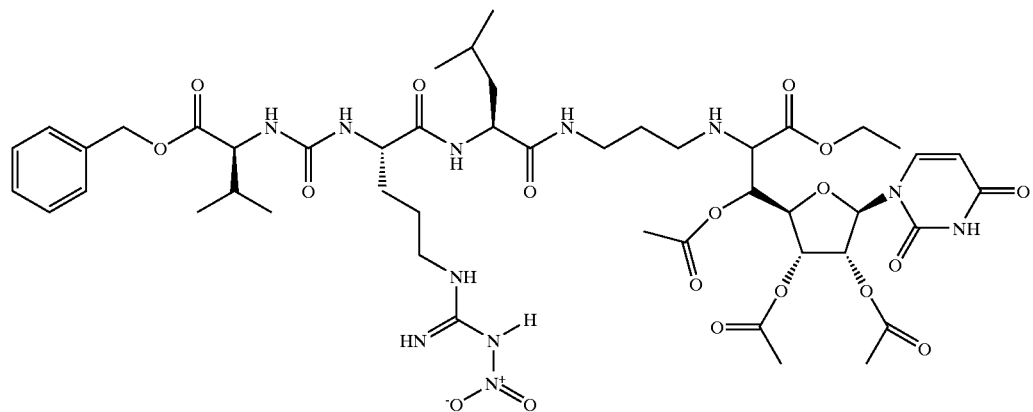

To a solution of (2S)-2-{[({(1S)-1-[(benzyloxy)carbonyl]-2-methylpropyl}amino)carbonyl]amino}-5-{[(2,2-dioxido-2lambda~1~-diazanyl)(imino)methyl]amino}pentanoic acid (55 mg, 0.121 mmole, obtained from Reference Example 34) in anhydrous tetrahydrofuran (0.5 ml) was added hydroxybenzotriazole (16 mg, 0.127 mmole) and 1-(3-dimethylaminopropyl)-3-ethylcarbodiimide hydrochloride (23 mg, 0.127 mmole). The resulting solution was stirred at room temperature under a nitrogen atmosphere for 30 minutes. A solution of ethyl (3R)-3-(acetyloxy)-2-[(3-{[(2S)-2-amino-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]propanoate (74 mg, 0.115 mmole, obtained from Example

Example 43

(2S,6S,9S)-6-(3-{[Amino(imino)methyl]amino}propyl)-16-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-4,7,10,17-tetraoxo-18-oxa-3,5,8,11,15-pentaazaicosan-1-oic acid

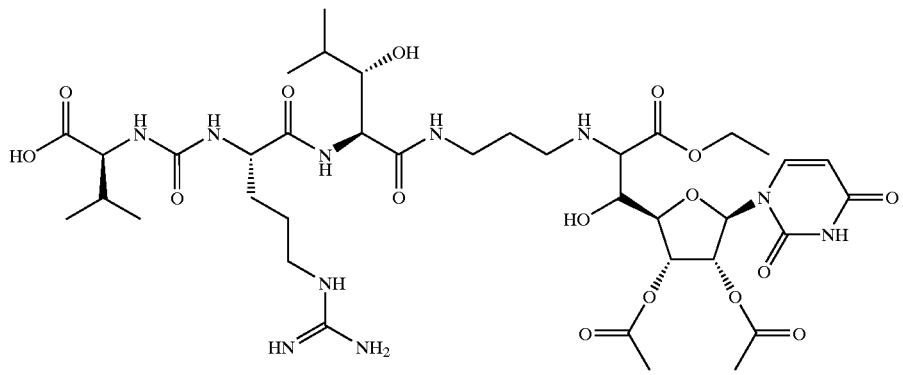

16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-hydroxy-2-methylpropyl]-17-methyl-8,11,14-trioxo-3,7,10,13,15-pentaazaoctadecane-2,16-dicarboxylate (10 mg, 0.0095 mmole, obtained from Example 37) was hydrogenated using 10% palladium on carbon in methanol (3 ml) under atmospheric pressure to give (2S,6S,9S)-6-(3-{[amino(imino)methyl]amino}propyl)-16-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-4,7,10,17-tetraoxo-18-oxa-3,5,8,11,15-pentaazaicosan-1-oic acid (7 mg, 81%) as a white solid.

MS (ES): m/z 458.4 (M+2H)$^{2+}$.

Analytical HPLC (4.6×150 mm Phenomenex ODS3 column eluted with a linear gradient of 10–90% acetonitrile in water containing 0.02% trifluoroacetic acid over 23 minutes): 100% at 7.46 minutes.

Example 44 tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate

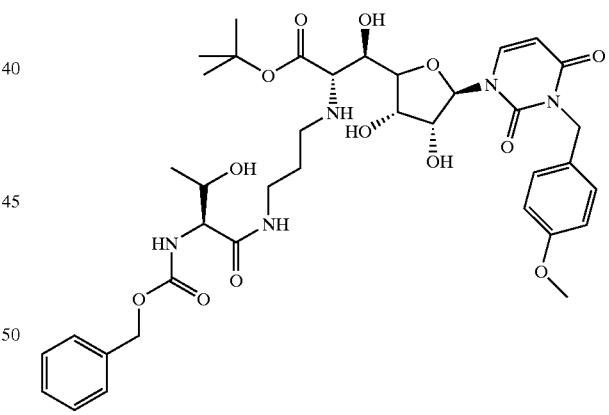

A solution of tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)

tetrahydro-2-furanyl](hydroxy)methyl]-5-[(1S)-1-hydroxyethyl]-3,6-dioxo-1-phenyl-2-oxa-4,7,11-triazatridecan-13-oate (63 mg, 0.062 mmol, obtained from Example 10) in anhydrous tetrahydrofuran (1 ml) was cooled at 0° C. under nitrogen. Tetrabutylammonium fluoride (0.186 mL, 0.186 mmol; 1 M solution in tetrahydrofuran, Aldrich) was added and the resulting mixture was warmed to room temperature and stirred for 2.75 hours. The reaction mixture was diluted with ethyl acetate, washed with saturated sodium chloride, dried over sodium sulfate, filtered and concentrated in vacuo. The residue was chromatographed (flash column, silica gel, 5% methanol in methylene chloride) to provide tert-butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-(hydroxy)methyl]-5-[(1S)-1-hydroxyethyl]-3,6-dioxo-1-phenyl-2-oxa-4,7,11-triazatridecan-13-oate (12 mg, 25%) as a light yellow solid.

MS (ES): m/z 786.3 (M+H).

[(1S)-1-hydroxyethyl]-3,6-dioxo-1-phenyl-2-oxa-4,7,11-triazatridecan-13-oate (8 mg, 0.01 mmol, obtained from Example 44) was hydrogenated in methanol (2 ml) using 10% palladium on carbon (5 mg) under atmospheric pressure for 4 hours. The catalyst was removed and the volatiles was concentrated in vacuo to provide tert-butyl (2S,3R)-2-[(3-{[(2S,3S)-2-amino-3-hydroxybutanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)-tetrahydro-2-furanyl]-3-hydroxypropanoate (6 mg, 92%) as a yellow solid.

MS (ES): m/z 652.1 (M+H), 326.7 (M+2H)$^{2+}$.

Example 46

(5S,12S)-12-[(R)-[(3R,4R,5R)-4-{[tert-butyl(dimethyl)silyl]oxy}-3-hydroxy-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oic acid

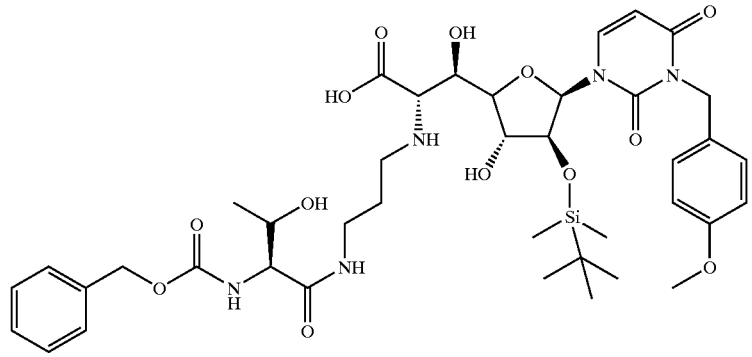

Example 45 tert-Butyl (2S,3R)-2-[(3-{[(2S,3S)-2-amino-3-hydroxybutanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)-tetrahydro-2-furanyl]-3-hydroxypropanoate

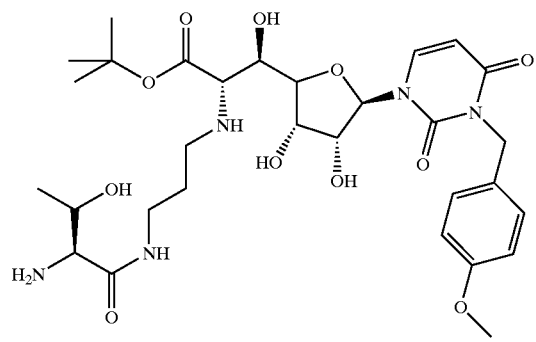

tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-(hydroxy)methyl]-5-

A solution of trifluoroacetic acid (0.3 drops) in methylene chloride (1 ml) was cooled to 0° C. tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate (20 mg, 0.02 mmol, obtained from Example 10) was added and the resulting mixture was stirred at 0° C. for 20 minutes. Additional trifluoroacetic acid (0.9 ml) was gradually added over 1 hour after which the mixture was warmed to room temperature and stirred for 2 hours. The volatiles were removed in vacuo. The residue was azeotroped with toluene, and was then dissolved in methylene chloride (0.5 ml). Cold trifluoroacetic acid (0.5 ml) and the mixture was stirred for 3 hours. The volatiles were removed in vacuo and the residue was azeotroped with toluene to provide (5S,12S)-12-[(R)-[(3R,4R,5R)-4-{[tert-butyl(dimethyl)silyl]oxy}-3-hydroxy-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oic acid (16 mg, 95%) as a yellow solid.

MS (ES): m/z 844.1 (M+H).

IR cm$^{-1}$: 3388, 1790, 1667.

Example 47

(4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)(imino)methyl]amino}propyl)-11-[(1S)-1-hydroxyethyl]-4-isopropyl-3,6,9,12-tetraoxo-1-phenyl-2-oxa-5,7,10,13,17-pentaazanonadecan-19-oic acid

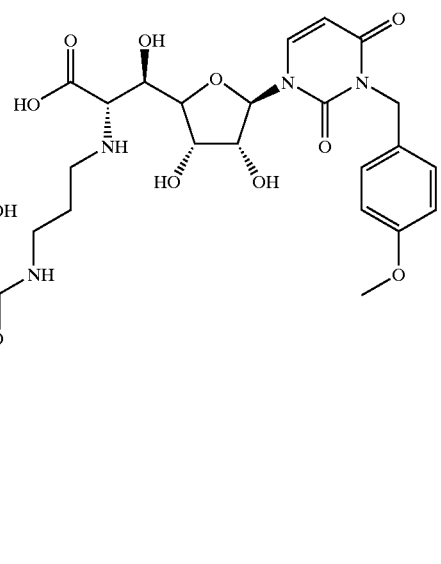

1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-[(1S)-1-hydroxyethyl]-2-isopropyl-4,7,10-trioxo-3,5,8,11,15-pentaazaheptadecane-1,17-dioate (10 mg, 0.0076 mmol, obtained from Example 30) was cooled to 0° C. Water (1 drop) and trifluoroacetic acid (10 drops) were added and the resulting solution stirred at 0° C. for 1 hour, at which point additional water (1 drop) and trifluoroacetic acid (10 drops) were added. Stirring was continued at 0° C. for 1 hour, and then at room temperature for 2.5 hours. The volatiles were removed in vacuo, and methylene chloride (0.5 ml) and trifluoroacetic acid (0.5 ml) were added. The solution was stirred at room temperature for 3 hours, the volatiles were removed and the resultant residue was azeotroped with toluene to provide (4S,8S,11S,18S)-18-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)-(imino)methyl]amino}propyl)-11-[(1S)-1-hydroxyethyl]-4-isopropyl-3,6,9,12-tetraoxo-1-phenyl-2-oxa-5,7,10,13,17-pentaazanonadecan-19-oic acid (6 mg, 76%) as a white solid.

MS (ES): m/z 1030.5 (M+H).

IR cm$^{-1}$: 3383, 1661.

Analytical HPLC (4.6×150 mm Phenomenex ODS3 column eluted with a linear gradient of 10–90% acetonitrile in water containing 0.02% trifluoroacetic acid over 16 minutes): 72% at 8.29 minutes.

Example 48

(2S,3R)-2-[(3-{[(2S,3S)-2-Amino-3-hydroxybutanoyl]amino}propyl)amino]-3-{(3R,4R,5R)-4-{[tert-butyl(dimethyl)silyl]oxy}-5-[3-(4-methoxybenzyl)-2,4-dioxo-3,4-dihydropyrimidin-1(2H)-yl]tetrahydrofuran-2-yl}-3-hydroxypropanoic acid

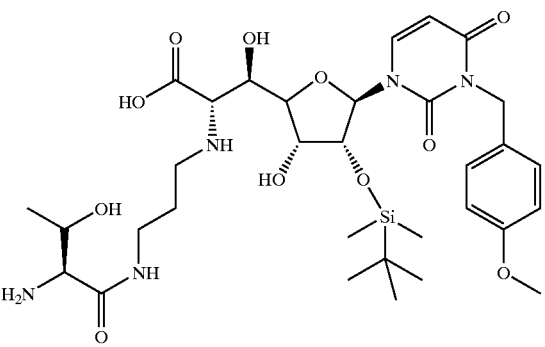

By using an analogous procedure to that described for Example 45, (5S,12S)-12-[(R)-[(3R,4R,5R)-4-{[tert-butyl(dimethyl)silyl]oxy}-3-hydroxy-5-(3-(4-methoxy-benzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oic acid (10.5 mg, 0.012 mmol, obtained from Example 46) was hydrogenated in methanol (1 ml) using 10% palladium on carbon (5 mg) to provide (2S,3R)-2-[(3-{[(2S,3S)-2-amino- 3-hydroxybutanoyl]amino}propyl)amino]-3-{(3R,4R,5R)-4-{[tert-butyl(dimethyl)-silyl]oxy}-5-[3-(4-methoxybenzyl)-2,4-dioxo-3,4-dihydropyrimidin-1(2H)-yl]tetrahydrofuran-2-yl}-3-hydroxypropanoic acid (7.5 mg, 88%) as a gray solid.

MS (ES): m/z 710.3 (M+H).

Example 49

(4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)(imino)methyl]amino}propyl)-11-isobutyl-4-isopropyl-3,6,9,12-tetraoxo-1-phenyl-2-oxa-5,7,10,13,17-pentaazanonadecan-19-oic acid

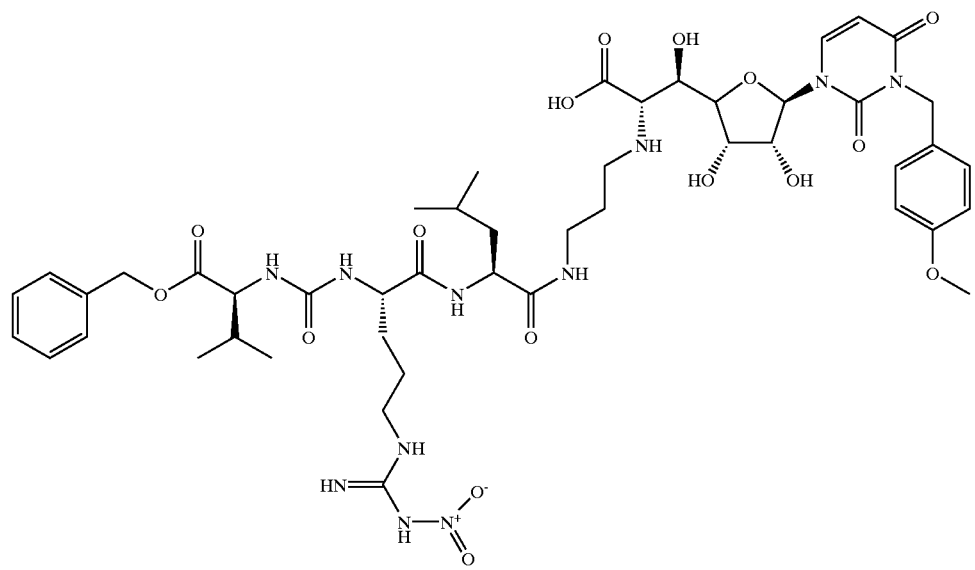

By using an analogous procedure to that described for Example 47, 1-benzyl 17-(tert-butyl) (2S,6S,9S,16)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate (30 mg, 0.023 mmol, obtained from Example 28) in methylene chloride (1 ml), trifluoroacetic acid (1 ml) and water (0.5 ml) were stirred for 3 days. The volatiles were removed and the resultant residue was azeotroped with toluene to provide (4S,8S,11S,8S)-8-[(R)-[(3S,4R,5R)-3,4-dihydroxy-5-(3-(4-methoxybenzyl)-2,4-dioxo-3,4-dihydro-1(2H)-pyrimidinyl)-tetrahydro-2-furanyl](hydroxy)methyl]-8-(3-{[(2,2-dioxido-2lambda~1~-diazanyl)(imino)methyl]amino}-propyl)-11-isobutyl-4-isopropyl-3,6,9,12-tetraoxo-1-phenyl-2-oxa-5,7,10,13,17-pentaazanonadecan-19-oic acid (29 mg, 100%) as a tan solid.

MS (ES): m/z 1042.3 (M+H), 521.8 (M+2H)$^{2+}$.

Example 50

(2S,6S,9S,16S)-6-(3-{[Amino(imino)methyl]amino}propyl)-16-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-4,7,10-trioxo-3,5,8,11,15-pentaazaheptadecane-1,17-dioic acid

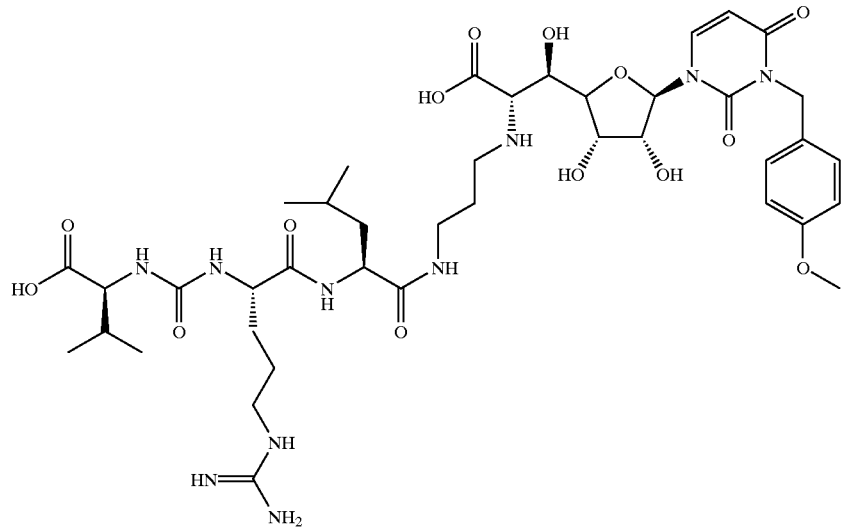

By using an analogous procedure to that described for Example 45, (4S,8S,11S,18S)-18-[(R)-[(3S,4R,5R)-3,4-dihydroxy-5-(3-(4-methoxybenzyl)-2,4-dioxo-3,4-dihydro-1(2H)-pyrimidinyl)-tetrahydro-2-furanyl](hydroxy)methyl]-8-(3-{[(2,2-dioxido-2lambda~1~-diazanyl)(imino)methyl]amino}-propyl)-11-isobutyl-4-isopropyl-3,6,9,12-tetraoxo-1-phenyl-2-oxa-5,7,10,13,17-pentaazanonadecan-19-oic acid (21 mg, 0.02 mmol, obtained from Example 49) was hydrogenated in methanol (1.5 ml) containing acetic acid (0.1 drop) using 10% palladium on carbon (13 mg) overnight to provide (2S,6S,9S,16S)-6-(3-{[amino(imino)methyl]amino}propyl)-16-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)-methyl]-9-isobutyl-2-isopropyl-4,7,10-trioxo-3,5,8,11,15-pentaazaheptadecane-1,17-dioic acid (16.5 mg, 91%) as a light tan solid.

MS (ES): m/z 454.4 (M+2H)$^{2+}$, 907.4 (M+H).

Analytical HPLC (4.6×150 mm Phenomenex ODS3 column eluted with a linear gradient of 17–90% acetonitrile in water containing 0.02% trifluoroacetic acid over 25 minutes): 57.74% at 8.0 minutes.

Example 51 tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate

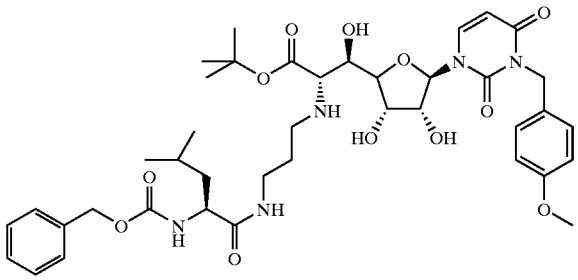

By using an analogous procedure to that described for Example 44, tert-butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (100 mg, 0.097 mmol, obtained from Example 4) and tetrabutylammonium fluoride 0.292 ml, 0.292 mmol) were stirred in tetrahydrofuran (1 ml) under nitrogen for 2.5 hours at room temperature. The residue was chromatographed (flash column, silica gel, 6.5% methanol in methylene chloride) to provide tert-butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (55 mg, 71%) as a white solid.

MS (ES): m/z 798.0 (M+H).

¹H NMR (δ, CDCl₃): 7.836 (d, J=8.04 Hz, 2H), 7.345–7.305 (m, 5H), 7.247 (d, J=8.67 Hz, 2H), 6.859 (d, J=8.73 Hz, 2H), 5.824 (d, J=6.15 Hz, 1H), 5.781 (d, J=8.07 Hz, 1H), 5.541 (d, J=6.33 Hz, 1H), 5.301 (d, J=5.94 Hz, 1H), 5.311–5.291 (m, 1H), 5.123–5.107 (m, 1H), 5.017–5.008 (m, 2H), 4.907 (m, 2H), 4.110–4.056 (m, 2H), 4.007–3.950 (m, 2H), 3.714–3.670 (bs, 4H), 3.139–2.996 (m, 3H), 2.361 (m, 1H), 2.052 (m, 1H), 1.623–1.361 (m, 6H), 1.415 (s, 9H), 0.970–0.827 (m, 6H).

Analytical HPLC (4.6×150 mm Phenomenex ODS3 column eluted with a linear gradient of 20–90% acetonitrile in water containing 0.02% trifluoroacetic acid over 25 minutes): 94.27% at 11.5 minutes.

Example 52

(5S,12S)-12-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oic acid

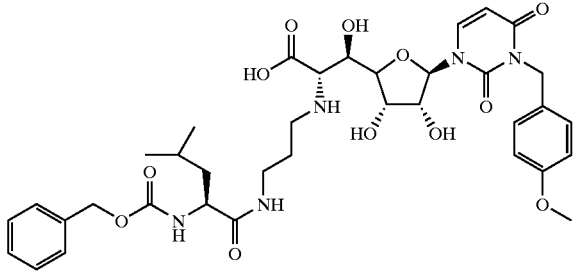

A solution of tert-butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (51 mg, 0.064 mmol, obtained from Example 51) in trifluoroacetic acid (6 ml) was stirred 5 hours at room temperature. The volatiles were removed in vacuo and the resulting residue was azeotroped with toluene to provide (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oic acid (45 mg, 95%) as a light tan solid.

MS (ES): m/z 742.2 (M+H).

¹H NMR (δ, CDCl₃): 8.890 (bs, 1H), 8.112–8.093 (m, 1H), 7.706 (d, J=8.1 Hz, 1H), 7.421–7.334 (m, 5H), 7.278–7.235 (m, 2H), 6.857 (d, J=8.7 Hz, 2H), 6.210 (bs, 1H), 5.873–5.817 (m, 2H), 5.328 (m, 1H), 5.028–4.944 (m, 2H), 4.924–4.858 (m, 2H), 4.272–4.255 (m, 1H), 4.158–4.098 (m, 2H), 4.011–3.925 (m, 4H), 3.710 (s, 3H), 3.111–3.092 (m, 2H), 2.926 (m, 2H), 1.772 (m, 2H), 1.593–1.505 (m, 2H), 1.460–1.358 (m, 2H), 0.905–0.827 (m, 6H).

Analytical HPLC (4.6×150 mm Phenomenex ODS3 column eluted with a linear gradient of 20–90% acetonitrile in water containing 0.02% trifluoroacetic acid over 25 minutes): 77.85% at 9.9 minutes.

Example 53

(2S,3R)-2-[(3-{[(2S)-2-Amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoic acid

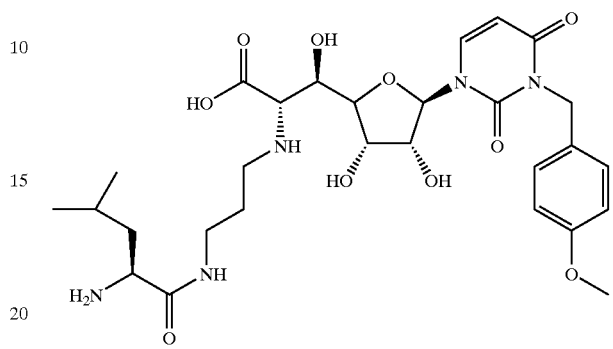

By using an analogous procedure to that described for Example 45, (5S,12S)-12-pyrimidinyl)tetrahydro-2-furanyl]-(hydroxy)methyl}-5-isobutyl-3,6-dioxo-1-phenyl-2-oxa-4,7,11-triazatridecan-13-oic acid (20 mg, 0.027 mmol, obtained from Example 52) was hydrogenated in methanol (2.5 ml) using 10% palladium on carbon (8 mg) for 2 hours to provide (2S,3R)-2-[(3-{[(2S)-2-amino-4-methylpentanoyl]-3,4-dihydro-1(2H)-pyrimidinyl)tetrahydro-2-furanyl]-3-hydroxypropanoic acid (16 mg, 97%) as a white solid.

MS (ES): m/z 608.2 (M+H).

Analytical HPLC (4.6×150 mm Phenomenex ODS3 column eluted with a linear gradient of 10–90% acetonitrile in water containing 0.02% trifluoroacetic acid over 25 minutes): 89.07% at 7.04 minutes.

Example 54 tert-Butyl (2S,3R)-2-[(3-{[(2S)-2-amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoate

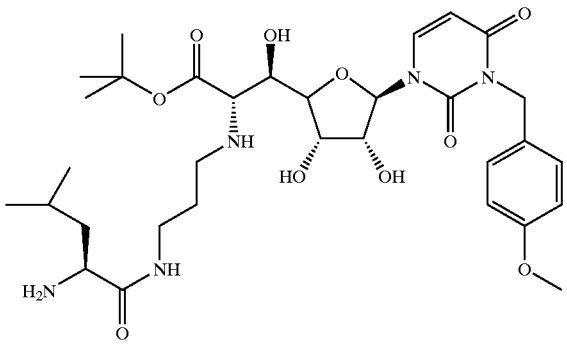

By using an analogous procedure to that described for Example 45, tert-butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (20 mg, 0.025 mmol, obtained from Example 51)

was hydrogenated in methanol (1 ml) using 10% palladium on carbon (8 mg) for 4 hours to provide tert-butyl (2S,3R)-2-[(3-{[(2S)-2-amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoate (15 mg, 90%) as a white solid.

MS (ES): m/z 664.2 (M+H).

$^1$H NMR (δ, CDCl$_3$): 7.625 (m, 1H), 7.508 (d, J=8.1 Hz, 1H), 7.432 (d, J=8.61 Hz, 1H), 7.342 (d, J=11.34 Hz, 1H), 6.818 (d, J=8.58 Hz, 2H), 5.761 (d, J=8.04 Hz, 1H), 5.594 (d, J=3.36 Hz, 1H), 5.079–4.972 (m, 2H), 4.448–4.432 (m, 1H), 4.380–4.368 (m, 1H), 4.202–4.184 (m, 2H), 3.910 (m, 1H), 3.776 (s, 3H), 3.655–3.478 (m, 3H), 3.396–3.375 (m, 2H), 3.221–3.176 (m, 1H), 2.799–2.732 (m, 1H), 2.506 (m, 1H), 1.483 (s, 9H), 1.394–1.260 (m, 8H), 0.972–0.866 (m, 6H).

Analytical HPLC (4.6×150 mm Phenomenex ODS3 column eluted with a linear gradient of 5–90% acetonitrile in 10 mM phosphate buffer pH 3.0 over 25 minutes): 73.42% at 9.3 minutes.

Example 55

(5S,12S)-12-[(R)-[(3S,4R,5R)-5-(2,4-Dioxo-3,4-dihydro-1(2H)-pyrimidinyl)-3,4-dihydroxy-tetrahydro-2-furanyl](hydroxy)methyl]-5-isobutyl-3,6-dioxo-1-phenyl-2-oxa-4,7,11-triazatridecan-13-oic acid

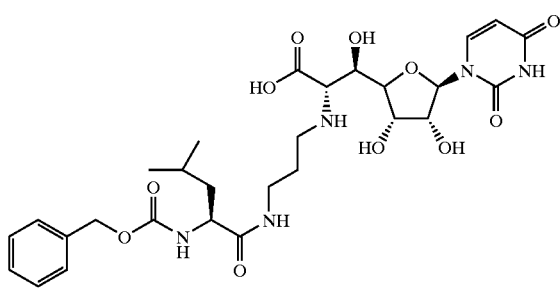

By using an analogous procedure to that described for Example 47, tert-butyl (5S,12S)-12-[(R)-[(3R,4R,5R)-3,4-bis[tert-butyl(dimethyl)silyl]oxy}-5-(2,4-dioxo-3,4-dihydro-1(2H)-pyrimidinyl)-tetrahydro-2-furanyl] (hydroxy)methyl]-5-isobutyl-3,6-dioxo-1-phenyl-2-oxa-4,7,11-triazatridecan-13-oate (123 mg, 0.136 mmol, obtained from Example 6), trifluoroacetic acid (5 ml) and water (6 drops) were stirred for 10 hours at room temperature. The volatiles were removed and the residue was azeotroped with toluene. The resulting residue was purified by preparative HPLC (20×250 mm YMC-ODS column eluted with 10–70% acetonitrile in water containing 0.02% trifluoroacetic acid over 49 minutes) to provide (5S,12S)-12-[(R)-[(3S,4R,5R)-5-(2,4-dioxo-3,4-dihydro-1(2H)-pyrimidinyl)-3,4-dihydroxy-tetrahydro-2-furanyl](hydroxy)methyl]-5-isobutyl-3,6-dioxo-1-phenyl-2-oxa-4,7,11-triazatridecan-13-oic acid (13 mg, 15%) as a white solid.

MS (ES): m/z 622.0 (M+H).

Analytical HPLC (4.6×150 mm Phenomenex ODS3 column eluted with a linear gradient of 5–90% acetonitrile in water containing 0.02% trifluoroacetic acid over 16 minutes): 98.2% at 11.8 minutes.

Example 56 tert-Butyl (5R,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate

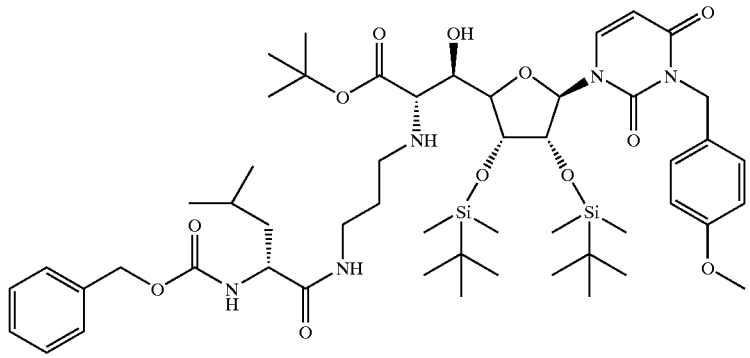

A solution of tert-butyl (5S,12S)-12-[(R)-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (62 mg, 0.086 mmol, obtained from Reference Example 6) and [(1R)-3-methyl-1-(3-oxo-propylcarbamoyl)butyl]-carbamic acid benzyl ester (33 mg, 0.103 mmol, obtained from N-CBZ-D-leucine in an similar manner described in Reference Example 15 and 16) in anhydrous tetrahydrofuran was stirred at room temperature under a nitrogen atmosphere for 15 minutes. Acetic acid (2 drops) and sodium triacetoxyborohydride (36 mg, 0.17 mmol) were added and the resulting solution was stirred under nitrogen for an additional 2.5 hours. The reaction mixture was basified to pH 9 with aqueous sodium carbonate solution and the aqueous layer was extracted with ethyl acetate (3×50 ml). The combined extracts were washed with saturated sodium chloride solution, dried over sodium sulfate, filtered and concentrated in vacuo. The residue was chromatographed (flash column, silica gel, 2.5% methanol in methylene chloride) to provide tert-butyl (5R,12S)-12-[(R)-[(3R,4R,5R)-3,4-bis{[tert-butyl(dimethyl)silyl]oxy}-

5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (37 mg, 42%) as a white amorphous solid.

MS (ES): m/z 1026.3 (M+H).

Analytical HPLC (4.6×150 mm LUNA C5 column eluted with an isocratic gradient of 20–80% acetonitrile in 10 mM ammonium acetate pH 4.1 over 23 minutes): 77.52% at 15.1 minutes.

Example 57 tert-Butyl (2S,3R)-2-[(3-{[(2R)-2-amino-4-methylpentanoyl]amino}propyl)amino]-3-[(3R,4R,5R)-3,4-bis{[tert-butyl(dimethyl)silyl]oxy-5-(3-(4-methoxybenzyl)-2,4-dioxo-3,4-dihydro-1(2H)-pyrimidinyl)tetrahydro-2-furanyl]-3-hydroxypropanoate

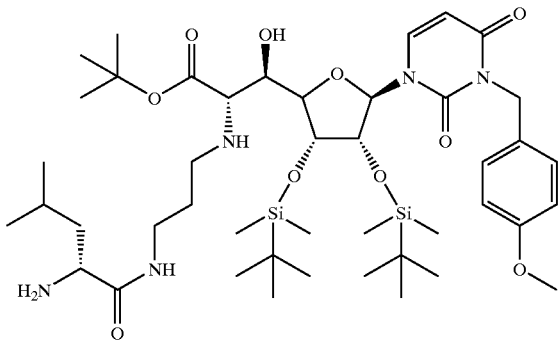

By using an analogous procedure to that described for Example 45, tert-butyl (5R,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate (21 mg, 0.02 mmol, obtained from Example 56) was hydrogenated in methanol (2 ml) using 10% palladium on carbon (10 mg) for 3.5 hours to provide tert-butyl (2S,3R)-2-[(3-{[(2R)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate (14 mg, 78%) as a white solid.

MS (ES): m/z 446.8 (M+2H)$^{2+}$, 892.2 (M+H).

Analytical HPLC (4.6×150 mm LUNA C5 column eluted with an isocratic gradient

Example 58

Ethyl (5S)-12-[(R)-[(2R,3R,4R,5R)-3,4-bis(acetyloxy)-5-(2,4-dioxo-3,4-dihydropyrimidin-1(2h)-yl)tetrahydrofuran-2-yl](hydroxy)methyl]-3,6-dioxo-1-phenyl-5-[(1S)-1-(tetradecanoyloxy)ethyl]-2-oxa-4,7,11-triazatridecan-13-oate

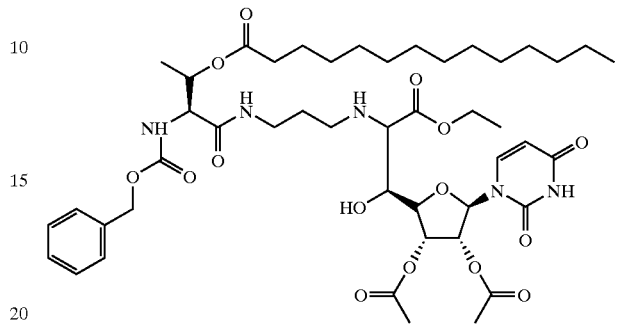

By using an analogous procedure to that described for Example 56, a solution of (1S,2S)-2-1[(benzyloxy)carbonyl]amino}-1-methyl-3-oxo-3-[(3-oxopropyl)amino]propyl myristate (250 mg, 0.483 mmol, obtained from Reference Example 48) and the hydrogen chloride salt mixture of ethyl (2R,3R)-3-(acetyloxy)-2-dihydro-1(2H)-pyrimidinyl)tetrahydro-2-furanyl]propanoate and ethyl (2R,3R)-3-(acetyloxy)-2-{[(benzyloxy)carbonyl]amino}-3-[(2R,3R,4R,5S)-3,4-bis(acetyloxy)-5-(2,4-dioxo-3,4-dihydro-1(2H)-pyrimidinyl)tetrahydro-2-furanyl]propanoate (207 mg, 0.483 mmol, obtained from Reference Example 46), acetic acid (0.028 ml, 0.483 mmol) and sodium triacetoxyborohydride (205 mg, 0.97 mmol) in anhydrous tetrahydrofuran (4 ml) was stirred at room temperature under a nitrogen atmosphere for 16 hours. The product was chromatographed (flash column, silica gel, 75% ethyl acetate in hexane) to provide ethyl (5S)-12-[(R)-[(2R,3R,4R,5R)-3,4-bis(acetyloxy)-5-(2,4-dioxo-3,4-dihydropyrimidin-1(2 h)-yl)tetrahydrofuran-2-yl](hydroxy)methyl]-3,6-dioxo-1-phenyl-5-[(1S)-1-(tetradecanoyloxy)ethyl]-2-oxa-4,7,11-triazatridecan-13-oate (100 mg, 22%) as a white amorphous solid.

MS (ES): m/z 932.2 (M+H).
IR cm$^{-1}$: 3338, 2925, 2854, 1735, 1698.

What is claimed:
1. A compound of the formula

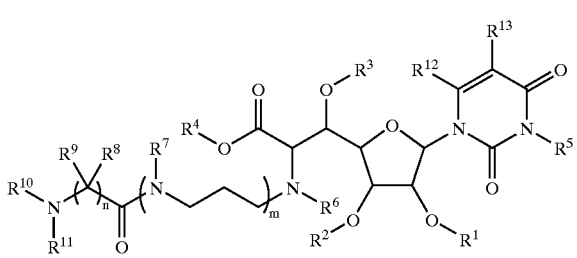

Formula 1 wherein:
m is an integer of 0 to 2;
n is an integer of 0 to 13;
p is an integer of 0 to 2;
q is an integer of 0 to 5;
J is F, Cl or Br;

$R^1$, $R^2$, $R^3$, and $R^4$ are independently

H;

alkyl of 1 to 10 carbon atoms optionally substituted with 1 to 3 substituents selected from the group consisting of -J, $-R^{16}$, -aryl, $-OR^{14}$, $-OR^{16}$, $-OR^{15}R^{16}$, $-Oaryl$, $-OR^{15}OR^{14}$, $-OCH_2OR^{16}$, $-OR^{15}OR^{15}aryl$, $-OR^{15}Oaryl$, $-C(O)OR^{14}$, $-C(O)OR^{16}$, $-C(O)OR^{15}R^{16}$, $C(O)R^{14}$, $-C(O)R^{16}$, $-C(O)R^{15}R^{16}$, $-C(O)aryl$, $-C(O)R^{15}aryl$, silyl substituted with three groups independently selected from $R^{14}$, $R^{15}$, and $R^{16}$, $-O$-silyl substituted with three groups independently selected from $R^{14}$, $R^{15}$, and $R^{16}$;

cycloalkyl of 3 to 10 carbon atoms optionally substituted with one to three alkyl groups of 1 to 6 carbon atoms;

silyl substituted with three groups independently selected from $R^{14}$, $R^{15}$, and $R^{16}$;

$-C(O)R^{14}$, $-C(O)R^{15}R^{16}$, $-C(O)R^{16}$, $-C(O)aryl$, $-C(O)R^{15}aryl$;

allyl optionally substituted with one to three moieties independently selected from $R^{14}$, $R^{15}$, and $R^{16}$;

$R^{15}aryl$;

aryl;

$R^{14}$ is a monovalent group independently selected from alkyl of 1 to 6 carbon atoms, alkenyl of 2 to 6 carbon atoms, and alkynyl of 2 to 6 carbon atoms;

$R^{15}$ is a divalent alkyl group of 1 to 6 carbon atoms; optionally when two of $R^{15}$ are substituted on a nitrogen atom together with the nitrogen to which they are attached, form a ring selected from morpholine, piperazine or piperidine;

$R^{16}$ is aryl optionally substituted with 1 to 4 substituents selected from the group consisting of: -J, $-NO_2$, $-NH_2$, $-OH$, $-SH$, $-CN$, $-COOH$, $-CONH_2$, $-NHC(O)NH_2$, $-CF_3$, $-OCF_3$, $-R^{14}$, $-OR^{14}$, $-NHR^{14}$, $-NR^{14}R^{14}$, $-S(O)_mR^{14}$, $-NHSO_2R^{14}$, $-R^{15}OH$, $-R^{15}OR^{14}$, $-R^{15}NH_2$, $-R^{15}NHR^{14}$, $-R^{15}NR^{14}R^{14}$, $-R^{15}SH$, $R^{15}S(O)_mR^{14}$, $-NHR^{15}OH$, $-NHR^{15}OR^{14}$, $-N(R^{14})R^{15}OH$, $-N(R^{14})R^{15}OR^{14}$, $-NHR^{15}NH_2$, $-NHR^{15}NHR^{14}$, $-NHR^{15}NR^{14}R^{14}$, $-N(R^{14})R^{15}NH_2$, $-N(R^{14})R^{15}NHR^{14}$, $-N(R^{14})R^{15}NHR^{14}R^{14}$, $-OR^{15}OH$, $-OR^{15}OR^{14}$, $-NHC(O)R^{14}$, $-NHC(O)NHR^{14}$, $-OR^{15}C(O)R^{14}$, $-NHR^{15}C(O)R^{14}$, $-C(O)R^{14}$, $-C(O)R^{14}$, $-C(O)NHR^{14}$, $-C(O)NR^{14}R^{14}$, $-R^{14}C(O)R^{14}$, $-R^{15}C(O)OH$, $-R^{15}C(O)OR^{14}$, $-R^{15}C(O)NH_2$, $-R^{15}C(O)NHR^{14}$, $-R^{15}C(O)NR^{14}R^{14}$, $-R^{15}OC(O)R^{14}$, $-R^{15}OC(O)NH_2$, $-R^{15}OC(O)NHR^{14}$, and $-R^{15}OC(O)NR^{14}R^{14}$;

aryl may optionally be substituted by $-V$-aryl, $-V-R^{16}$ or $-V-R^{17}$;

V is selected from C(O), C(O)O, OC(O), C(O)NH, NHC(O), NHSO$_2$, SO$_2$NH, C(OH)H, O(CR$^{18}$R$^{18}$)$_q$, S(O)$_{m''}$(CR$^{18}$R$^{18}$)$_q$, NH(CR$^{18}$R$^{18}$)$_q$, NR$^{19}$(CR$^{18}$R$^{18}$)$_q$, (CR$^{18}$R$^{18}$)$_q$, (CR$^{18}$R$^{18}$)$_q$O, (CR$^{18}$R$^{18}$)$_q$S(O)$_{m''}$, (CR$^{18}$R$^{18}$)$_q$NH, (CR$^{18}$R$^{18}$)$_q$NR$^{15}$, alkenyl of 2 to 6 carbon atoms, alkynyl of 2 to 6 carbon atoms and cycloalkyl of 3 to 10 carbon atoms;

$R^{17}$ is cycloalkyl of 3 to 7 carbon atoms optionally substituted with one or more alkyl groups of 1 to 6 carbon atoms or $R^{14}$;

$R^{18}$ is independently H or $R^{14}$;

$R^5$, $R^6$, $R^7$ and $R^{10}$ are independently

H;

alkyl of 1 to 10 carbon atoms optionally substituted with 1 to 3 substituents selected from the group consisting of -J, $-R^{16}$, -aryl, $-OR^{14}$, $-OR^{16}$, $-OR^{15}R^{16}$, $-Oaryl$, $-OR^{15}OR^{14}$, $-OCH_2OR^{16}$, $-OR^{15}OR^{15}aryl$, $-OR^{15}Oaryl$, $-C(O)OR^{14}$, $-C(O)OR^{16}$, $-C(O)OR^{15}R^{16}$, $-C(O)Oaryl$, $-C(O)OR^{15}aryl$, $-C(O)R^{14}$, $-C(O)R^{16}$, $-C(O)R^{15}R^{16}$, $-C(O)aryl$, $-C(O)R^{15}aryl$, silyl substituted with three groups independently selected from $R^{14}$, $R^{15}$, and $R^{16}$, $-O$-silyl substituted with three groups independently selected from $R^{14}$, $R^{15}$, and $R^{16}$;

cycloalkyl of 3 to 10 carbon atoms optionally substituted with one to three alkyl groups of 1 to 6 carbon atoms;

$-C(O)R^{14}$, $-C(O)R^{15}R^{16}$, $-C(O)R^{16}$, $-C(O)aryl$, or $-C(O)R^{15}aryl$;

$-C(O)OR^{14}$, $-C(O)OR^{15}R^{16}$, or $-C(O)OR^{16}$;

allyl optionally substituted with one to three groups independently selected from $R^{14}$, $R^{15}$, and $R^{16}$;

$R^{15}aryl$;

aryl;

$R^8$, $R^9$ are independently

H;

alkyl of 1 to 10 carbon atoms optionally substituted with 1 to 3 substituents selected from the group consisting of $-R^{16}$, $-OH$, $-C(O)OH$, $CONH_2$, $-NHC(O)NH_2$, $-OR^{14}$, $-OR^{16}$, $-OR^{15}R^{16}$, $-Oaryl$, $-OR^{15}aryl$, $-OR^{15}OR^{14}$, $-OR^{15}OR^{16}$, $-OR^{15}OR^{15}R^{16}$, $-OR^{15}OR^{15}aryl$, $-OR^{15}Oaryl$, $-C(O)OR^{14}$, $-C(O)OR^{16}$, $-C(O)OR^{15}R^{16}$, $-C(O)Oaryl$, $-C(O)OR^{15}aryl$, $-C(O)R^{14}$, $-C(O)R^{16}$, $-C(O)R^{15}R^{16}$, $-C(O)aryl$, $-C(O)R^{15}aryl$, $-S(O)pR^{14}$, $-S(O)pR^{16}$, $-S(O)pR^{16}R^{16}$, $-S(O)paryl$, $-S(O)pR^{15}aryl$, $C(O)aryl$, $-C(O)R^{15}aryl$, $-S(O)pR^{14}$, $-S(O)pR^{16}$, $-S(O)pR^{15}R^{16}$, $-S(O)paryl$, $-S(O)pR^{15}aryl$, $NHC(=NH)NH_2$, $-NHC(=NH)NH(NO_2)$, $-N$-optionally substituted with three groups independently selected from $R^{14}$, $R^{15}$, and $R^{16}$, silyl substituted with three groups independently selected from $R^{14}$, $R^{15}$, and $R^{16}$, $-O$-silyl substituted with three groups independently selected from $R^{14}$, $R^{15}$, and $R^{16}$;

allyl optionally substituted with one to three groups independently selected from $R^{14}$, $R^{15}$, and $R^{16}$;

aryl;

cycloalkyl group of 3 to 10 carbon atoms, which may be optionally substituted with one or more alkyl groups of 1 to 6 carbon atoms;

$R^{11}$ is independently

H;

alkyl of 1 to 10 carbon atoms optionally substituted with 1 to 3 substituents selected from the group consisting of -J, $-R^{16}$, -aryl, $-OR^{14}$, $-OR^{16}$, $-OR^{15}R^{16}$, $-Oaryl$, $-OR^{15}OR^{14}$, $-OCH_2OR^{16}$, $-OR^{15}OR^{15}aryl$, $-OR^{15}Oaryl$, $-C(O)OR^{14}$, $-C(O)OR^{16}$, $-C(O)OR^{15}R^{16}$, $-C(O)Oaryl$, $-C(O)OR^{15}aryl$, $-C(O)R^{14}$, $-C(O)R^{16}$, $-C(O)R^{15}R^{16}$, $-C(O)aryl$, $-C(O)R^{15}aryl$, $-N$-optionally substituted with three groups independently selected from $R^{14}$, $R^{15}$, and $R^{16}$, -silyl substituted with three groups independently selected from $R^{14}$, $R^{15}$, and $R^{16}$, $-O$-silyl substituted with three groups independently selected from $R^{14}$, $R^{15}$, and $R^{16}$;

$-C(O)(CR^{19}R^{20})NHC(O)NH(CR^{21}R^{22})COOR^{23}$;

cycloalkyl of 3 to 10 carbon atoms optionally substituted with one to three alkyl groups of 1 to 6 carbon atoms;

$-C(O)R^{14}$, $-C(O)R^{15}R^{16}$, $-C(O)R^{16}$, $-C(O)aryl$, $-C(O)R^{15}aryl$;

allyl optionally substituted with one to three groups independently selected from $R^{14}$, $R^{15}$, and $R^{16}$;

$R^{15}$aryl;

aryl;

$R^{19}$, $R^{20}$, $R^{21}$ and $R^{22}$ are independently

H;

alkyl of 1 to 10 carbon atoms optionally substituted with 1 to 3 substituents selected from the group consisting of —$R^{16}$, —OH, —C(O)OH, CONH$_2$, —NHC(O)NH$_2$, —O$R^{14}$, —O$R^{16}$, —O$R^{15}R^{16}$, —Oaryl, —O$R^{15}$aryl, —O$R^{15}$O$R^{14}$, —O$R^{15}$O$R^{16}$, —O$R^{15}$O$R^{15}R^{16}$, —O$R^{15}$O$R^{15}$aryl, —O$R^{15}$Oaryl, —C(O)O$R^{14}$, —C(O)O$R^{16}$, —C(O)O$R^{15}R^{16}$, —C(O)Oaryl, —C(O)O$R^{15}$aryl, —C(O)$R^{14}$, —C(O)$R^{16}$, —C(O)$R^{15}R^{16}$, —C(O)aryl, —C(O)$R^{15}$aryl, —S(O)p$R^{14}$, —S(O)p$R^{16}$, —S(O)p$R^{15}R^{16}$, —S(O)paryl, —S(O)p$R^{15}$aryl, NHC(=NH)NH$_2$, —NHC(=NH)NH(NO$_2$), —N-optionally substituted with three groups independently selected from $R^{14}$, $R^{15}$, and $R^{16}$, silyl substituted with three groups independently selected from $R^{14}$, $R^{15}$, and $R^{16}$, —O-silyl substituted with three groups independently selected from $R^{14}$, $R^{15}$, and $R^{16}$;

allyl optionally substituted with one to three groups independently selected from $R^{14}$, $R^{15}$, and $R^{16}$;

aryl;

cycloalkyl group of 3 to 10 carbon atoms, which may be optionally substituted with one or more alkyl groups of 1 to 6 carbon atoms;

$R^{23}$ is

H;

alkyl of 1 to 10 carbon atoms optionally substituted with 1 to 3 substituents selected from the group consisting of -J, —$R^{16}$, -aryl, —O$R^{14}$, —O$R^{16}$, —O$R^{15}R^{16}$, —Oaryl, —O$R^{15}$O$R^{14}$, —OCH$_2$O$R^{16}$, —O$R^{15}$O$R^{15}$aryl, —O$R^{15}$Oaryl, —C(O)O$R^{14}$, —C(O)O$R^{16}$, —C(O)O$R^{15}R^{16}$, —C(O)Oaryl, —C(O)O$R^{15}$aryl, —C(O)$R^{14}$, —C(O)$R^{16}$, —C(O)$R^{15}R^{16}$, —C(O)aryl, —C(O)$R^{15}$aryl;

silyl substituted with three groups independently selected from $R^{14}$, $R^{15}$, and $R^{16}$;

cycloalkyl of 3 to 10 carbon atoms optionally substituted with one to three alkyl groups of 1 to 6 carbon atoms; —C(O)$R^{14}$, —C(O)$R^{15}R^{16}$, —C(O)$R^{16}$, —C(O)aryl, —C(O)$R^{15}$aryl;

allyl optionally substituted with one to three groups independently selected from $R^{14}$, $R^{15}$, and $R^{16}$;

$R^{15}$aryl;

aryl;

$R^{12}$ and $R^{13}$ are independently

H;

F;

an alkyl group of 1 to 10 carbon atoms including their branches;

allyl optionally substituted with one to three groups independently selected from $R^{14}$, $R^{15}$, and $R^{16}$;

aryl;

or a pharmaceutically acceptable salt thereof.

2. A compound according to claim 1 wherein:

$R^3$, $R^{12}$ and $R^{13}$ are H;

m is an integer of 1 or 2;

$R^1$ and $R^2$ are silyl substituted with three groups independently selected from $R^{14}$, $R^{15}$, and $R^{16}$.

3. A compound according to claim 1 wherein:

$R^3$, $R^6$, $R^7$, $R^{12}$ and $R^{13}$ are H;

m is an integer of 1 or 2;

$R^1$ and $R^2$ are silyl substituted with three groups independently selected from $R^{14}$, $R^{15}$, and $R^{16}$.

4. A compound according to claim 1 wherein:

$R^1$, $R^2$, $R^3$, $R^{12}$ and $R^{13}$ are H;

m is an integer of 1 or 2.

5. A compound according to claim 1 wherein:

$R^1$, $R^2$, $R^3$, $R^6$, $R^7$, $R^{12}$ and $R^{13}$ are H;

m is an integer of 1 or 2.

6. A compound according to claim 1 wherein:

$R^3$, $R^{12}$ and $R^{13}$ are H;

m is an integer of 1 or 2;

$R^1$ and $R^2$ are —C(O)$R^{14}$, —C(O)$R^{15}R^{16}$, —C(O)aryl, —C(O)$R^{15}$aryl.

7. A compound according to claim 1 wherein:

$R^3$, $R^6$, $R^7$, $R^{12}$ and $R^{13}$ are H;

m is an integer of 1 or 2;

$R^1$ and $R^2$ are —C(O)$R^{14}$, —C(O)$R^{15}R^{16}$, —C(O)$R^{16}$, —C(O)aryl, or —C(O)$R^{15}$aryl.

8. A pharmaceutical composition comprising a compound according to claim 1 in association with a pharmaceutically acceptable carrier.

9. A method for the treatment of bacterial infections in warm-blooded animals which comprises providing to said warm-blooded animals an antibacterially effective amount of a compound according to claim 1 or a pharmaceutically acceptable salt thereof.

10. The compound according to claim 1 which is tert-Butyl (2S,3S)-2-[(3-{[(2S,3S)-2-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

11. The compound according to claim 1 which is tert-Butyl (2S,3S)-2-[(3-{[(2S,3S)-2-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

12. The compound according to claim 1 which is tert-Butyl (2S,3R)-2-[(3-{[(2S,3S)-2-amino-3-hydroxy-4-methylpetanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

13. The compound according to claim 1 which is (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-19,19-dimethyl-4,7,10,17-tetraoxo-18-oxa-3,5,8,11,15-pentaazaicosan-1-oic acid or a pharmaceutically acceptable salt thereof.

14. The compound according to claim 1 which is tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

15. The compound according to claim 1 which is (3S)-3-Amino-4-[(3-{[(1S,2S)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-4-oxobutanoic acid or a pharmaceutically acceptable salt thereof.

16. The compound according to claim 1 which is tert-Butyl (2S,3R)-2-[(3-{[(2S)-2-aminopropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

17. The compound according to claim 1 which is (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-19,19-dimethyl-4,7,10,17-tetraoxo-18-oxa-3,5,8,11,15-pentaazaicosan-1-oic acid or a pharmaceutically acceptable salt thereof.

18. The compound according to claim 1 which is tert-Butyl (2S,3R)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-2-[(3-{[(2S)-2,6-diaminohexanoyl]amino}propyl)amino]-3-hydroxypropanoate or a pharmaceutically acceptable salt thereof.

19. The compound according to claim 1 which is tert-Butyl (4S)-4-amino-5-[(3-{[(1S,2R)-2-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-1-(tert-butoxycarbonyl)-2-hydroxyethyl]amino}propyl)amino]-5-oxopentanoate or a pharmaceutically acceptable salt thereof.

20. The compound according to claim 1 which is tert-Butyl (2S,3R)-2-amino-3-[(2R,3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

21. The compound according to claim 1 which is tert-Butyl (5S,12S)-12-[(R)-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate or a pharmaceutically acceptable salt thereof.

22. The compound according to claim 1 which is tert-Butyl (2S,3R)-2-[(3-{[(2S)-2-amino-4-methylpentanoyl]amino}propyl)amino]-3-[(3R,4R,5R)-3,4-bis{[tert-butyl(dimethyl)silyl]oxy}-5-(2,4-dioxo-3,4-dihydro-1(2H)-pyrimidinyl)tetrahydro-2-furanyl]-3-hydroxypropanoate or a pharmaceutically acceptable salt thereof.

23. The compound according to claim 1 which is tert-Butyl (2S,3R)-2-[(11-aminoundecanoyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

24. The compound according to claim 1 which is tert-Butyl (2S,3R)-2-({3-[(11-aminoundecanoyl)amino]propyl}amino)-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

25. The compound according to claim 1 which is (4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~diazanyl)(imino)methyl]amino}propyl)-11-isobutyl-4-isopropyl-3,6,9,12-tetraoxo-1-phenyl-2-oxa-5,7,10,13,17-pentaazanonadecan-19-oic acid or a pharmaceutically acceptable salt thereof.

26. The compound according to claim 1 which is (2S,6S,9S,16S)-6-(3-{[Amino(imino)methyl]amino}propyl)-16-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-4,7,10-trioxo-3,5,8,11,15-pentaazaheptadecane-1,17-dioic acid or a pharmaceutically acceptable salt thereof.

27. The compound according to claim 1 which is tert-Butyl (2S,3R)-2-[(3-{[(2S)-2-amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

28. The compound according to claim 1 which is Ethyl (5S)-12-[(R)-[(2R,3R,4R,5R)-3,4-bis(acetyloxy)-5-(2,4-dioxo-3,4-dihydropyrimidin-1(2H)-yl)tetrahydrofuran-2-yl](hydroxy)methyl]-3,6-dioxo-1-phenyl-5-[(1S)-1-(tetradecanoyloxy)ethyl]-2-oxa-4,7,11-triazatridecan-13-oate or a pharmaceutically acceptable salt thereof.

29. The compound according to claim 1 which is tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate or a pharmaceutically acceptable salt thereof.

30. The compound according to claim 1 which is tert-Butyl (5R,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate or a pharmaceutically acceptable salt thereof.

31. The compound according to claim 1 which is tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate or a pharmaceutically acceptable salt thereof.

32. The compound according to claim 1 which is tert-Butyl (5S,12S)-12-[(S)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate or a pharmaceutically acceptable salt thereof.

33. The compound according to claim 1 which is tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate or a pharmaceutically acceptable salt thereof.

34. The compound according to claim 1 which is tert-Butyl (2S,3R)-2-[(3-{[(2S,3S)-2-amino-3-hydroxybutanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

35. The compound according to claim 1 which is tert-Butyl (5S,12S)-5-benzyl-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate or a pharmaceutically acceptable salt thereof.

36. The compound according to claim 1 which is tert-Butyl (2S,3R)-2-[(3-{[(2S)-2-amino-3-phenylpropanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

37. The compound according to claim 1 which is tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-methyl-3,6-dioxo-1-phenyl-2-oxa-4,7,11-triazatridecan-13-oate or a pharmaceutically acceptable salt thereof.

38. The compound according to claim 1 which is tert-Butyl (5S,12S)-5-[2-(benzyloxy)-2-oxoethyl]-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,6-dioxo-1-phenyl-2-oxa-4,7,11-triazatridecan-13-oate or a pharmaceutically acceptable salt thereof.

39. The compound according to claim 1 which is tert-Butyl (9S,16S)-9-{[(benzyloxy)carbonyl]amino}-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-3,10-dioxo-1-phenyl-2-oxa-4,11,15-triazaheptadecan-17-oate or a pharmaceutically acceptable salt thereof.

40. The compound according to claim 1 which is tert-Butyl (5S,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-[3-(tert-butoxy)-3-oxopropyl]-3,6-dioxo-1-phenyl-2-oxa-4,7,11-triazatridecan-13-oate or a pharmaceutically acceptable salt thereof.

41. The compound according to claim 1 which is 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~diazanyl)(imino)methyl]amino}propyl)-9-[(1S)-1-hydroxy-2-methylpropyl]-2-isopropyl-4,7,10-trioxo-3,5,8,11,15-pentaazaheptadecane-1,17-dioate or a pharmaceutically acceptable salt thereof.

42. The compound according to claim 1 which is (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-19,19-dimethyl-4,7,10,17-tetraoxo-18-oxa-3,5,8,11,15-pentaazaicosan-1-oic acid or a pharmaceutically acceptable salt thereof.

43. The compound according to claim 1 which is 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxida-2lambda~1~diazanyl)(imino)methyl]amino}propyl)-9-isobutyl-2-isopropyl-4,7,10-trioxo-3,5,8,11,15-pentaazaheptadecane-1,17-dioate or a pharmaceutically acceptable salt thereof.

44. The compound according to claim 1 which is (2S,6S,9S,16S)-6-(3-{[Amino(imino)methyl]amino}propyl)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-9-isobutyl-2-isopropyl-19,19-dimethyl-4,7,10,17-tetraoxo-18-oxa-3,5,8,11,15-pentaazaicosan-1-oic acid or a pharmaceutically acceptable salt thereof.

45. The compound according to claim 1 which is 1-Benzyl 17-(tert-butyl)(2S,6S,9S,16S)-16-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-6-(3-{[(2,2-dioxido-2lambda~1~diazanyl)(imino)methyl]amino}propyl)-9-[(1S)-1-hydroxyethyl]-2-isopropyl-4,7,10-trioxo-3,5,8,11,15-pentaazaheptadecane-1,17-dioate or a pharmaceutically acceptable salt thereof.

46. The compound according to claim 1 which is Ethyl (5S)-12-[(R)-[(2R,3R,4R,5S)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate or a pharmaceutically acceptable salt thereof.

47. The compound according to claim 1 which is Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate or a pharmaceutically acceptable salt thereof.

48. The compound according to claim 1 which is Ethyl (3R)-2-[(3-{[[(2S,3S)-2-amino-3-hydroxybutanoyl]amino}propyl)amino]-3-(2R,3R,4R,5S)-3,4-bis(acetyloxy)-5-(2,4-dioxo-3,4-dihydro-1(2H)-pyrimidinyl)tetrahydro-2-furanyl]-3-hydroxypropanoate or a pharmaceutically acceptable salt thereof.

49. The compound according to claim 1 which is Ethyl (3R)-2-[(3-{[[(2S,3S)-2-amino-3-hydroxybutanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]-3-hydroxypropanoate or a pharmaceutically acceptable salt thereof.

50. The compound according to claim 1 which is 16-Benzyl 2-ethyl (1R,9S,12S,16S)-1-[(2R,3R,4R,5S)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate or a pharmaceutically acceptable salt thereof.

51. The compound according to claim 1 which is 16-Benzyl 2-ethyl (1R,9S,12S,16S)-1-[(2R,3R,4R,5R)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl(imino)methyl]amino}propyl)-1-hydroxy-9-[(1S)-1-hydroxyethyl]-17-methyl-8,11,14-trioxo-3,7,10,13,15-pentaazaoctadecane-2,16-dicarboxylate or a pharmaceutically acceptable salt thereof.

52. The compound according to claim 1 which is Ethyl (5S)-12-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-5-[(1S)-1-hydroxy-2-methylpropyl]-3,6-dioxo-1-phenyl-2-oxa-4,7,11-triazatridecan-13-oate or a pharmaceutically acceptable salt thereof.

53. The compound according to claim 1 which is 16-Benzyl 2-ethyl (1R,9S,12S,16S)-1-[(2R,3R,4R,5S)-3,4-bis(acetyloxy)-5-(2,4-dioxo-3,4-dihydro-1(2H)-pyrimidinyl)tetrahydro-2-furanyl]-12-(3-{[(2,2-dioxido-2lambda~1~-diazanyl)(imino)methyl]amino}propyl)-1-hydroxy-9-[(1S)-2-methylpropyl]-17-methyl-8,11,14-trioxo-3,7,10,13,15-pentaazaoctadecane-2,16-dicarboxylate or a pharmaceutically acceptable salt thereof.

54. The compound according to claim 1 which is Ethyl (5S)-12-{(R)-(acetyloxy)[(2R,3R,4R,5S)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate or a pharmaceutically acceptable salt thereof.

55. The compound according to claim 1 which is Ethyl (5S)-12-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-5-isobutyl-3,6-dioxo-1-phenyl-2-oxa-4,7,11-triazatridecan-13-oate or a pharmaceutically acceptable salt thereof.

56. The compound according to claim 1 which is Ethyl (3R)-3-(acetyloxy)-2-[(3-{[[(2S)-2-amino-4-methylpentanoyl]amino}propyl)amino]-3-[(2R,3R,4R,5S)-3,4-bis(acetyloxy)-5-(2,4-dioxo-3,4-dihydro-1(2H)-pyrimidinyl)tetrahydro-2-furanyl]propanoate or a pharmaceutically acceptable salt thereof.

57. The compound according to claim 1 which is Ethyl (3R)-3-(acetyloxy)-2-[(3-{[(2S)-2-amino-4-methylpentanoyl]amino}propyl)amino]-3-[(2R,3R,4R,5R)-3,4-bis(acetyloxy)-5-(2,4-dioxo-3,4-dihydro-1(2H)-pyrimidinyl)tetrahydro-2-furanyl]propanoate or a pharmaceutically acceptable salt thereof.

58. The compound according to claim 1 which is 19-Benzyl 5-ethyl (4R,12S,15S,19S)-4-[(2R,3R,4R,5S)-3,4-bis(acetyloxy)-5-(2,4-dioxo-3,4-dihydro-1(2H)-pyrimidinyl)tetrahydro-2-furanyl]-15-(3-{[(2,2-dioxido-2lambda~1~-diazanyl)(imino)methyl]amino}propyl)-12-isobutyl-20-methyl-2,11,14,17-tetraoxo-3-oxa-6,10,13,16,18-pentaazahenicosane-5,19-dicarboxylate or a pharmaceutically acceptable salt thereof.

59. The compound according to claim 1 which is 1-Benzyl 17-ethyl (2S,6S,9S)-16-{(R)-(acetyloxy)[(2R,3R,4R,5R)-3,4-bis(acetyloxy)-5-(2,4-dioxo-3,4-dihydro-1(2H)-pyrimidinyl)tetrahydro-2-furanyl]methyl}-6-(3-{[(2,2-dioxido-2lambda~1~-diazanyl)(imino)methyl]amino}propyl)-9-isobutyl-2-isopropyl-4,7,10-trioxo-3,5,8,11,15-pentaazaheptadecane-1,17-dioate or a pharmaceutically acceptable salt thereof.

60. The compound according to claim 1 which is (2S,6S,9S)-6-(3-{[Amino(imino)methyl]amino}propyl)-16-[(R)-[(2R,3R,4R,5R)-3,4-bis(acetyloxy)-5-(2,4-dioxo-3,4-dihydro-1(2H)-pyrimidinyl)tetrahydro-2-furanyl](hydroxy)methyl]-9-[(1S)-1-hydroxy-2-methylpropyl]-2-isopropyl-4,7,10,17-tetraoxo-18-oxa-3,5,8,11,15-pentaazaicosan-1-oic acid or a pharmaceutically acceptable salt thereof.

61. The compound according to claim 1 which is tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oate or a pharmaceutically acceptable salt thereof.

62. The compound according to claim 1 which is tert-Butyl (2S,3R)-2-[(3-{[[(2S,3S)-2-amino-3-hydroxybutanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)-tetrahydro-2-furanyl]-3-hydroxypropanoate or a pharmaceutically acceptable salt thereof.

63. The compound according to claim 1 which is (5S,12S)-12-[(R)-[(3R,4R,5R)-4-{[tert-butyl(dimethyl)silyl]oxy}-3-hydroxy-5-(3-(4-methoxy-benzyl)-2,4-dioxo-3,4-dihydro-1(2H)-pyrimidinyl)tetrahydro-2-furanyl](hydroxy)methyl]-5-[(1S)-1-hydroxyethyl]-3,6-dioxo-1-phenyl-2-oxa-4,7,11-triazatridecan-13-oic acid or a pharmaceutically acceptable salt thereof.

64. The compound according to claim 1 which is (2S,3R)-2-[(3-{[(2S,3S)-2-Amino-3-hydroxybutanoyl]amino}propyl)amino]-3-{(3R,4R,5R)-4-{[tert-butyl(dimethyl)silyl]oxy}-5-[3-(4-methoxybenzyl)-2,4-dioxo-3,4-dihydropyrimidin-1(2H)-yl]tetrahydrofuran-2-yl}-3-hydroxypropanoic acid or a pharmaceutically acceptable salt thereof.

65. The compound according to claim 1 which is (4S,8S,11S,18S)-18-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-8-(3-{[(2,2-dioxido-2lambda~1~-diazanyl)(imino)methyl]amino}propyl)-11-isobutyl-4-isopropyl-3,6,9,12-tetraoxo-1-phenyl-2-oxa-5,7,10,13,17-pentaazanonadecan-19-oic acid or a pharmaceutically acceptable salt thereof.

66. The compound according to claim 1 which is tert-Butyl (5S,12S)-12-[(R)-[(3S,4R,5R)-3,4-dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate or a pharmaceutically acceptable salt thereof.

67. The compound according to claim 1 which is (5S,12S)-12-[(R)-[(3S,4R,5R)-3,4-Dihydroxy-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oic acid or a pharmaceutically acceptable salt thereof.

68. The compound according to claim 1 which is (2S,3R)-2-[(3-{[(2S)-2-Amino-4-methylpentanoyl]amino}propyl)amino]-3-[(3S,4R,5R)-3,4-dihydroxy-5-(3-(4-methoxybenzyl)-2,4-dioxo-3,4-dihydro-1(2H)-pyrimidinyl)tetrahydro-2-furanyl]-3-hydroxypropanoic acid or a pharmaceutically acceptable salt thereof.

69. The compound according to claim 1 which is (5S,12S)-12-[(R)-[(3S,4R,5R)-5-(2,4-Dioxo-3,4-dihydro-1(2H)-pyrimidinyl)-3,4-dihydroxy-tetrahydro-2-furanyl](hydroxy)methyl]-5-isobutyl-3,6-dioxo-1-phenyl-2-oxa-4,7,11-triazatridecan-13-oic acid or a pharmaceutically acceptable salt thereof.

70. The compound according to claim 1 which is tert-Butyl (5R,12S)-12-[(R)-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl](hydroxy)methyl]-5-isobutyl-3,6-dioxo-1-phenyl-2-oxa-4,7,11-triazatridecan-13-oate or a pharmaceutically acceptable salt thereof.

71. The compound according to claim 1 which is tert-Butyl (2S,3R)-2-[(3-{[(2R)-2-amino-4-methylpentanoyl]amino}propyl)amino]-3-[(3R,4R,5R)-3,4-bis{[tert-butyl(dimethyl)silyl]oxy}-5-(3-(4-methoxybenzyl)-2,4-dioxo-3,4-dihydro-1(2H)-pyrimidinyl)tetrahydro-2-furanyl]-3-hydroxypropanoate or a pharmaceutically acceptable salt thereof.

* * * * *

UNITED STATES PATENT AND TRADEMARK OFFICE
CERTIFICATE OF CORRECTION

PATENT NO.    : 6,858,591 B2
DATED         : February 22, 2005
INVENTOR(S)   : Ayako Yamashita and Emily Boucher Norton It is certified that error appears in the above-identified patent and that said Letters Patent is hereby corrected as shown below:

Column 131,
Line 45 delete "–C(O)R$^{14}$" and insert -- -C(O)OR$^{14}$ -- therefore.

Column 132,
Line 32, delete "-S(O)pR$^{16}$R$^{16}$" and insert -- -S(O)pR$^{15}$R$^{16}$ -- therefore.

Column 134,
Line 15, insert after "-C(O)R$^{15}$R$^{16}$" -- -C(O)R$^{16}$ --.

Signed and Sealed this

Seventeenth Day of May, 2005

JON W. DUDAS
*Director of the United States Patent and Trademark Office*